US012215310B2

United States Patent
Thevelein et al.

(10) Patent No.: US 12,215,310 B2
(45) Date of Patent: Feb. 4, 2025

(54) **MEANS AND METHODS TO MODULATE PROBIOTIC POTENCY OF THE YEAST *SACCHAROMYCES boulardii***

(71) Applicants: VIB VZW, Ghent (BE); KATHOLIEKE UNIVERSITEIT LEUVEN, K.U.LEUVEN R&D, Leuven (BE)

(72) Inventors: Johan Thevelein, Blanden (BE); Benjamin Offei, Leuven (BE); Maria Remedios Foulquié Moreno, Brussels (BE); Paul Vandecruys, Heusden-Zolder (BE)

(73) Assignees: VIB VZW, Ghent (BE); Katholieke Universiteit Leuven, Leuven (BE)

( * ) Notice: Subject to any disclaimer, the term of this patent is extended or adjusted under 35 U.S.C. 154(b) by 666 days.

(21) Appl. No.: 16/646,936

(22) PCT Filed: Sep. 14, 2018

(86) PCT No.: PCT/EP2018/074953
§ 371 (c)(1),
(2) Date: Mar. 12, 2020

(87) PCT Pub. No.: WO2019/053218
PCT Pub. Date: Mar. 21, 2019

(65) Prior Publication Data
US 2020/0270568 A1 Aug. 27, 2020

(30) Foreign Application Priority Data
Sep. 15, 2017 (EP) .................................... 17191252

(51) Int. Cl.
| | |
|---|---|
| *C12N 1/18* | (2006.01) |
| *A23L 33/14* | (2016.01) |
| *A61K 36/064* | (2006.01) |
| *C07K 14/395* | (2006.01) |
| *C12P 7/54* | (2006.01) |

(52) U.S. Cl.
CPC ................ *C12N 1/18* (2013.01); *A23L 33/14* (2016.08); *A61K 36/064* (2013.01); *C07K 14/395* (2013.01); *C12P 7/54* (2013.01); *A23V 2002/00* (2013.01)

(58) Field of Classification Search
CPC ....... C12N 1/18; A23V 2002/00; A23L 33/14; A61K 36/064; C07K 14/395; C12P 7/54
See application file for complete search history.

(56) References Cited

U.S. PATENT DOCUMENTS

2015/0329853 A1\* 11/2015 Zieler ................ C12N 15/1082
506/26

OTHER PUBLICATIONS

Chen, "Improved Acetic Acid Resistance in *Saccharomyces cerevisiae* by Overexpression of the WHI2 Gene Identified through Inverse Metabolic Engineering". Amer Soc for Microbio.; Applied and Environmental Microbiology (2016), 82:21 56-2166 (Year: 2016).\*
Giannattasio. "Molecular mechanisms of *Saccharomyces cerevisiae* stress adaptation and programmed cell death in response to acetic acid". Front. Microbiol., Feb. 20, 2013 <URL: https://www.frontiersin.org/articles/10.3389/fmicb.2013.00033/full> (Year: 2013).\*
Billoo, "Role of a probiotic (*Saccharomyces boulardii*) in management and prevention of diarrhoea". World J Gastroenterol. Jul. 28, 2006; 12(28): 4557-4560 <URL: https://www.ncbi.nlm.nih.gov/pmc/articles/PMC4125647/> (Year: 2006).\*
STIC Sequence Search, "SCORE_Results_1", obtained from search request via STIC, USPTO. (Year: 2022).\*
McCullough, "Species Identification and Virulence Attributes of *Saccharomyces boulardii* (nom. inval.)". J Clin Microbiol. Sep. 1998; 36(9): 2613-2617 <URL: https://www.ncbi.nlm.nih.gov/pmc/articles/PMC105172/> (Year: 1998).\*
Bermudez-Brito, "Probiotic Mechanisms of Action". Ann Nutr Metab 2012;61:160-174 <URL: https://www.karger.com/article/fulltext/342079> (Year: 2012).\*
Kaida, Daisuke, et al. "Yeast Whi2 and Psr1-phosphatase form a complex and regulate STRE-mediated gene expression." Genes to Cells 7.6 (2002): 543-552. (Year: 2002).\*
Chen, Yingying, et al. "Improved Acetic Acid Resistance in *Saccharomyces cerevisiae* by Overexpression of the WHI2 Gene Identified through Inverse Metabolic Engineering." Applied and Environmental Microbiology, vol. 82, No. 7, 2016, pp. 2156-2166.
Edwards-Ingram, Laura, et al. "Genotypic and Physiological Characterization of *Saccharomyces boulardii*, the Probiotic Strain of *Saccharomyces cerevisiae*." Applied and Environmental Microbiology, vol. 73, No. 8, 2007, pp. 2458-2467.
Offei, Benjamin et al., "Polygenic Analysis of Low pH Tolerance in *Saccharomyces cerevisiae* var. *boulardii*." 31st International Specialised Symposium on Yeast. Laboratory of Molecular Cell Biology, Institute of Botany and Microbiology, KU Leuven; Dept. of Molecular Microbiology, VIB, Kasteelpark Arenberg 31, Belgium, 2014, 4 pgs.
PCT International Search Report and Written Opinion; Application No. PCT/EP2018/074953 Applicant VIB VZW, filing date of Sep. 14, 2018, date of mailing Nov. 27, 2018, 10 pages.

(Continued)

*Primary Examiner* — Robert J Yamasaki
*Assistant Examiner* — Trevor Kane
(74) *Attorney, Agent, or Firm* — Patent Law Works LLP

(57) ABSTRACT

Described herein are probiotics, more particularly [to] the probiotic yeast *Saccharomyces boulardii*. Even more particularly described herein are enhanced probiotic potency *S. boulardii*. Also described here are mutant alleles useful to develop yeast strains with enhanced production of acetic acid. In addition, described here is the use of such yeast strains for the production of dietary supplements or pharmaceutical compositions to improve gastrointestinal comfort.

7 Claims, 14 Drawing Sheets
Specification includes a Sequence Listing.

(56) References Cited

OTHER PUBLICATIONS

Van Der Aa Kühle, Alis, et al. "In Vitro Screening of Probiotic Properties of *Saccharomyces cerevisiae* Var. *Boulardii* and Food-Borne *Saccharomyces cerevisiae* Strains." International Journal of Food Microbiology, vol. 101, No. 1, 2005, pp. 29-39.

Vandercruys, et al., "Polygenic Analysis of High Acetic Acid Accumulation, a Novel Putative Probiotic Property of *Saccharomyces cerevisiae* var. *boulardii*." KU Leuven—VIB (Belgium), 28th International Conference on Yeast Genetics and Molecular Biology (ICYGMB), Aug. 27-Sep. 1, 2017, Prague, Czech Republic. 4 pgs.

* cited by examiner

FIG. 8A

```
                 190            200                       320
                  |              |                         |
    S288c - CAVADRTGHALLHTLYGQALRHDTHF  ----  EGERFMERY
   SBERH6 - CAVADRTGHALLHTLYGQALRYDTHF  ----  EGERYMERY
      SBP - CAVADRTGHALLHTLYGQALRYDTHF  ----  EGERYMERY
      SBL - CAVADRTGHALLHTLYGQALRYDTHF  ----  EGERYMERY
      LSB - CAVADRTGHALLHTLYGQALRYDTHF  ----  EGERYMERY
     7136 - CAVADRTGHALLHTLYGQALRYDTHF  ----  EGERYMERY
     7301 - CAVADRTGHALLHTLYGQALRYDTHF  ----  EGERYMERY
      FLO - CAVADRTGHALLHTLYGQALRYDTHF  ----  EGERYMERY
       UL - CAVADRTGHALLHTLYGQALRYDTHF  ----  EGERYMERY
     7135 - CAVADRTGHALLHTLYGQALRYDTHF  ----  EGERYMERY
      259 - CAVADRTGHALLHTLYGQALRYDTHF  ----  EGERYMERY
      SBA - CAVADRTGHALLHTLYGQALRYDTHF  ----  EGERYMERY
      SAN - CAVADRTGHALLHTLYGQALRYDTHF  ----  EGERYMERY
      ENT - CAVADRTGHALLHTLYGQALRYDTHF  ----  EGERYMERY
```

FIG. 8B

```
                  190            200                       320
                   |              |                         |
    S288c - CAVADRTGHALLHTLYGQALRHDTHF  ----  EGERFMERY
   SBERH6 - CAVADRTGHALLHTLYGQALRYDTHF  ----  EGERYMERY
  AWR1796 - CAVADRTGHALLHTLYGQALRYDTHF  ----  EGERFMERY
     EC9-8 - CAVADRTGHALLHTLYGQALRYDTHF  ----  EGERFMERY
    BC187 - CAVADRTGHALLHTLYGQALRHDTHF  ----  EGERFMERY
   CEN.PK - CAVADRTGHALLHTLYGQALRHDTHF  ----  EGERFMERY
  D273-10B - CAVADRTGHALLHTLYGQALRHDTHF  ----  EGERFMERY
   Kyokai7 - CAVADRTGHALLHTLYGQALRHDTHF  ----  EGERFMERY
      K11 - CAVADRTGHALLHTLYGQALRHDTHF  ----  EGERFMERY
    JK9-3D - CAVADRTGHALLHTLYGQALRHDTHF  ----  EGERFMERY
 DBVPG6044 - CAVADRTGHALLHTLYGQALRHDTHF  ----  EGERFMERY
   FY1679 - CAVADRTGHALLHTLYGQALRHDTHF  ----  EGERFMERY
  Fosters0 - CAVADRTGHALLHTLYGQALRHDTHF  ----  EGERFMERY
    FL100 - CAVADRTGHALLHTLYGQALRHDTHF  ----  EGERFMERY
   Redstar - CAVADRTGHALLHTLYGQALRHDTHF  ----  EGERFMERY
   CBS7960 - CAVADRTGHALLHTLYGQALRHDTHF  ----  EGERFMERY
   CLIB324 - CAVADRTGHALLHTLYGQALRHDTHF  ----  EGERFMERY
    JAY291 - CAVADRTGHALLHTLYGQALRHDTHF  ----  EGERFMERY
    EC1118 - CAVADRTGHALLHTLYGQALRYDTHF  ----  EGERFMERY
   CLIB215 - CAVADRTGHALLHTLYGQALRYDTHF  ----  EGERFMERY
```

MEANS AND METHODS TO MODULATE PROBIOTIC POTENCY OF THE YEAST SACCHAROMYCES boulardii

FIELD OF THE INVENTION

The present invention relates to the field of probiotics, more particularly to the probiotic yeast *Saccharomyces boulardii*. Even more particularly the present invention relates to enhanced probiotic potency of *S. boulardii*. The present invention provides mutant alleles useful to develop yeast strains with enhanced production of acetic acid. In addition, the invention also relates to the use of such yeast strains for the production of dietary supplements or pharmaceutical compositions to improve gastrointestinal comfort.

BACKGROUND

Some microorganisms have found beneficial applications as probiotics in humans[1-4], animal husbandry[5,6] and aquaculture[7,8]. Probiotics are defined as live microorganisms that confer beneficial effects on their hosts when administered in drug-like quantities. They consist mainly of bacterial strains of the genera *Lactobacillus, Bifidobacterium, Enterococcus, Streptococcus* as well as the yeast *Saccharomyces cerevisiae* var *boulardii* (*S. boulardii*)[9,14]. Clinical evidence abounds for the beneficial applications of probiotics in treatment of gastrointestinal disorders, however there is a lack of solid scientific evidence supporting the unique character of probiotic potency in microorganisms and a total lack of knowledge about molecular mechanisms that could be responsible for their unique beneficial effects[12,13]. *S. boulardii* is the only yeast strain that is prescribed as probiotic against gastrointestinal diseases and it is commercially available from pharmacies worldwide. There are clinical trials supporting its application against Antibiotic Associated Diarrhoea (AAD)[25,26], gut inflammatory manifestations in HIV-1 patients[27] and recurrent *Clostridium difficile* infections when combined with classic antibiotics[28]. *S. boulardii* is also known to ameliorate diarrhoea as a result of gastrointestinal infections caused by enteropathogens such as *Vibrio cholera*, Enterohaemorrhagic *E. coli* (EHEC) and Enteropathogenic *E. coli* (EPEC)[29].

Here, we disclose a mutant allele of *S. boulardii* that provides the yeast with an unusually high production of acetic acid which is strongly inhibitory against colonization of the gut epithelium by pathogenic bacteria. The origin of *S. boulardii* can be traced back to south east Asia, where it was first isolated from lychee and mangosteen fruits in 1920 by Henry Boulard, a French microbiologist[15]. Although previously considered as a different species, modern molecular phylogenetic methods tend to consider it as a variety of the baker's yeast, *Saccharomyces cerevisiae* (*S. cerevisiae*)[16-19]. Whole-genome sequencing has indeed revealed that *S. boulardii* shares a highly similar genomic content and sequence to *S. cerevisiae*[20]. Despite the evidence of a close relationship with *S. cerevisiae*, *S. boulardii* exhibits some unique metabolic and physiological attributes. It shows much better tolerance to acidic conditions akin to that of the gastric milieu when compared to *S. cerevisiae*[21-23]. It possesses an enhanced ability for pseudohyphal switching[22] and thrives better at 37° C.[23]. It produces elevated levels of metabolites such as myo-inositol, 2-ethoxyindole and 4-hydrophenylethanol when compared to *S. cerevisiae*[17]. Furthermore, *S. boulardii* lacks the ability to sporulate[18,22], a trait commonly present in most *S. cerevisiae* strains[24]. It has remained unclear, however, in how far these unique properties are important for the probiotic potency of *S. boulardii*.

Multiple mechanisms have been proposed by which *S. boulardii* could act against enteropathogens. These include stemming the migration of T helper cells, which are needed to facilitate pro-inflammatory cytokine production, towards sites of inflammation[30]. It is also thought to protect against *Clostridium difficile* infections by stimulating the host to secrete adequate levels of Immunoglobulin A (IgA) against *C. difficile* toxin A[31], or by being involved in the degradation of the host's toxin receptor sites as well as proteolytic cleavage of *C. difficile* toxin A by a 54 kDa protease secreted by *S. boulardii*[32,33]. For *Shigella flexneri* infections, it has been demonstrated that *S. boulardii* protects against inflammation by mediating very low production levels of the pro-inflammatory cytokine IL-8 by the host[34]. Preservation of enterocyte barrier integrity by conferring on the host an enhanced capacity for tight junction protein secretion is another possibly important mechanism by which *S. boulardii* may act as a probiotic. It has also been demonstrated that *S. boulardii* binds EHEC (serogroup 0 157: H7) and *Salmonella typhimurium* (DT 104 mutant) in a lectin-mediated manner, suggesting that the beneficial effects of *S. boulardii* on gut health could be explained by its ability to adhere to some enteric pathogens and exclude them from attaching onto receptor sites of intestinal epithelial cells[35].

Secretion of antimicrobial agents is one mechanism of probiotic action commonly described for bacterial probiotics. These are usually in the form of antimicrobial peptides (bacteriocins)[39-41] or organic acids causing medium acidification[42,43]. Weak organic acids, particularly lactic acid and acetic acid, are important compounds, inhibiting a broad range of microorganisms (Helander et al 1997 Trends Food Sci & Technol 8:146-150). Acetic acid for example has been shown to exert antibacterial effects on different bacterial species (reviewed in Lew & Liong 2013 J Appl Microbiol 114:1241-1253). The bactericidal effects of acetic acid can be both due to its pH lowering capability, thereby making an environment unsuitable for growth of pathogens as well as to the chemical action of acetic acid itself (Lew & Liong 2013 J Appl Microbiol 114:1241-1253).

Identification of the polygenic basis of probiotic action in *S. boulardii* or in other *S. cerevisiae* strains that exhibit some particular probiotic attributes can provide a means for strengthening the probiotic action of *S. boulardii* or improve it in *S. cerevisiae* strains, using marker-assisted breeding or by allele exchange with genome editing technologies. Genetic linkage studies, such as pooled-segregant whole-genome sequence (PSWGS) analysis, combined with reciprocal hemizygosity analysis and allele exchange for identification of causative alleles, have proven very effective in dissecting the polygenic basis of commercially relevant traits in *S. cerevisiae* strains[44-47]. Moreover, exchange of superior alleles identified in this way has been employed successfully to construct *S. cerevisiae* strains with improved traits for industrial performance[44].

SUMMARY

Here, we report on the potential for antimicrobial compound production in *S. boulardii* and disclose a recessive mutant WHI2 (WHISKEY2) allele responsible for high acetic acid levels that are strongly inhibitory to bacterial growth. By QTL mapping with pooled-segregant whole-genome sequence analysis, reciprocal hemizygosity analysis and allele exchange, genetic elements responsible for this trait have been identified down to the nucleotide level. While the WHI2 mutation is absent from all sequenced *S. cerevisiae* strains and are unique for *S. boulardii*, only few strains are homozygous for this causative mutation in WHI2. Transfer of this mutation to other *S. boulardii*, heterozygous for this mutation, establishes high acetic acid accumulation in these strains. This work reveals for the first time the molecular-genetic basis of a typical probiotic property. Whi2 (Whiskey 2) is known to be involved in stress responses. It interacts with Psr1 to activate the transcription factors Msn2/Msn4 that initiate the stress response pathway (Kaida et al 2002 Genes to Cells 7, 543-552). Chen et al 2016 (Appl Environ Microbiol 82, 2156-2166) demonstrated that Whi2 is part of the acetic acid resistance pathway and that Whi2 overexpressing *S. cerevisiae* strains have improved fermentation efficiency in the presence of acetic acid. However, to the best of Applicant's knowledge, WHI2 has never been anticipated to be involved in acetic acid production, acetic acid accumulation, acetic acid consumption or probiotic capacity of *S. boulardii*.

It is an object of the application to provide a *S. boulardii* strain with a disrupted or deleted WHI2 allele. This is equivalent as saying that a *S. boulardii* strain is provided which is deficient of the WHI2 allele. More particularly, a *S. boulardii* strain is provided comprising a homozygous or hemizygous mutant WHI2 allele wherein said WHI2 allele compromises, partially abolishes or completely abolishes Whi2 function, wherein said strain is not the *S. boulardii* strain Sb.P or Sb.A or a diploid Sb.P or Sb.A. *S. boulardii* is not able to sporulate in nature. In this application a method is described by which haploid segregants can be induced. Therefore, this application also provides a haploid segregant of a *S. boulardii* strain comprising a disrupted, partially deleted or completely deleted WHI2 allele.

It is also an object of the application to provide a mutant WHI2 yeast allele comprising a nonsense mutation on nucleic acid position 860. Consequently, also a haploid segregant of a *S. boulardii* strain comprising said mutant WHI2 allele is provided as well as a yeast strain comprising said mutant WHI2 allele in a homozygous or hemizygous form, wherein said strain is not a diploid *S. boulardii* Sb.P or Sb.A strain or not a Sb.P or Sb.A strain.

In this application it is disclosed that the herein described mutant WHI2 allele comprises a temperature sensitive mutation resulting in a growth deficiency on acetic acid at 37° C. Therefore another object of the application is a *Saccharomyces boulardii* strain producing a cell-free supernatant with a pH lower than 5 at 37° C., wherein the acidification of said supernatant is due to the production of acetic acid by said *S. boulardii* strain and wherein said *S. boulardii* strain is not strain Sb.P or Sb.A or not a diploid Sb.P or Sb.A. More particularly, said *S. boulardii* strain is growth deficient on acetic acid. Given the established use of *S. boulardii* as probiotic microorganism and the herein disclosed antibiotic effect of acetic acid production, a dietary supplement or pharmaceutical composition comprising a yeast strain is provided, wherein said yeast strain comprises a homozygous or hemizygous mutant WHI2 allele compromising, partially abolishing or completely abolishing Whi2 function. Also, said pharmaceutical composition or a yeast strain comprising a homozygous or hemizygous mutant WHI2 allele compromising, partially abolishing or completely abolishing Whi2 function is provided for use as a medicament, more particularly for use in the treatment or prevention of gastrointestinal disorders, even more particularly for the treatment or prevention of diarrhea. Also, the use of said yeast strain is provided as a live probiotic additive to foodstuff and/or feedstuff as well as for the production of acetic acid. Consequently, the use of a disrupted, partially deleted or completely deleted WHI2 yeast allele is provided to develop an acetic acid producing yeast.

In another aspect, a method is provided for maintaining or improving the health of the gastrointestinal tract in a human or animal, said method comprising administering to said human or animal, a dietary supplement or pharmaceutical composition comprising a yeast strain is provided, wherein said yeast strain comprises a homozygous or hemizygous mutant WHI2 allele compromising, partially abolishing or completely abolishing Whi2 function. More particularly, said maintaining or improving the health of the gastrointestinal tract comprises reducing the number of pathogenic bacteria found in the faeces of said human or animal. Even more particularly, said pathogenic bacteria are selected from the group consisting of Clostridia, *Escherichia*, *Salmonella*, *Shigella* and mixtures thereof.

BRIEF DESCRIPTION OF THE FIGURES

FIG. 8. Sequence comparison of selected regions in Sdh1 from *S. boulardii* and *S. cerevisiae*. A. Alignment of the Sdh1 amino acid sequence in regions 181-206 and 313-321 of the *S. boulardii* strains with the corresponding sequence in *S. cerevisiae* S288c Sdh1. B. Alignment of the Sdh1 amino acid sequence in regions 181-206 and 313-321 of the *S. cerevisiae* strains with the corresponding sequence in *S. boulardii* SBERH6 Sdh1.

DETAILED DESCRIPTION

Definitions

Figure 1:
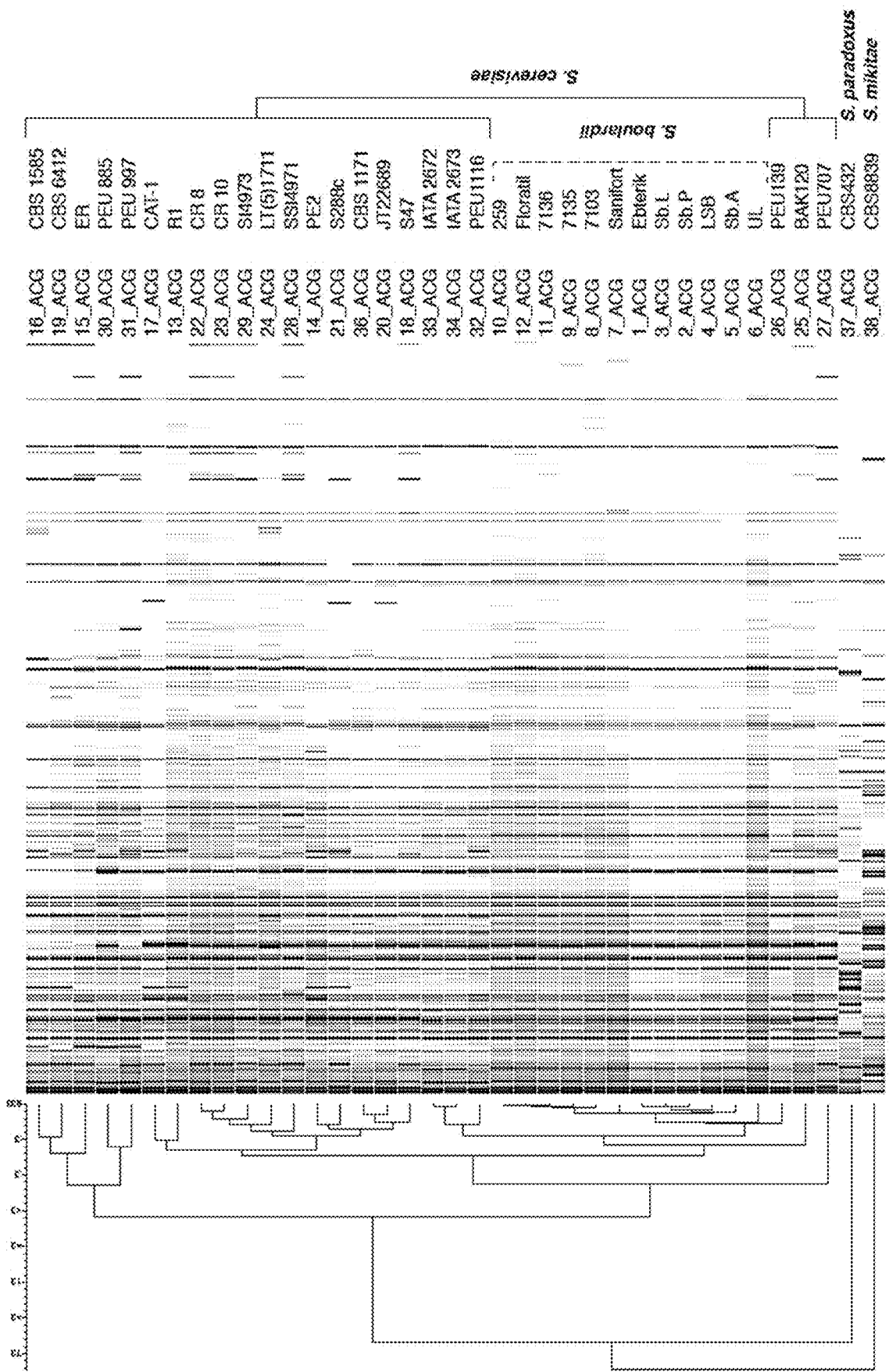
FIG. 1. Phylogenetic typing of *S. boulardii* and other *Saccharomyces* strains. Amplified Fragment Length Polymorphism (AFLP) analysis was used to type all 37 strains. *S. boulardii* (Sb) strains formed a single cluster flanked by two *S. cerevisiae* (Sc) clusters. *S. paradoxus* (Sp) and *S. mikatae* (Sm) showed a more distant relationship to both *S. boulardii* and *S. cerevisiae*.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Michael R. Green and Joseph Sambrook, Molecular Cloning: A Laboratory Manual, 4th ed., Cold Spring Harbor Laboratory Press, Plainsview, New York (2012); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

In this application, a temperature sensitive mutation in the WHI2 gene of *Saccharomyces boulardii* is disclosed. Said mutation leads to a deficiency to consume acetic acid at 37° C. This inability to grow on acetic acid while producing acetic acid results in a high acetic acid accumulation. This trait provides yeast cells with a double industrial application, i.e. more efficient production of acetic acid and an improved probiotic effect given that acetic acid producing microorganisms protect the gut epithelium against colonization by pathogenic bacteria.

Therefore and in a first aspect, a *S. boulardii* strain is provided in which the WHI2 allele has been disrupted or deleted. Given that *S. boulardii* is diploid this is equivalent as saying that a *S. boulardii* strain is provided in which both endogenous WHI2 alleles have been disrupted or deleted. Disruption of an allele as used herein means inserting a DNA fragment in the base sequence of said allele or deleting a portion of said allele so that the allele cannot function any longer. As a result of gene (or allele) disruption, the gene (or allele) cannot be transcribed into mRNA, hence the structural gene is not translated, or the transcription product mRNA becomes incomplete, hence mutation or deletion occurs in the amino acid sequence of the translation product structural protein, rendering the protein incapable of performing the original function. In order to disrupt the WHI2 allele, any site may be disrupted, for example, a promoter site of WHI2, an open reading frame (ORF) site, and a terminator site, or combination thereof may be disrupted. Gene disruption can also be carried out by deleting the whole WHI2 gene. Therefore in alternative embodiments, a S. boulardii strain is provided comprising a completely deleted WHI2 allele or a S. boulardii strain devoid of the WHI2 allele or deficient of the WHI2 allele. In particular embodiments, said S. boulardii strains comprise a homozygous or hemizygous disrupted WHI2 allele. Also, a S. boulardii strain is provided in which the WHI2 allele has been disrupted or deleted by homologous recombination.

The WHI2 allele can be disrupted, for example, by transforming a plasmid or a fragment thereof for disrupting the WHI2 allele into yeast, and causing homologous recombination of the DNA fragment contained in the transformed plasmid or fragment thereof with the gene on yeast genome. In case that a plasmid for disruption of the WHI2 gene or a fragment thereof and the WHI2 gene on the yeast genome have a homology to an extent for causing homologous recombination, homologous recombination is caused. Whether a DNA fragment can cause homologous recombination can be confirmed by introducing the fragment into yeast, and determining whether any strain in which homologous recombination has been caused can be isolated, that is, whether the supernatant of the yeast culture acidifies to a pH lower than 5, preferably lower than 4.8, more preferably lower than 4.4.

It will be understood that methods for gene disruption in yeast and other microorganisms are well known, and the particular method used to reduce or abolish the expression of the endogenous gene is not critical to the invention. In one embodiment, disruption can be accomplished by homologous recombination, whereby the gene to be disrupted is interrupted (e.g., by the insertion of a selectable marker gene) or made inoperative (e.g., "gene knockout"). Methods for gene knockout and multiple gene knockout are well known. See, e.g. Rothstein, 2004, "Targeting, Disruption, Replacement, and Allele Rescue: Integrative DNA Transformation in Yeast" In: Guthrie et al., Eds. Guide to Yeast Genetics and Molecular and Cell Biology, Part A, p. 281-301; Wach et al., 1994, "New heterologous modules for classical or PCR-based gene disruptions in Saccharomyces cerevisiae" Yeast 10:1793-1808. Methods for insertional mutagenesis are also well known. See, e.g., Amberg et al., eds., 2005, Methods in Yeast Genetics, p. 95-100; Fickers et al., 2003, "New disruption cassettes for rapid gene disruption and marker rescue in the yeast Yarrowia lipolytica" Journal of Microbiological Methods 55:727-737; Akada et al., 2006, "PCR-mediated seamless gene deletion and marker recycling in Saccharomyces cerevisiae" Yeast 23:399-405; Fonzi et al., 1993, "Isogenic strain construction and gene mapping in Candida albicans" Genetics 134:717-728. Other methods to disrupt a gene in a microorganism include the use of nucleases, such as zinc-finger nucleases (ZFNs), Transcription Activator-Like Effector Nucleases (TALENs), meganucleases but especially the CRISPR-Cas system. "Nucleases" as used herein are enzymes that cut nucleotide sequences. These nucleotide sequences can be DNA or RNA. If the nuclease cleaves DNA, the nuclease is also called a DNase. If the nuclease cuts RNA, the nuclease is also called an RNase. Upon cleavage of a DNA sequence by nuclease activity, the DNA repair system of the cell will be activated. Yet, in most cases the targeted DNA sequence will not be repaired as it originally was and small deletions, insertions or replacements of nucleic acids will occur, mostly resulting in a mutant DNA sequence. ZFN are artificial restriction enzymes generated by fusing a zinc finger DNA-binding domain to a DNA cleavage domain. Zinc finger domains can be engineered to target desired DNA sequences, which enables zinc-finger nucleases to target a unique sequence within a complex genome. By taking advantage of endogenous DNA repair machinery, these reagents can be used to precisely alter the genomes of simple and higher organisms. Other technologies for genome customization that can be used to knock out genes are meganucleases and TAL effector nucleases (TALENs, Cellectis bioresearch). A TALEN® is composed of a TALE DNA binding domain for sequence-specific recognition fused to the catalytic domain of an endonuclease that introduces double strand breaks (DSB). The DNA binding domain of a TALEN® is capable of targeting with high precision a large recognition site (for instance 17 bp). Meganucleases are sequence-specific endonucleases, naturally occurring "DNA scissors", originating from a variety of single-celled organisms such as bacteria, yeast, algae and some plant organelles. Meganucleases have long recognition sites of between 12 and 30 base pairs. The recognition site of natural meganucleases can be modified in order to target native genomic DNA sequences (such as endogenous genes). Another recent and very popular genome editing technology is the CRISPR-Cas system, which can be used to achieve RNA-guided genome engineering. CRISPR interference is a genetic technique which allows for sequence-specific control of gene expression in prokaryotic and eukaryotic cells. It is based on the bacterial immune system-derived CRISPR (clustered regularly interspaced palindromic repeats) pathway and has been modified to edit basically any genome. By delivering the Cas nuclease (in many cases Cas9) complexed with a synthetic guide RNA (gRNA) in a cell, the cell's genome can be cut at a desired location depending on the sequence of the gRNA, allowing existing genes to be removed and/or new one added and/or more subtly removing, replacing or inserting single nucleotides (e.g. DiCarlo et al 2013 Nucl Acids Res doi: 10.1093/nar/gkt135; Sander & Joung 2014 Nat Biotech 32:347-355). Therefore, also a S. boulardii strain is provided in which the WHI2 allele has been disrupted or deleted by using nuclease technology, more particularly by means of the CRISPR-Cas technology.

As introduced earlier, Saccharomyces cerevisiae var. boulardii (or S. boulardii as used herein) is a strain of S. cerevisiae, sharing very high genomic relatedness. S. boulardii can therefore also be defined as a Saccharomyces cerevisiae strain related to Saccharomyces boulardii. S. boulardii is well known as a probiotic with the purpose of introducing beneficial active cultures into the large and small intestine of humans and animals, as well as conferring protection against pathogenic microorganisms in the host. Many S. boulardii strains are available including several strains that are commercially available. Of particular interest for this application is S. boulardii strain Sb.P and Sb.A. Said strains are described in van der Aa Kühle et al 2005 (Int J Food Microbiol 101, 29-39), which is herein incorporated as reference. "WHI2" or "Whi2" as used herein refers to the WHISKEY2 gene or Whiskey2 protein respectively of *Saccharomyces*. The WHI2 gene is depicted in SEQ ID No. 3 and the Whi2 protein is depicted in SEQ ID No.4. The mutant WHI2 allele which is disclosed in this application is depicted in SEQ ID No. 1. WHI2 is also known in the art as YOR043W (SGD ID: S000005569, Chromosome XV 410870 . . . 412330). In particular embodiments of the first aspect and of all its embodiments, said *S. boulardii* strain is an engineered or recombinant *S. boulardii* strain. In other particular embodiments of the first aspect and of all its embodiments, said *S. boulardii* strain is a haploid *S. boulardii* strain.

In a second aspect, a mutant WHI2 yeast allele is provided comprising a mutation on nucleic acid position 860. In one embodiment, said mutant WHI2 allele is an isolated mutant WHI2 yeast allele. In particular embodiments, said mutation is a nonsense or missense mutation. In more particular embodiments, said mutant allele is a whi2S270* allele or encodes a Whi2 protein comprising a S270* mutation. In even more particular embodiments said mutant allele comprises a C860G mutation. In most particular embodiments, said mutant allele is the allele as depicted in SEQ ID No. 1. In the rest of this document, the above described mutant WHI2 yeast alleles will be referred to as "one of the mutant WHI2 alleles of the application".

A "nonsense mutation" as used herein refers to a point mutation in a sequence of DNA that results in a premature stop codon (often illustrated as '*'), or a nonsense codon in the transcribed mRNA, and in a truncated, incomplete, and nonfunctional protein product. A "missense mutation" means a point mutation where a single nucleotide is changed to cause substitution of a different amino acid.

A "mutation on nucleic acid position 860" is equivalent as saying that the nucleobase on position 860 is mutated. With "mutation on nucleic acid position 860" as used herein, it is thus meant that nucleobase 860 from the wild-type WHI2 gene as depicted in SEQ ID No. 3 is mutated. "Position 860" or "nucleobase 860" as used herein refers to the nucleobase that is 859 positions removed downstream from the first nucleobase (i.e. adenosine) from the start codon. This nucleobase 860 is a cytosine (C) and its position is indicated in SEQ ID No. 3 by underlining. In the specific mutant WHI2 allele disclosed in the application said C is replaced by a guanine (G). As such the mutation can also be referred to as a C860G mutation. Given that said mutation changes a serine(S) codon into a premature stop codon (*), said WHI2 allele can also be referred to as a whiS270* allele or an allele that encodes a S270* mutation.

"Nucleobases" are nitrogen-containing biological compounds that form nucleosides, which in turn are components of nucleotides; all which are monomers that are the basic building blocks of nucleic acids. Often simply called bases, as in the field of genetics, the ability of nucleobases to form base-pairs and to stack one upon another leads directly to long-chain helical structures such as ribonucleic acid (RNA) and deoxyribonucleic acid (DNA). There are four so-called DNA-bases: adenine (A), cytosine (C), guanine (G) and thymine (T).

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g. peptide nucleic acids).

By "encoding" or "encodes" or "encoded", with respect to a specified nucleic acid, is meant comprising the information for transcription into an RNA molecule and in some embodiments, translation into the specified protein or amino acid sequence. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code.

In a third aspect, a *S. boulardii* strain is provided comprising a homozygous or hemizygous mutant WHI2 allele compromising, partially abolishing or completely abolishing Whi2 function, wherein said strain is not a diploid *S. boulardii* strain Sb.P or Sb.A or wherein said strain is not Sb.P or Sb.A. An allele that compromises, partially abolishes or completely abolishes Whi2 function is equivalent to a disrupted, partially deleted or completely deleted WHI2 allele. In a particular embodiment, a *S. boulardii* strain is provided comprising a homozygous or hemizygous mutant WHI2 allele, wherein said mutant allele comprises a non-sense or missense mutation on nucleic acid position 860. In more particular embodiments, said mutant WHI2 allele is a whi2S270* allele or encodes a Whi2 protein comprising a S270* mutation. In even more particular embodiments said mutant WHI2 allele comprises a C860G mutation. In most particular embodiments, said mutant WHI2 allele is the allele as depicted in SEQ ID No. 1.

"Disrupted, partially deleted or completely deleted function" or "disrupting, partially deleting or completely deleting the functional expression" is equivalent as saying partially or completely inhibiting the formation of a functional mRNA molecule encoding Whi2. Means and methods to disrupt, partially delete or completely delete a gene or protein are well known in the art. The skilled person can select from a plethora of techniques to affect the expression or function of Whi2. One very efficient technique is the Crispr/Cas technology which has also been used in the Examples of this application. At the DNA level, disruption, partial deletion or complete deletion can for example be achieved by removing or disrupting a gene encoding Whi2 or by mutations in the promoter of a gene encoding Whi2. Non-limiting examples are knock-outs or loss-of-function mutations but also gain-of-function mutations and dominant negative mutations can disrupt the functional expression or inhibit the formation of a functional mRNA molecule. A "knock-out" can be a gene knockdown (leading to reduced gene expression) or the gene can be knocked out by a mutation such as, a point mutation, an insertion, a deletion, a frameshift, or a missense mutation by techniques known in the art. The lack of transcription can e.g. be caused by epigenetic changes (e.g. DNA methylation) or by loss-of-function mutations. A "loss-of-function" or "LOF" mutation as used herein is a mutation that prevents, reduces or abolishes the function of a gene product as opposed to a gain-of-function mutation that confers enhanced or new activity on a protein. The disclosed WHI2 mutant allele has a loss-of-function effect and is recessive, meaning that the mutation has to be homozygous or hemizygous to lead to the mutant phenotype. Both dominant negative or LOF mutations can be caused by a wide range of mutation types, including, but not limited to, a deletion of the entire gene or part of the gene, splice site mutations, frame-shift mutations caused by small insertions and deletions, nonsense mutations, missense mutations replacing an essential amino acid and mutations preventing correct cellular localization of the product.

"Homozygous" refers to having identical alleles for a single trait. An "allele" represents one particular form of a gene. Alleles can exist in different forms and diploid organisms typically have two alleles for a given trait. A homozygous mutant WHI2 allele thus means that all WHI2 alleles are identical. "Hemizygous" refers to having only one allele for a single trait or gene. In case of a diploid organism thus only one allele of its pairs is present, while all other genes are represented by two alleles. This can for example be achieved by deleting one allele of a gene or by introducing one allele of a gene that is not present in an organism.

In another embodiment, a haploid segregant of a *S. boulardii* strain comprising a disrupted, partially deleted or completely deleted WHI2 allele is provided. In a particular embodiment, said haploid segregant comprises a mutant WHI2 yeast allele comprising a nonsense or missense mutation on nucleic acid position 860. In more particular embodiments, said mutant WHI2 allele is a whi2S270* allele or encodes a Whi2 protein comprising a S270* mutation. In even more particular embodiments said mutant WHI2 allele comprises a C860G mutation. In most particular embodiments, said mutant WHI2 allele is the allele as depicted in SEQ ID No. 1.

Haploid cells contain one set of chromosomes, while diploid cells contain two. A haploid segregant as used herein is equivalent as a haploid spore, the result of sporulation.

Yeasts are eukaryotic, single-celled microorganisms classified as members of the fungus kingdom and like all fungi, yeast may have asexual and sexual reproductive cycles. The most common mode of vegetative growth in yeast is asexual reproduction by budding. Here, a small bud or daughter cell, is formed on the parent cell. The nucleus of the parent cell splits into a daughter nucleus and migrates into the daughter cell. The bud continues to grow until it separates from the parent cell, forming a new cell. This reproduction cycle is independent of the yeast's ploidy, thus both haploid and diploid yeast cells can duplicate as described above. Haploid cells have in general a lower fitness and they often die under high-stress conditions such as nutrient starvation, while under the same conditions, diploid cells can undergo sporulation, entering sexual reproduction (meiosis) and producing a variety of haploid spores or haploid segregants, which can go on to mate (conjugate), reforming the diploid. The budding yeast *Saccharomyces cerevisiae* reproduces by mitosis as diploid cells when nutrients are abundant, but when starved, this yeast undergoes meiosis to form haploid spores. Haploid cells may then reproduce asexually by mitosis. Importantly, *S. boulardii* is sporulation deficient (Edwards-Ingram et al 2007 Appl Environ Microbiol 73:2458-2467) and thus does not have the ability to naturally form haploid spores or haploid segregants. In particular embodiments of the third aspect and of all its embodiments, said *S. boulardii* strain is an engineered or recombinant *S. boulardii* strain.

In a fourth aspect, a yeast strain comprising a homozygous or hemizygous WHI2 mutant allele is provided, wherein said allele is the WHI2 yeast allele comprising a nonsense or missense mutation on nucleic acid position 860, more particularly said mutant WHI2 allele is a whi2S270* allele or encodes a Whi2 protein comprising a S270* mutation, even more particularly said mutant WHI2 allele comprises a C860G mutation, most particularly said mutant WHI2 allele is the allele as depicted in SEQ ID No. 1, and wherein said strain is not a diploid *S. boulardii* Sb.P or Sb.A strain or not a Sb.P or Sb.A strain. In one embodiment, said yeast is growth deficient on acetic acid, preferably at 37° C. In a more particular embodiment, said yeast strain produces a cell-free supernatant with a pH lower than 5 at 37° C. In even more particular embodiments, said pH lower than 5 is a pH lower than 4.8, lower than 4.6, lower than 4.4, lower than 4.3 or is equal to or lower than a pH of 4.2. In even more particular embodiments, said yeast strain is growth deficient on acetic acid, particularly at 37° C. and in aerobic conditions. In even more particular embodiments, said yeast strain produces a cell-free supernatant with a pH lower than 5, lower than 4.8, lower than 4.6 or lower than 4.4 at 37° C. due to the accumulation of acetic acid. In other particular embodiments, said yeast is a recombinant or an engineered yeast.

"Engineering" or "engineered" as used herein refers to genetic engineering, a technique whereby an organism's genome is modified using biotechnology. This includes but is not limited to the transfer of genes within and across species boundaries, deleting fragments of genes or deleting whole genes, modifying the DNA sequence of an organism by deleting, inserting or substituting one or more nucleic acid molecules. Means and methods to engineer microorganisms, particularly yeasts are well known by the person skilled in the art. The most known techniques involve traditional genetic transformation of yeast and recombinant DNA techniques. Nowadays, the most attractive technique to engineer a microorganism is by the use of nucleases, such as zinc-finger nucleases (ZFNs), Transcription Activator-Like Effector Nucleases (TALENs), meganucleases but especially the CRISPR-Cas system as described earlier.

In more particular embodiments, said yeast is useful for probiotic use or for acetic acid production, including, but not limited to *Saccharomyces, Zygosaccharomyces*, Brettanomyces and *Kluyveromyces*. Particularly, said yeast is a *Saccharomyces* sp., even more particularly it is a *Saccharomyces cerevisiae* sp., even more particularly it is a *S. cerevisiae* var. *boulardii*, even more particularly it is a haploid *S. boulardii*, most particularly it is not a diploid *S. boulardii* Sb.P or Sb.A strain or not a Sb.A or Sb.P strain. "Acetic acid" (systematically named ethanoic acid) as used herein refers the colorless liquid organic compound with the chemical formula $CH_3COOH$ (also written as $CH_3CO_2H$ or $C_2H_4O_2$). Acetic acid is the second simplest carboxylic acid (after formic acid). It consists of a methyl group attached to a carboxyl group. It is an important chemical reagent and industrial chemical, used primarily in the production of cellulose acetic acid for photographic film, polyvinyl acetic acid for wood glue, and synthetic fibres and fabrics. In households, diluted acetic acid is often used in descaling agents. In the food industry, acetic acid is controlled by the food additive code E260 as an acidity regulator and as a condiment. As a food additive it is approved for usage in many countries. Acetic acid is also known as an antibiotic compound, as was demonstrated in this application, e.g. Example 3. Also in the art, extensive evidence for acetic acid as anti-microbial compound is available (e.g. Rhee et al 2003 Appl Environ Microbiol 69:2959-2963; Ryssel et al 2009 Burns 35:695-700; Fraise et al 2013 J Hosp Infec 84:329-331).

In a fifth aspect a *Saccharomyces boulardii* strain producing a cell-free supernatant with a pH lower than 5 at 37° C. is provided, wherein the acidification of said supernatant is due to the production or accumulation of acetic acid by said *S. boulardii* strain and wherein said *S. boulardii* strain is not strain Sb.P or Sb.A, or not a diploid Sb.P or Sb.A. In one embodiment a *S. boulardii* culture is provided, wherein said culture comprises or consists of a *Saccharomyces boulardii* strain producing a cell-free supernatant with a pH lower than 5 at 37° C., wherein the acidification of said supernatant is due to the production or accumulation of acetic acid by said *S. boulardii* strain and wherein said *S. boulardii* strain is not strain Sb.P or Sb.A, or not a diploid Sb.P or Sb.A. In other particular embodiments, said *S. boulardii* strain is growth deficient on acetic acid and the production or accumulation of acetic acid by said *S. boulardii* strain is because of its growth deficiency on acetic acid. Thus, a *Saccharomyces boulardii* strain or culture is provided producing a cell-free supernatant with a pH lower than 5 at 37° C., wherein the acidification of said supernatant is due to the growth deficiency on acetic acid of said *S. boulardii* strain and wherein said *S. boulardii* strain is not strain Sb.P or Sb.A, or not a diploid Sb.P or Sb.A.

In alternative embodiments, a *S. boulardii* strain or a *Saccharomyces cerevisiae* strain related to *S. boulardii* is provided, wherein said strain due to the presence of a disrupted, partially deleted or completely deleted WHI2 allele produces a cell-free supernatant with a pH lower than 5 at 37° C., is growth deficient on acetic acid or produces a cell-free supernatant with a pH lower than 5 at 37° C. because of its growth deficiency on acetic acid, wherein said growth deficiency on acetic acid is induced by said disrupted, partially deleted or completely deleted WHI2 allele and wherein said disrupted, partially deleted or completely deleted WHI2 allele is present in a homozygous or hemizygous form and wherein said *S. boulardii* strain is not strain Sb.P or Sb.A, or not a diploid Sb.P or Sb.A. In a particular embodiment, said disrupted, partially deleted or completely deleted WHI2 allele comprises a nonsense or missense mutation on nucleic acid position 860, more particularly is a whi2S270* allele or encodes a Whi2 protein comprising a S270* mutation, even more particularly comprises a C860G mutation, most particularly is the allele as depicted in SEQ ID No. 1.

In particular embodiments, said acetic acid is produced or accumulated by said *S. boulardii* strain or said *S. boulardii* strain is growth deficient on acetic acid in a temperature range between 35° C. and 39° C., or between 36° C. and 38° C., or between 36° and 37.5°, or between 36.5° C. and 37.5° C. or most particularly at 37° C. In other particular embodiments, said "pH lower than 5" is a pH lower than 4.9, or lower than 4.8, or lower than 4.7, or lower than 4.6, or lower than 4.5, or lower than 4.4, or lower than 4.3, or lower than or equal to 4.2 or is a pH between 5 and 4.6, or between 4.9 and 4.2, or between 4.8 and 4.1, or between 4.5 and 4.2. In particular embodiments of the fifth aspect and of all its embodiments, said *S. boulardii* strain is a recombinant or engineered strain.

It is well established in the art that *S. boulardii* is efficacious against bacterial infections, inflammatory bowel diseases and other gastrointestinal disorders (e.g. Jawhara & Poulain 2007 Med Mycol 45:691-700; Collier et al 2011 J Anim Sc 89:52-58; Justino et al 2014 Br J Nutr 111:1611-1621; Martins et al 2013 Microbes and Infection 15:270-279). In current application Applicants demonstrate that at least a significant part of the antimicrobial activity of *S. boulardii* can be attributed to its production of the antimicrobial compound acetic acid. Moreover, it is herein disclosed that a partially or completely disrupted WHI2 allele lead to enhanced production of acetic acid by *S. boulardii* strains comprising said mutant allele and that said *S. boulardii* strains have increased antimicrobial activity in vitro. Hence the optimized yeasts or more particularly the optimized *S. boulardii* strains of the application are envisaged to be used as medicament, more particular as probiotic and/or dietary supplement. The effect of optimized *S. boulardii* strains can be easily tested in vivo, especially if it is already known that said strains have antimicrobial activity in vitro. A selection of an overwhelming number of papers can be found below.

Jawhara and Poulain (2007, Med Mycol 45:691-700) analysed the effect of *Saccharomyces boulardii* on inflammation and intestinal colonization by *Candida albicans* in a mice model for colitis. Experimental details can be found therein, but briefly BALB/c mice were colonized with *C. albicans* by oral gavage with a 200 ml suspension of $10^7$ yeast cells. A 1.5% solution of DSS was administered in drinking water 1 h after *C. albicans* oral challenge, while $10^{7Us\ of}$ *S. boulardii* was inoculated daily by oral gavage for 1 week. Faeces were collected daily for 2 weeks and samples of the colon were taken for histological scoring and real-time PCR (RT-PCR) analysis of inflammatory cytokines and toll-like receptors (TLRs). Both the colony forming units (CFUs) of *C. albicans* and the inflammation were greatly reduced in mice receiving *S. boulardii*.

Justino et al (2014, B J Nutr 111:1611-1621) treated a 5-fluorouracil (5-FU)-induced intestinal mucositis mice model with *S. boulardii*. Mice were divided into control, control+5-FU or 5-FU+*S. boulardii* ($16 \times 10^9$ CFUs/kg) treatment groups, and the jejunum and ileum were removed after killing of mice for the evaluation of histopathology and inflammation. *S. boulardii* significantly reversed the histopathological changes in intestinal mucositis induced by 5-FU and reduced the inflammatory parameters.

Martins et al (2013, Microbes and Infection 15:270-279) challenged mice with *Salmonella typhimurium* (intragastrically with 0.1 ml of a bacterial suspension containing $10^5$ CFU/ml) with or without prior administration of *S. boulardii*. Treatment with *S. boulardii* (a daily dose of 0.1 ml containing $10^9$ CFU/ml by oral gavage starting 10 days before infection and continued throughout the experiment) increased survival rate and inhibited translocation of bacteria after *S. typhimurium* challenge. Histological data showed that *S. boulardii* also protected mice against liver damage induced by *S. typhimurium*. Additionally, *S. boulardii* decreased levels of inflammatory cytokines and signal pathways involved in the activation of inflammation induced by *S. typhimurium*.

Collier et al (2011, J Anim Sci 89:52-58) tested the efficacy of *S. boulardii* to reduce mortality in pigs after an *E. coli* endotoxin challenge. Barrows were assigned to 1 of 2 treatment groups: with and without in-feed inclusion of *S. boulardii* (200 g/t) for 16 d. On d 16, all piglets were dosed via indwelling jugular catheters with LPS (25 µg/kg of BW) at 0 h. In *S. boulardii*-treated piglets, LPS-induced piglet mortality was reduced 20% compared with control piglets.

Pigs were also used by Daudelin et al (2011, Vet Res 42:69). At birth, different litters of pigs were randomly assigned to a control group and to a *S. boulardii* group. *S. boulardii* was administered daily ($1 \times 10^9$ CFU per pig) during the lactation period and after weaning (day 21). At 28 days of age, all pigs were orally challenged with an ETEC F4 strain, and a necropsy was performed 24 h later. Attachment of ETEC F4 to the intestinal mucosa was significantly reduced in pigs treated with *S. boulardii*.

Line et al (1998 Poultry Science 77:405-410) tested the effect of *S. boulardii* supplemented feed on *Salmonella* and *Campylobacter* population in broilers. Broiler chicks were given ad libitum access to a standard feed supplemented with no yeast (control), 1 g or 100 g dried *S. boulardii*/kg feed. All chicks except negative controls were challenged on day 4 with $3.2 \times 10^8$ CFU *S. typhimurium* and $6.5 \times 10^8$ CFU *C. jejuni* by oral gavage. After 3 wk, the broilers were euthanatized and ceca were aseptically removed and analyzed for *Salmonella* and *Campylobacter*. Frequency of *Salmonella* colonization was significantly (P<0.05) reduced due to yeast treatment. *Campylobacter* colonization however was not significantly affected.

For ethical, technical, regulatory, and cost reasons, in vitro methods are increasingly used as an alternative to in vivo experimentations. A non-limiting example is described in Fleury et al (2017 Appl Microbiol Biotechnol 101:2533-2547). The herein described in vitro model of the piglet colon, the PigutIVM, reproduces the main biotic and abiotic parameters of the piglet colon: temperature, pH, retention time, supply of ileal effluents, complex, and metabolically active microbiota and self-maintained anaerobiosis.

Hence, in a sixth aspect, a dietary supplement or pharmaceutical composition comprising a yeast strain is provided, wherein said yeast strain comprises a homozygous or hemizygous mutant WHI2 allele compromising, partially abolishing or completely abolishing Whi2 function. This is equivalent as saying that a dietary supplement or pharmaceutical composition comprising a yeast strain is provided, wherein said yeast strain comprises a disrupted, partially deleted or completely deleted WHI2 allele, wherein said WHI2 yeast allele is present in said yeast in a homozygous or hemizygous form. In one embodiment, said yeast is *Saccharomyces*, more preferably *S. cerevisiae*, even more preferably *S. cerevisiae* var. *boulardii*. In other embodiments, said WHI2 yeast allele comprises a nonsense or missense mutation on nucleic acid position 860, more particularly said WHI2 yeast allele is a whi2S270* allele or encodes a Whi2 protein comprising a S270* mutation, even more particularly said WHI2 yeast allele comprises a C860G mutation, most particularly said WHI2 yeast allele is the allele as depicted in SEQ ID No. 1. In other embodiments, said yeast is not the diploid *S. boulardii* strain Sb.P or Sb.A or not a Sb.P or Sb.A strain. In other embodiments, said yeast is a haploid segregant of a *S. boulardii* strain.

In a seventh aspect, a yeast strain comprising a homozygous or hemizygous mutant WHI2 allele compromising, partially abolishing or completely abolishing Whi2 function is provided for use as a medicament. Also the pharmaceutical composition comprising said yeast strain is provided for use as a medicament. In one embodiment, said yeast strain as well as said pharmaceutical composition is provided for use in the treatment or prevention of gastrointestinal disorders, more particularly for use in the treatment or prevention of diarrhea, for use in reducing gastrointestinal discomfort, increasing gastrointestinal comfort, improving immune health and/or relieving constipation. In another embodiment, the use of a yeast strain comprising a homozygous or hemizygous mutant WHI2 allele compromising, partially abolishing or completely abolishing Whi2 function is provided as a live probiotic additive to a food or feed product. In other particular embodiments of the seventh aspect, said yeast comprises a homozygous or hemizygous mutant WHI2 yeast allele comprising a nonsense or missense mutation on nucleic acid position 860, more particularly said WHI2 yeast allele is a whi2S270* allele or encodes a Whi2 protein comprising a S270* mutation, even more particularly said WHI2 yeast allele comprises a C860G mutation, most particularly said WHI2 yeast allele is the allele as depicted in SEQ ID No. 1.

Also, the use of the dietary supplement comprising a yeast strain comprising one of the mutant WHI2 yeast alleles of the application is provided for preparing a food supplement and/or a probiotic and/or a functional food and/or a nutraceutical and/or functional ingredients intended for human beings and/or for animals. Also, said dietary supplement is provided for preparing food compositions intended to improve gastrointestinal comfort and/or to improve intestinal flora.

In more particular embodiments, said yeast useful for probiotic use includes but is not limited to *Saccharomyces*, *Zygosaccharomyces*, Brettanomyces and *Kluyveromyces*. Preferably, said yeast is a *Saccharomyces* sp., even more preferably it is a *Saccharomyces cerevisiae* sp., most preferably it is a *S. cerevisiae* var. *boulardii*. In yet other particular embodiments, said yeast is a haploid segregant of a *S. boulardii* strain comprising one of the mutant WHI2 yeast alleles of the application. In even more particular embodiments of the seventh aspect, said yeast is not a diploid *S. boulardii* Sb.P or Sb.A or not a Sb.P or Sb.A strain.

"Probiotic" as used herein refers to any consumable yeast, more particularly a *Saccharomyces* yeast, most particularly a *S. boulardii* yeast that provides health benefits for humans and animals when consumed. Probiotics are considered to be generally safe and help restore the balance of intestinal flora, keep it stable by positively changing the composition of the intestinal flora of humans and animals and/or positively affect the part of the immune system, which communicates with the intestinal wall. Through the production of metabolites, such as acetic acid, lactic acid and hydrogen peroxide, probiotic microorganisms, for example, deteriorate the living conditions of undesirable microorganisms in the gut. The presence of probiotic microorganisms in the gut improves the digestion function and can both be used in a therapeutic set-up for example to treat gastrointestinal disorders as diarrhea or in a preventive set-up for example to maintain a well-balanced gut microbiome and gastrointestinal comfort. A "probiotic additive" or equivalently "probiotic supplement" is a substance in any shape or form that contains probiotics. More specifically, a probiotic substance can be dry or liquid and comprises live probiotics embedded in a matrix of sugars, proteins and/or polysaccharides. Hence, it may be a food product on its own.

The term "food or feed product" is intended to encompass any consumable matter of either plant or animal origin or of synthetic sources that contain a body of nutrients such as a carbohydrate, protein, fat vitamin, mineral, etc. The product is intended for the consumption by humans or by animals, such as domesticated animals, for example cattle, horses, pigs, sheep, goats, and the like. Pets such as dogs, cats, rabbits, guinea pigs, mice, rats, birds (for example chickens or parrots), reptiles and fish (for example salmon, tilapia or goldfish) and crustaceans (for example shrimp). The food product may be liquid or solid. It may include but is not limited to a liquid fermented solution such as milk or yoghurt. The feed product may include but is not limited to pelleted feeds or pet feed for example a snack bar, crunchy treat, cereal bar, snack, biscuit, pet chew, pet food, and pelleted or flaked feed for aquatic animals.

"Functional food" as used herein is a food given an additional function (often one related to health-promotion or disease prevention) by adding new ingredients for example a probiotic or more of existing ingredients. A "nutraceutical" is a pharmaceutical-grade and standardized nutrient that provides medical or health benefits including the prevention and/or treatment of a disease. A "dietary supplement" is a non-nutrient chemical with a biologically beneficial effect. Supplements as generally understood include vitamins, minerals, fiber, fatty acids, or amino acids, among other substances.

In an eight aspect, the use of a disrupted, partially deleted or completely deleted WHI2 yeast allele to develop an acetic acid producing yeast is provided. In one embodiment, said WHI2 yeast allele comprises a nonsense or missense mutation on nucleic acid position 860, more particularly said WHI2 yeast allele is a whi2S270* allele or encodes a Whi2 protein comprising a $270* mutation, even more particularly said WHI2 yeast allele comprises a C860G mutation, most particularly said WHI2 yeast allele is the allele as depicted in SEQ ID No. 1.

Also, the use is provided of a yeast strain comprising a disrupted, partially deleted or completely deleted WHI2 yeast allele for the production of acetic acid or of a yeast strain comprising any of the mutant WHI2 yeast alleles described in this application. In particular embodiments, said yeast is useful for acetic acid production, including, but not limited to *Saccharomyces, Zygosaccharomyces*, Brettanomyces and *Kluyveromyces*. Preferably, said yeast is a *Saccharomyces* sp., even more preferably it is a *Saccharomyces cerevisiae* sp., most preferably it is a *S. cerevisiae* var. *boulardii*. In yet other particular embodiments, said yeast is a haploid segregant of a *S. boulardii* strain comprising one of the mutant WHI2 yeast alleles of the application. In even more particular embodiments of the eight aspect, said yeast is not a diploid *S. boulardii* Sb.P or Sb.A or not a Sb.A or Sb.P strain.

In an ninth aspect, a method of treating or preventing gastrointestinal disorders, more particularly diarrhea in a human or animal or of maintaining or improving the health of the gastrointestinal tract in a human or animal is provided, said method comprising administering to said human or animal a dietary supplement or pharmaceutical composition, wherein said dietary supplement or pharmaceutical composition comprises a yeast strain comprising any of the mutant WHI2 yeast alleles from the application. In other embodiments, said maintaining or improving the health of the gastrointestinal tract comprises reducing the number of pathogenic bacteria found in the faeces of said human or animal. In more particular embodiments, said pathogenic bacteria are selected from the group consisting of Clostridia, *Escherichia, Salmonella, Shigella* and mixtures thereof.

The probiotic yeast of this application must arrive in large number in the gut in order to settle there, and must not be destroyed by stomach acid as it passes the stomach. Therefore, in particular embodiments, said dietary supplement or pharmaceutical composition comprises a therapeutically effective amount of said yeast strains. In more particular embodiments, said therapeutically effective amount is an amount of more than $10^6$ CFU (colony forming units), or of more than $10^7$ CFU, or of more than $10^8$ CFU or of more than $10^9$ CFU of said yeast per gram or per ml of said supplement or composition, or comprises between $10^5$ and $10^{15}$ CFU, or between $10^6$ and $10^{12}$ CFU, or between $10^7$ and $10^{11}$ CFU, or between $10^8$ and $6\times10^{10}$ CFU, or between $10^9$ and $2\times10^{10}$ CFU of said yeast per gram or per ml of said supplement or composition.

The methods of this application are both for treating and preventing gastrointestinal disorders. Indeed, administration of certain live probiotic yeasts can help restore optimal intestinal flora in animals such as cattle, especially after stressful situations such as transport to a feedlot (Gedek, B., "Probiotics in Animal Feeding—Effects on Performance and Animal Health," Feed Magazine, November 1987) but regular administration of probiotics also increase nutrient absorption efficiency and help control the proliferation of harmful microorganisms in the animals' digestive tracts that could otherwise cause disease conditions adversely affecting rates of animal development and weight gain.

In particular embodiments, said yeast useful for probiotic use includes but is not limited to *Saccharomyces, Zygosaccharomyces*, Brettanomyces and *Kluyveromyces*. Preferably, said yeast is a *Saccharomyces* sp., even more preferably it is a *Saccharomyces cerevisiae* sp., most preferably it is a *S. cerevisiae* var. *boulardii*. In yet other particular embodiments, said yeast is a haploid segregant of a *S. boulardii* strain comprising one of the mutant WHI2 yeast alleles of the application. In even more particular embodiments of the ninth aspect and of all its embodiments, said yeast is not a diploid *S. boulardii* Sb.P or Sb.A or not a Sb.P or Sb.A strain.

We have also identified and isolated a *S. boulardii* mutant allele from the SDH1 gene that when expressed homozygously in industrial *S. cerevisiae* strains or when expressed in the absence of a wild-type (and thus fully functional) SDH1 gene increases the production of acetic acid. The mutant allele comprises a mutated nucleic acid at position 950 of the open reading frame sequence depicted in SEQ ID No. 2, wherein said mutation is a missense mutation resulting in a non-functional Sdh1 protein.

In one aspect, a mutant SDH1 yeast allele is provided comprising a missense mutation on nucleic acid position 950. In one embodiment, said mutant SDH1 yeast allele is an isolated mutant SDH1 yeast allele. In particular embodiments, said SHD1 mutant allele is the sdh1F317Y allele or encodes an Sdh1 protein comprising a F317Y mutation. In more particular embodiments, said SDH1 allele comprises a T950A mutation. In most particular embodiments, said SDH1 mutant allele is the allele as depicted in SEQ ID No. 2. In the rest of this document, the above described mutant SDH1 yeast alleles will be referred to as "the mutant SDH1 alleles of the application".

"Position 950" as used herein refers to the nucleobase that is 949 positions removed downstream from the first nucleobase (i.e. adenosine) from the start codon. This position is indicated in SEQ ID No. 2 by underlining.

"SDH1" or "Sdh1" as used herein refers to the SUCCINATE DEHYDROGENASE1 gene or Succinate dehydrogenase1 protein respectively of *Saccharomyces*. The SDH1 gene is depicted in SEQ ID No. 6 and the Sdh1 protein is depicted in SEQ ID No.7. The mutant SDH1 allele which is disclosed in this application is depicted in SEQ ID No. 2. SDH1 is also known in the art as SDHA or YKL148C (SGD ID: S000001631, Chromosome XI 169207 . . . 171129).

In another aspect, a yeast strain is provided comprising a mutant SDH1 yeast allele, wherein said allele comprises a missense mutation on nucleic acid position 950 or wherein said SDH1 allele is the sdh1F317Y allele or wherein said SDH1 allele encodes an Sdh1 protein comprising a F317Y mutation or wherein said SDH1 allele comprises a T950A mutation or wherein said SDH1 allele is the allele as depicted in SEQ ID No. 2. In particular embodiments, said mutant SDH1 yeast allele is present in said yeast in a homozygous or hemizygous form. In particular embodiments, said homozygous or hemizygous mutant SDH1 allele deprives said yeast from growing on acetic acid, particularly at 37° C., even more particularly in aerobic conditions. This is equivalent as saying that a yeast is providing which is growth deficient on acetic acid particularly at 37° C., even more particularly in aerobic conditions, because of the presence of a homozygous or hemizygous SDH1 mutant allele, wherein said SDH1 mutant allele is any of the SDH1 mutant alleles of this application. In particular embodiments, said yeast strain is particularly useful for probiotic applications or for acetic acid production. More particularly said yeast strain is a *Saccharomyces* yeast, even more particularly a *S. cerevisiae*. In most particular embodiments, said yeast is not a diploid *S. boulardii* strain or not a *S. boulardii* strain.

In another aspect, a haploid segregant of a *Saccharomyces boulardii* strain is provided comprising a disrupted, partially deleted or completely deleted SDH1 allele. Said SDH1 allele thus encodes a non-functional Sdh1 protein and comprises one or more mutations which can be frame shift mutations, nonsense mutations or missense mutations. In particular embodiments, said SDH1 allele comprises a missense mutation on nucleic acid position 950 or said SDH1 allele is the sdh1F317Y allele or said SDH1 allele encodes an Sdh1 protein comprising a F317Y mutation or said SDH1 allele comprises a T950A mutation or said SDH1 allele is the allele as depicted in SEQ ID No. 2. In one embodiment, a dietary supplement or a pharmaceutical composition is provided comprising said haploid segregant.

In another aspect, a dietary supplement or a pharmaceutical composition is provided comprising a yeast strain comprising a disrupted, partially deleted or completely deleted SDH1 allele, wherein said strain is not a diploid *S. boulardii* strain or wherein said yeast strain is a non *S. boulardii* yeast. In particular embodiments, said SDH1 allele comprises a missense mutation on nucleic acid position 950 or said SDH1 allele is the sdh1F317Y allele or said SDH1 allele encodes an Sdh1 protein comprising a F317Y mutation or said SDH1 allele comprises a T950A mutation or said SDH1 allele is the allele as depicted in SEQ ID No. 2.

In yet another aspect, a yeast strain is provided comprising a disrupted, partially deleted or completely deleted SDH1 allele or comprising a SDH1 allele comprising a missense mutation on nucleic acid position 950 or a SDH1 allele which is the sdh1F317Y allele or a SDH1 allele encoding an Sdh1 protein comprising a F317Y mutation of a SDH1 allele comprising a T950A mutation or a SDH1 allele as depicted in SEQ ID No. 2, for use as a medicament, wherein said yeast is not a diploid *S. boulardii* strain. In a particular embodiment, said SDH1 allele is present in said yeast strain in a homozygous or hemizygous form. In another embodiment, said yeast strain is a non *S. boulardii* yeast. Also a pharmaceutical composition comprising said yeast strain is provided for use as a medicament. In more particular embodiments, said yeast strain or said pharmaceutical composition is provided for use in the treatment or prevention of gastrointestinal disorders, including but not limited to treatment or prevention of diarrhea, reducing gastrointestinal discomfort, increasing gastrointestinal comfort, improving immune health, relieving constipation.

In another aspect, the use of a yeast strain comprising a disrupted, partially deleted or completely deleted SDH1 allele is provided as a live probiotic additive to foodstuff and/or feedstuff, wherein said yeast is not a diploid *S. boulardii* strain or wherein said yeast is a non *S. boulardii* yeast. In one embodiment, said SDH1 allele comprises a missense mutation on nucleic acid position 950 or said SDH1 allele is the sdh1F317Y allele or said SDH1 allele encodes an Sdh1 protein comprising a F317Y mutation or said SDH1 allele comprises a T950A mutation or said SDH1 allele is depicted in SEQ ID No. 2.

In another aspect, the use of a yeast strain comprising a mutant SDH1 allele is provided for the production of acetic acid, wherein said mutant SDH1 allele is a disrupted, partially deleted or completely deleted SDH1 allele or wherein said SDH1 allele comprises a missense mutation on nucleic acid position 950 or wherein said SDH1 allele is the sdh1F317Y allele or wherein said SDH1 allele encodes an Sdh1 protein comprising a F317Y mutation or wherein said SDH1 allele comprises a T950A mutation or wherein said SDH1 allele is depicted in SEQ ID No. 2. In one embodiment said SDH1 allele is homozygously or hemizygously present in said yeast. In another aspect, the use of a mutant SDH1 yeast allele is provided to develop an acetic acid producing yeast, wherein said mutant SDH1 allele is a disrupted, partially deleted or completely deleted SDH1 allele or wherein said SDH1 allele comprises a missense mutation on nucleic acid position 950 or wherein said SDH1 allele is the sdh1F317Y allele or wherein said SDH1 allele encodes an Sdh1 protein comprising a F317Y mutation or wherein said SDH1 allele comprises a T950A mutation or wherein said SDH1 allele is depicted in SEQ ID No. 2.

In another embodiment, a method of treating or preventing gastrointestinal disorders, more particularly diarrhea in a human or animal or of maintaining or improving the health of the gastrointestinal tract in a human or animal is provided, said method comprising administering to said human or animal a dietary supplement or pharmaceutical composition, wherein said dietary supplement or pharmaceutical composition comprises a yeast strain comprising a mutant SDH1 yeast allele, wherein said mutant SDH1 allele is a disrupted, partially deleted or completely deleted SDH1 allele or wherein said SDH1 allele comprises a missense mutation on nucleic acid position 950 or wherein said SDH1 allele is the sdh1F317Y allele or wherein said SDH1 allele encodes an Sdh1 allele comprising a F317Y mutation or wherein said SDH1 allele comprises a T950A mutation or wherein said SDH1 allele is depicted in SEQ ID No. 2 and wherein said yeast is not a diploid *S. boulardii* strain or more particularly wherein said yeast is a non *S. boulardii* yeast. In other embodiments, said maintaining or improving the health of the gastrointestinal tract comprises reducing the number of pathogenic bacteria found in the faeces of said human or animal. In more particular embodiments, said pathogenic bacteria are selected from the group consisting of Clostridia, *Escherichia*, *Salmonella*, *Shigella* and mixtures thereof.

The probiotic yeast of this application must arrive in large numbers in the gut in order to settle there, and must not be destroyed by stomach acid as it passes the stomach. Therefore, in particular embodiments, said dietary supplement or pharmaceutical composition comprises a therapeutically effective amount of said yeast strains. In more particular embodiments, said therapeutically effective amount is an amount of more than $10^6$ CFU (colony forming units), or of more than $10^7$ CFU, or of more than $10^8$ CFU or of more than $10^9$ CFU of said yeast per gram or per ml of said supplement or composition, or comprises between $10^5$ and $10^{15}$ CFU, or between $10^6$ and $10^{12}$ CFU, or between $10^7$ and $10^{11}$ CFU, or between $10^8$ and $6\times10^{10}$ CFU, or between $10^9$ and $2\times10^{10}$ of said yeast per gram or per ml of said supplement or composition.

In particular embodiments, said yeast is useful for probiotic use including, but not limited to *Saccharomyces*, *Zygosaccharomyces*, Brettanomyces and *Kluyveromyces*. Preferably, said yeast is a *Saccharomyces* sp., even more preferably it is a *Saccharomyces cerevisiae* sp. In yet other particular embodiments, said yeast is a haploid segregant of a *S. boulardii* strain comprising one of said mutant SDH1 yeast alleles of the application. In even more particular embodiments of the seventh aspect, said yeast is not a diploid *S. boulardii* or is a non *S. boulardii* yeast.

In particular embodiments of all above aspects and of all its embodiments, said yeast is an engineered or recombinant yeast and said *S. boulardii* is an engineered or recombinant *S. boulardii*.

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Example 1: Classification of S. boulardii and S. cerevisiae Strains Using Amplified Fragment Length Polymorphisms (AFLPs)

S. boulardii strains obtained from various sources (Table 1) were characterised alongside 23 S. cerevisiae strains as well as two strains from different Saccharomyces species (S. mikatae and S. paradoxus), using Amplified Fragment Length Polymorphisms (AFLPs). The results revealed that all S. boulardii strains formed a single cluster of highly related strains (FIG. 1). Furthermore, this cluster of S. boulardii strains was embedded within a larger S. cerevisiae cluster that was only distantly related to the two other Saccharomyces species employed in this study. These results confirm that S. boulardii and S. cerevisiae are very closely related and likely belong to a single species.

TABLE 1

Strains used in this study

| Strains | Source | Genotype |
|---|---|---|
| S. boulardii | | |
| UL[24,27] | Lubomira Stateva, University of Manchester, UK | Wild type |
| Sb.L, LSB, Sb.P, 7135, 7136, 259, 7103, and Sb.A[18,59] | Lene Jespersen, University of Copenhagen, Denmark | Wild type |
| ENT [this study] | Isolated from Pharmacy product Enterol ® | Wild type |
| SAN [this study] | Isolated from Pharmacy product Sanifort ® | Wild type |
| FLO [this study] | Isolated from Pharmacy product Floratil ® | Wild type |
| S. cerevisiae | | |
| Ethanol Red[100], VR-1[101], PE-2[83], CAT-1[86], S47[102], CBS 1585[47], CBS6412[40], MUCL 28177[45] JT 22689[this study], ATCC 38555[103], 5288c[104] | MCB collection | Wild type |
| Constructed in this study | | |
| Sb.Paa | Sb.P with homozygous MAT locus | MATa/a |
| ERαα | ER with homozygous MAT locus | MATα/α |
| SBERT8 | Sb.Paa/ERαα tetraploid hybrid | MATa/α |
| SBERT3C | Diploid segregant of SBERT8 | MATa/α |
| SBERH6 | Haploid segregant of SBERT3C | MATα |
| Bacterial indicator strain | | |
| E. coli MG1655[105,106] | Abram Aertsen, University of Leuven, Belgium | (F⁻rph-1) |

Figure 2A:
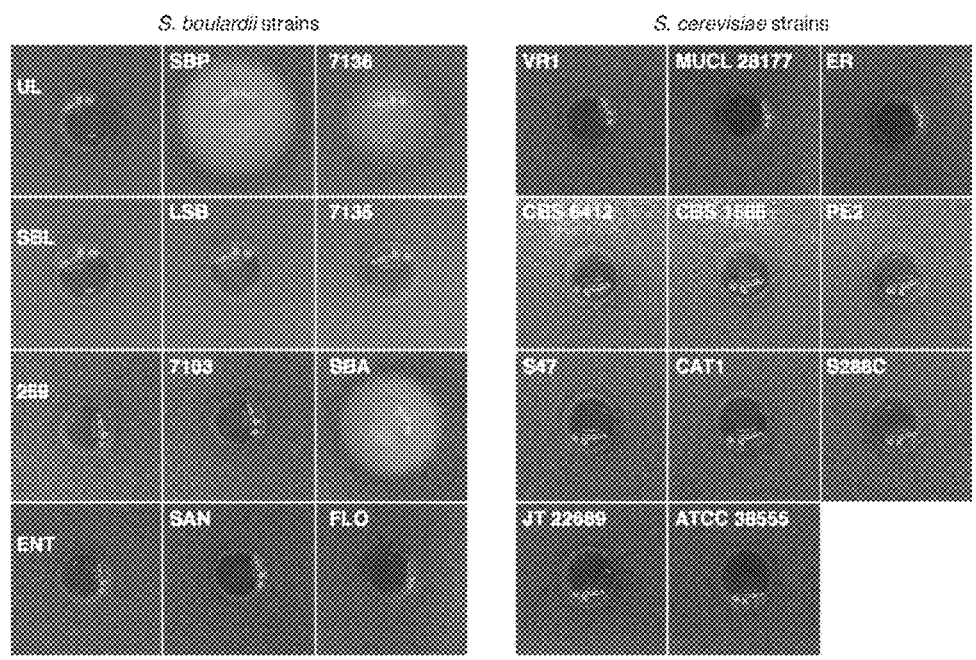
FIG. 2. *S. boulardii* produces acetic acid levels with antibiotic action. A. Agar-well diffusion assay for assessment of antibacterial activity in cell-free culture supernatants from *S. boulardii* strains (left panel) and *S. cerevisiae* strains (right panel), visualized with plates containing *E. coli* MG1655 as indicator strain; B. HPLC chromatograms of cell-free culture supernatants from Sb.P (*S. boulardii*) and ER (*S. cerevisiae*) compared with the 2% acetic acid standard. Insets: antibacterial agar-well diffusion assay using *E. coli* MG1655 as indicator; C. Acetic acid accumulation profile of wild type *S. boulardii* (Sb.P, Sb.A, 7136, 259, UL, SAN) and *S. cerevisiae* strains (MUCL 28177, ER, VR-1, JT22689, CAT-1, ATCC 38555). D. Effect of temperature on potassium acetate growth. Spot assay on YPD (2%) and YPAc (1%, pH 5) for SBERH6 and *S. boulardii* stains Sb.P and Sb.A, capable of accumulating acetic acid versus *S. boulardii* strains lacking the capacity for acetic acid accumulation, ENT and Sb.L. Cells were diluted 10-fold from OD600: 0.5. At 37° C., Sb.P, SBERH6 and Sb.A showed reduced growth on YPAc compared to Sb.L and ENT. While no large differences in growth were observed on YPD or at 30° C.

Example 2: Evaluation of S. boulardii for Antimicrobial Activity in Comparison with S. cerevisiae We have assessed the potential for antimicrobial compound production of all S. boulardii strains in our collection in comparison with S. cerevisiae by the agar-well diffusion method using E. coli MG1655 as indicator strain. For that purpose, the strains were propagated in YPD at 37° C. for 48 h and the cell-free culture supernatant, obtained by centrifugation, was used for the assay. Out of 12 S. boulardii and 11 S. cerevisiae cell-free culture supernatants tested, those obtained from S. boulardii strains Sb.P and Sb.A produced a clear inhibition zone (FIG. 2A). No zones of inhibition were observed with cell-free culture supernatants obtained from any of the S. cerevisiae strains included in this study.

Example 3: Identification of the Antimicrobial Agent Secreted by S. boulardii

Figure 2B:
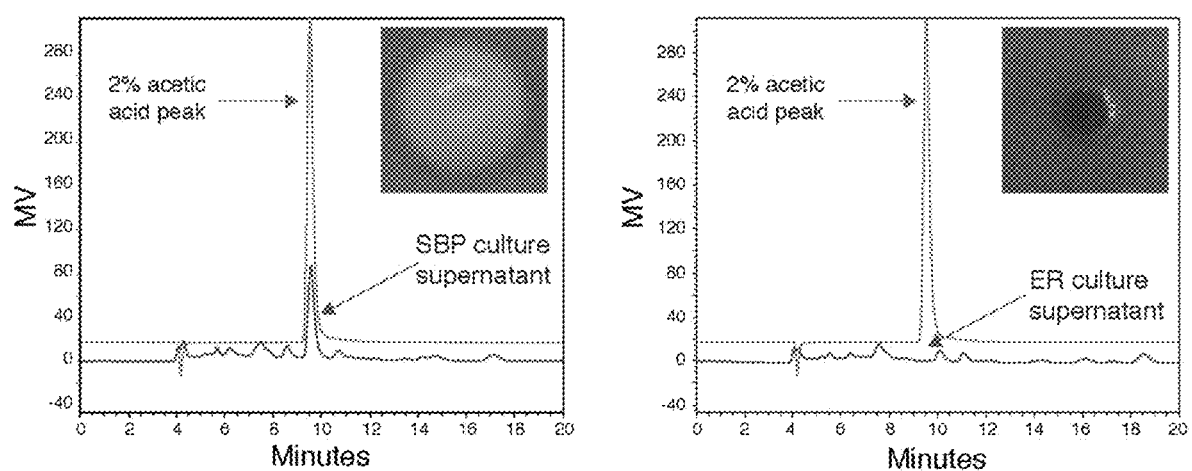

In an attempt to define the biochemical nature of the antimicrobial agent secreted by S. boulardii, the cell-free culture supernatant from the Sb.P strain was submitted to different assays. First, it was subjected to 80% ammonium sulphate precipitation. A solution made with the ammonium sulphate precipitate did not yield a zone of inhibition in the agar-well diffusion assay and the antimicrobial activity completely remained in the supernatant. The results discarded any possibility of the antimicrobial agent being proteinaceous in nature. Second, the cell-free culture supernatant of S. boulardii Sb.P showed a significantly lower pH of 4.2 compared to a pH of 5.3 for the culture supernatants of the S. cerevisiae strains and the other S. boulardii strains. Furthermore, addition of NaOH to the Sb.P cell-free culture supernatant, to bring the final pH to 5.3, abolished its potent antimicrobial action. These results suggested that the secreted compound could be an organic acid. Subsequently, we subjected a cell-free culture supernatant from S. boulardii Sb.P as well as that of a control S. cerevisiae strain Ethanol Red (ER), that did not inhibit E. coli MG1655 (FIG. 2A), to HPLC analysis. Five organic acids, succinic acid, lactic acid, propanoic acid, acetic acid and methanoic acid, were used as standards, each at a concentration of 2% (v/v). The chromatogram obtained with the cell-free culture supernatant from the Sb.P strain revealed a prominent peak with the same retention time as acetic acid. On the other hand, no such peak was observed when testing the cell-free culture supernatant from the ER strain (FIG. 2B).

Figure 2C:
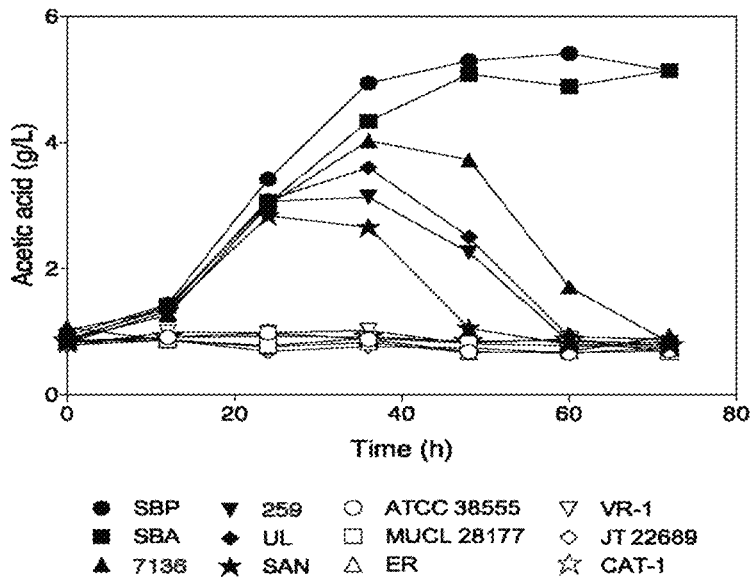
Figure 3:
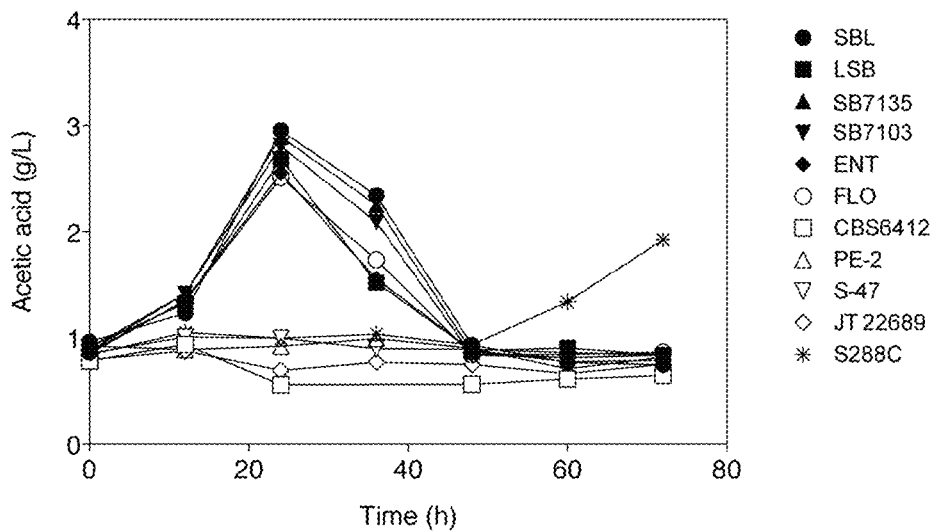
FIG. 3. Acetic acid accumulation profile of wild type *S. boulardii* and *S. cerevisiae* strains. *S. boulardii* (Sb.L, LSB, 7135, 7103, ENT, FLO), *S. cerevisiae* (CBS 6412, PE-2, S-47, JT 22689, S288c).

Next, we performed time-course measurements of acetic acid production during growth of the cultures, taking samples at 12 h intervals over a 72 h period. This was performed to investigate whether acetic acid secretion was unique to the S. boulardii Sb.P and Sb.A strains or whether it was at least to some extent also present in the other S. boulardii strains. For this purpose, the cells were grown aerobically at 37° C. The results showed that all S. boulardii strains displayed high acetic acid production roughly to the same extent after 24 h of growth with a mean acetic acid yield of 2.9 g/l±0.25 SD (FIG. 3). However, the level of acetic acid started to decline after 36 h of growth for all strains except for S. boulardii Sb.P and Sb.A (FIG. 2C). Acetic acid accumulation in those two strains continued until 48 h when the maximum acetic acid level was obtained (5.30 g/l for Sb.P and 5.10 g/l for Sb.A). Acetic acid accumulation remained constant for both strains until the end of the experiment. Apparently, the S. boulardii strains are able to consume again the acetic acid they have produced, with exception of Sb.P and Sb.A, explaining their much higher potency in the antibacterial assay. The strain Sb.P showed the highest acetic acid production profile among all the S. boulardii strains studied. The S. cerevisiae strains included in this study did not display high acetic acid production to any appreciable extent. The results for six *S. boulardii* strains alongside six *S. cerevisiae* strains are shown in FIG. 2C.

Figure 2D:
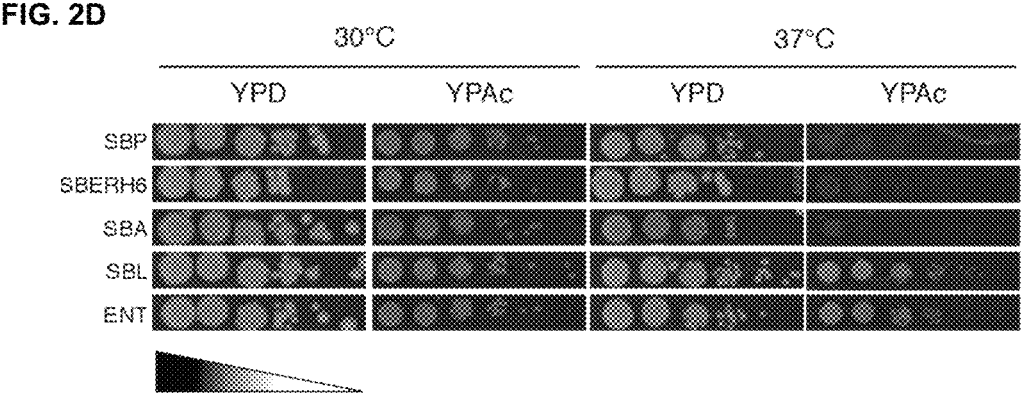

Example 4: Assessment of Selected *S. boulardii* Strains for Growth on Acetic Acid Since the two *S. boulardii* strains with the highest acetic acid accumulation capacity, Sb.P and Sb.A, were apparently unable to consume acetic acid, as opposed to the other *S. boulardii* strains, we assessed growth capacity on acetic acid of Sb.P, Sb.A and two other *S. boulardii* strains, ENT and Sb.L. The results showed that none of the *S. boulardii* strains are deficient for growth on acetic acid at 30° C. but that the Sb.P and Sb.A strains are specifically deficient for growth on acetic acid at 37° C. (FIG. 2D). This confirms that the high acetic acid accumulation capacity of these two strains is a temperature dependent probiotic property that is only manifested at the human body temperature.

Figure 4A:
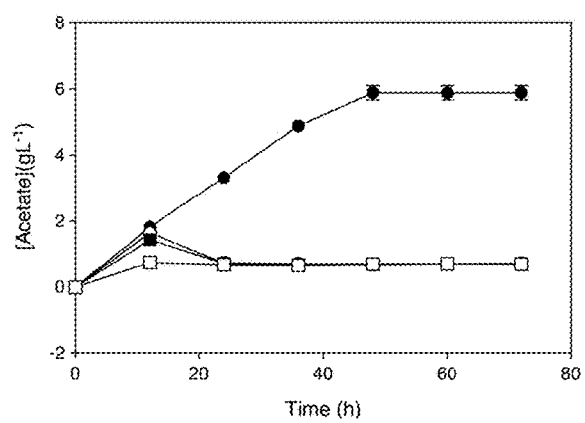
FIG. 4. Effect of acetic acid accumulation on medium pH, cell growth and viability in *S. boulardii* strains. *S. boulardii* strains Sb.P (•), Sb.L (■) and ENT (○) and one *S. cerevisiae* strain, ER (□) were propagated at 37° C. for 72 h. A. Acetic acid accumulation profile. B. Medium acidification. C. Cell growth as measured by OD600 and D. Cell survival as measured by oxonol staining.
Figure 4B:
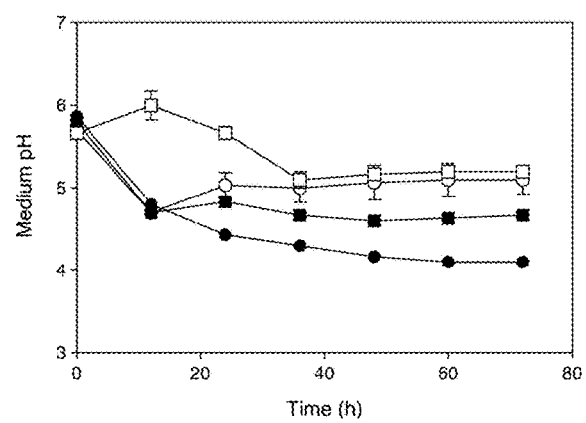
Figure 4C:
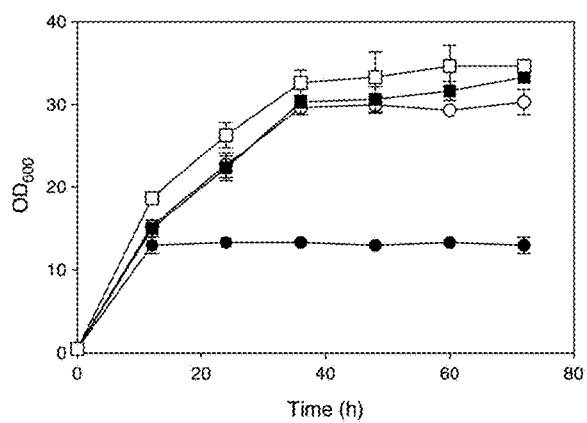
Figure 4D:
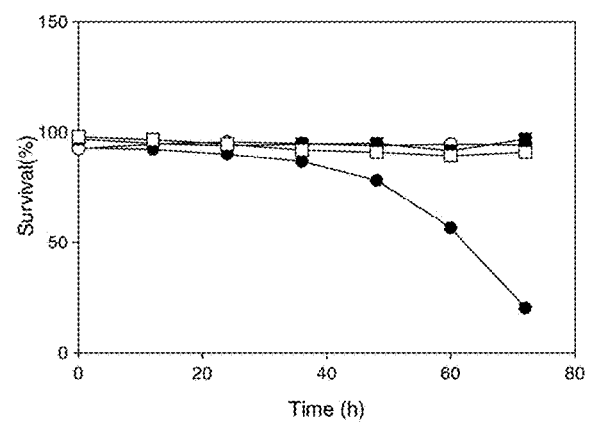

Example 5: Acetic Acid Accumulation and its Effects on Cell Proliferation and Cell Viability The effect of acetic acid accumulation on *S. boulardii* cell proliferation and viability was analysed next. It was accomplished by propagating three *S. boulardii* strains (Sb.P, Sb.L, and Enterol) alongside one *S. cerevisiae* strain (ER) at 37° C. and withdrawing samples at 12 h intervals. Biomass increment, cell viability, acetic acid concentration and pH were determined at each time-point (FIG. 4). The level of acetic acid production in those strains confirmed the previous results. Also, the accumulation of acetic acid closely correlated with the quasi-linear decrease in medium pH from approximately 6 to 4.2 over a period of 72 h. On the contrary, pH values in the cultures of the remaining strains only declined by about 1 pH unit within the same time period, which corresponds to values normally observed for stationary phase yeast cultures. Interestingly, biomass and cell viability measurements indicated that even at high acetic acid levels produced, Sb.P remained metabolically active. Indeed, even at concentrations of 2 g/l acetic acid or more, the Sb.P strain maintained acetic acid production. With increasing acetic acid accumulation cell division progressively decreased and ultimately at an acetic acid concentration of 5-6 g/l cell death was observed (FIG. 4C-D), which resulted for strain Sb.P in a low cell viability of 20% at the end of the incubation period. The strains Sb.L, Enterol and ER displayed because of their low acetic acid accumulation typical growth curves for yeast, entering stationary phase after 36 h of incubation (FIG. 4C) and showing cell viability levels near 100% (FIG. 4D).

Figure 5B:
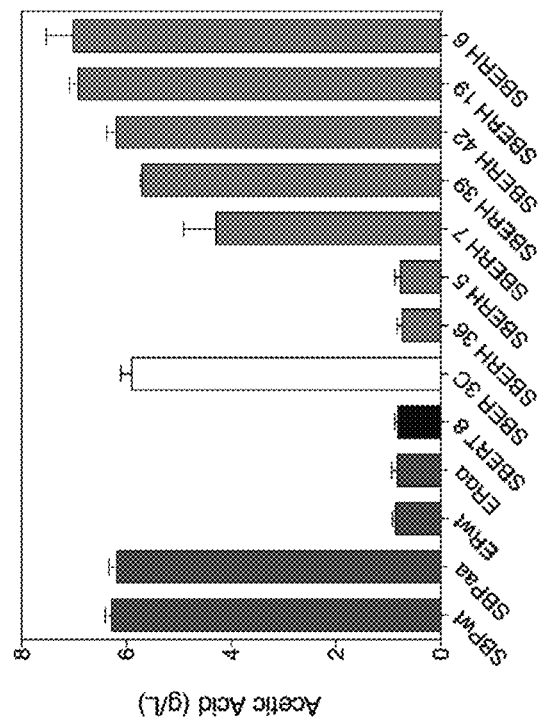
FIG. 5. Origin of the superior haploid parent strain SBERH6 and phenotyping of its progenitors and segregants after crossing with the inferior parent strain. A. Breeding scheme used to obtain the superior haploid strain SBERH6; B. Acetic acid production level of various progenitor strains in the breeding scheme used to generate strain SBERH6. All SBERH strains are segregants of SBER3C; C. Acetic acid production level of segregants selected for the superior pool (left panel) and inferior pool (right panel). The superior parent strain SBERH6 (SP), the inferior parent strain S288c (IP) and the hybrid diploid strain SBERH6/S288c (SP/IP) have been included as controls.
Figure 5A:
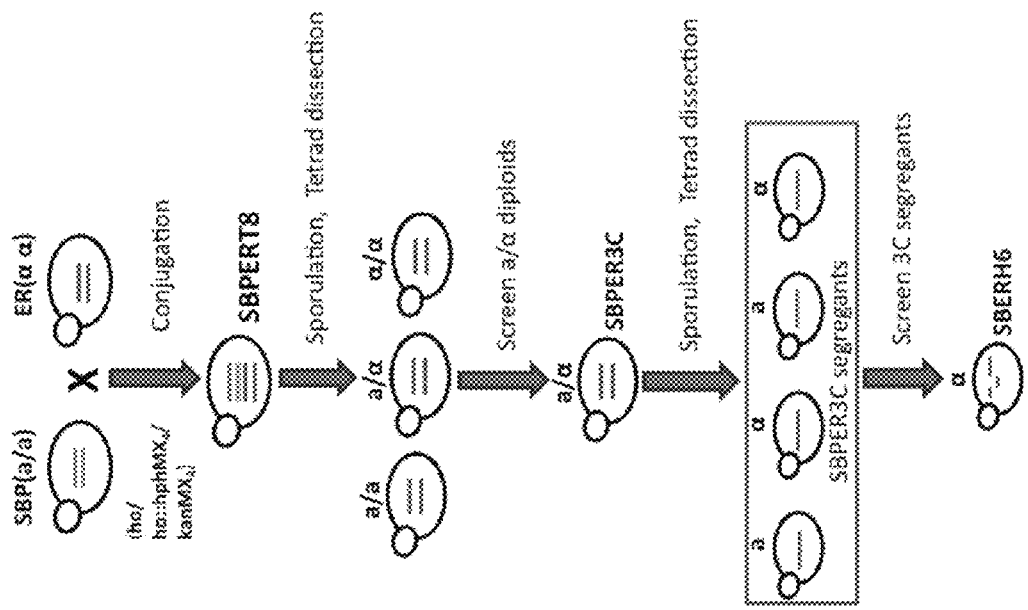
Figure 5C:
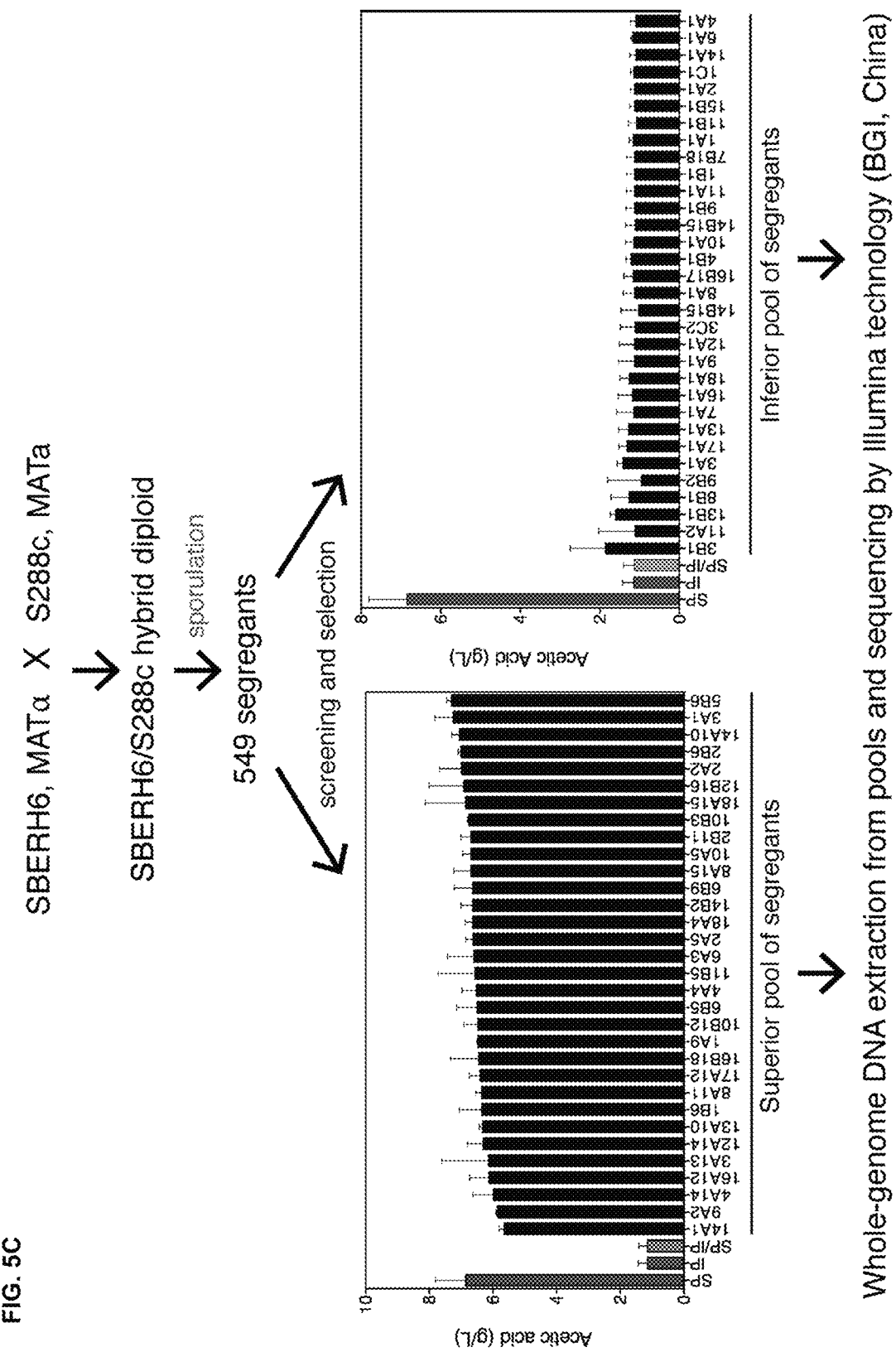

Example 6: Elucidation of the Genetic Basis for High Acetic Acid Production by QTL Mapping and Causative Gene Identification Because it showed the strongest acetic acid production and antibacterial activity, the *S. boulardii* Sb.P strain was selected for dissecting the polygenic basis behind this probiotic trait. A prerequisite for applying pooled-segregant whole-genome sequence analysis and causative gene identification is the isolation of a superior, mating-competent, haploid segregant that exhibits the trait of interest at least to a similar extent as its diploid (or polyploid) parent. To circumvent the inability of *S. boulardii* to sporulate, we generated a tetraploid hybrid by crossing an Sb.P MATα/α strain with an *S. cerevisiae* ER MATα/α strain. This was achieved by first deleting both copies of the HO endonuclease gene in the *S. boulardii* Sb.P strain, since this strain is homothallic. We then expressed the HO gene in a controlled way in the Sb.P hoΔ/Δstrain and also in the diploid *S. cerevisiae* ER strain to obtain two diploid strains homozygous at the MAT locus, MATα/MATa and MATα/MATa for Sb.P and ER, respectively. As a consequence, we were able to obtain subsequently a tetraploid strain (SBPERT8) by crossing these two mating-competent diploid strains. The SBPERT8 strain was competent for sporulation. We then screened one-hundred and forty-five diploid segregants from SBPERT8 for high acetic acid production at 37° C. and obtained SBPER3C, a diploid a/a strain with a similar level of acetic acid production as the original *S. boulardii* Sb.P strain. SBPER3C (MATα/a) was then sporulated and the segregants screened for high acetic acid production at 37° C. (FIG. 5A). The strain SBERH6 was identified as the segregant with the highest acetic acid production (7 g/l), again comparable to the acetic acid production of the original *S. boulardii* Sb.P strain (FIG. 5B). SBERH6 was also unable to grow on acetic acid at 37° C. but not at 30° C. (FIG. 2D). The ploidy of all strains constructed or isolated was confirmed by measuring their DNA content using flow cytometry. The high acetic acid-producing haploid segregant selected, SBERH6 (MATα), was used as the superior parent in a cross with an inferior parent, for which the prototrophic laboratory strain, S288c (MATα) was chosen. The hybrid diploid (SBERH6/S288c) obtained did not display the phenotype of high acetic acid production at 37° C. (FIG. 5C). It displayed good sporulation efficiency, but showed after tetrad dissection only moderate spore viability of about 50%. Out of 549 segregants from the hybrid diploid (SBERH6/S288c), 32 exhibited similar levels of acetic acid production at 37° C. to the superior parent (SBERH6) and were selected for inclusion in the superior pool. The same number of segregants, producing similarly low levels of acetic acid at 37° C. as the inferior parent S288c, was selected for inclusion in the inferior pool (FIG. 5C).

Figure 6A:
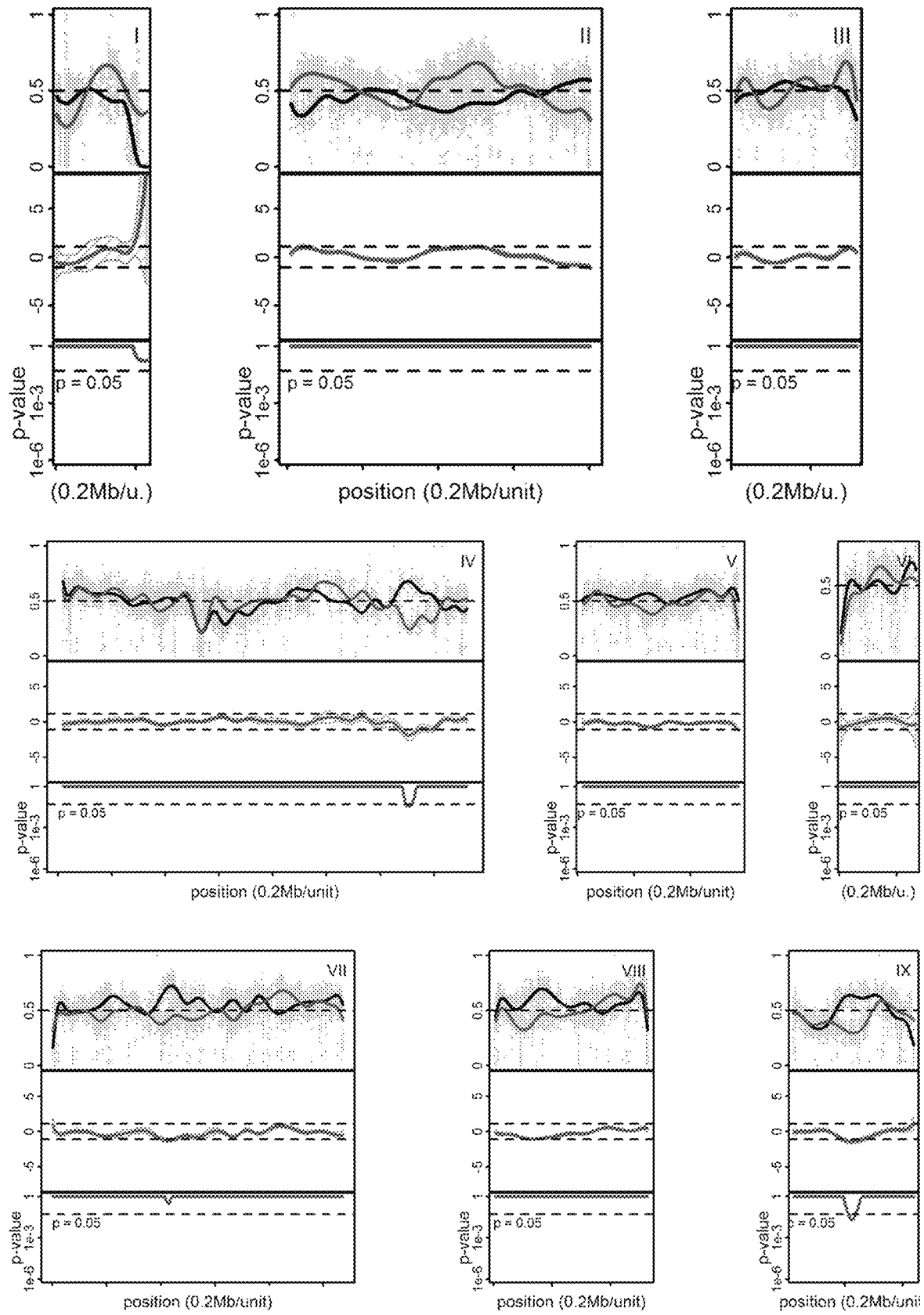
FIG. 6. QTL mapping with SNPs as genetic markers. Plots of SNP variant frequency from superior and inferior pools versus chromosomal position (raw data: dots; smoothed data: lines). The line in the middle graph indicates deviation from the confidence interval. P-values ≤0.05 for the difference between the smoothed lines of superior and inferior pools at a particular locus indicates statistically significant linkage to the genome of the superior or inferior parent at that locus. A major QTL with maximal linkage is present in the first half of chromosome XI while several minor QTLs with weak, but significant linkage are present in chromosomes IV, IX, XV and XVI.
Figure 6B:
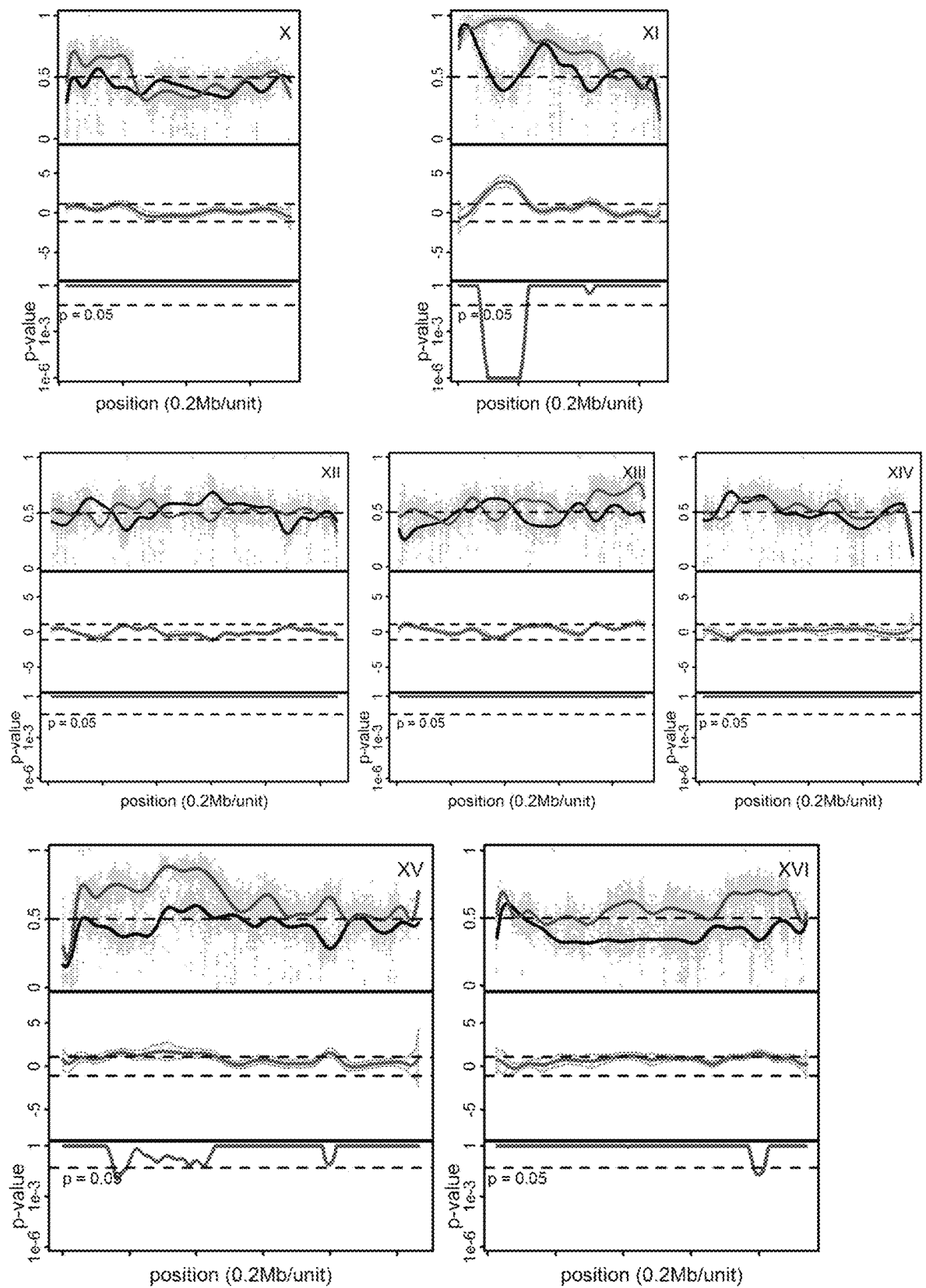

Equal quantities of cell biomass of the superior parent SBERH6 and from the segregants in each pool were combined, subjected to genomic DNA extraction and were sequenced using Illumina HiSeq2000 technology (BGI, Hong Kong, China). The sequence reads were mapped to the S288c reference sequence and variants were identified and filtered using the NGSEP pipeline[48] and CLC genomic workbench (CLC Bio-Qiagen, Aarhus, Denmark). The genomic DNA from the superior pool yielded 6,329,693 paired reads, which resulted in a 97.19% overall alignment rate with the S288c sequence, whilst 6,328,957 paired reads obtained from the genomic DNA of the inferior pool achieved a 96.2% alignment rate. Single Nucleotide Variant (SNV) frequencies deviating upwards from 50% in the superior pool indicated linkage to the high acetic acid phenotype. Plotting the SNV frequency (y-axis) versus the SNP chromosomal position (x-axis) for each chromosome revealed several QTLs linked to the genome of the superior parent strain, SBERH6, including two major QTLs, QTL1 in chromosome XI (NC_001143.9:g. 31118 . . . 231737), QTL2 in chromosome XV and minor QTL3 in chromosome XVI (FIG. 6). In two other minor QTLs, on chromosome IV and IX, the genome of the inferior parent strain, S288c, was linked to the high acetic acid phenotype. In this paper, we have concentrated on the further analysis of the genes within QTL1 and QTL2, for the trait of high acetic acid production in the *S. boulardii* Sb.P strain.

Example 7: Analysis of QTL1 by Bulk Reciprocal Hemizygosity Analysis (bRHA)

Figure 7A:
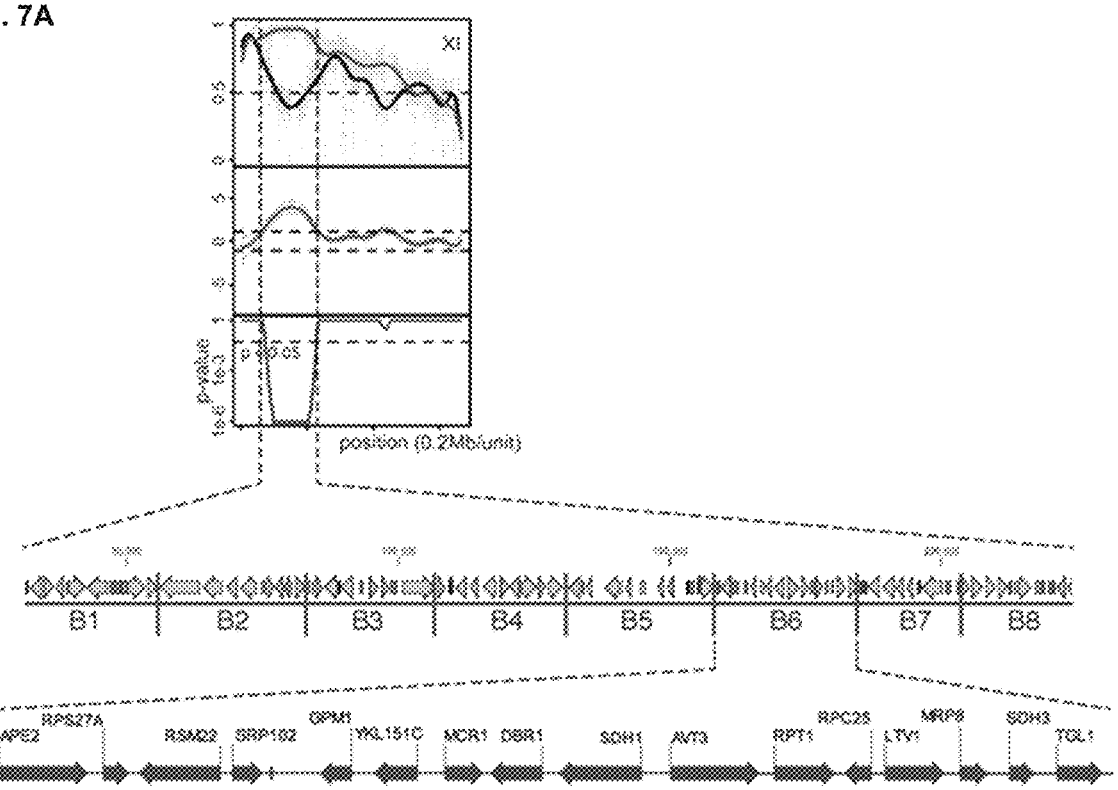
FIG. 7. Fine mapping of QTL1. A. Division of QTL1 in eight gene blocks for bRHA and genes present in block 6. B. Representative example of bRHA with blocks 3, 4, 5, and 6 (B3-B6), indicating that block 6 contains a causative gene. C. Acetic acid production as a function of time by the RHA strains for block 6, SBERH6/S288c B6Δ (•) and SBERH6 B6Δ/S288c (■) compared to the control strains Sb (SBERH6) (♦), Sc (S288c) (○) and SBERH6/S288c (□). D. RHA with the individual genes present in block 6, identifying SDH1 as a causative gene. E. Acetic acid production as a function of time by the RHA strains for the SDH1gene, SBERH6/S288c sdh1Δ(▲) and SBERH6 sdh1Δ/S288c (▼), compared to the control strains. Results are the mean of three biological replicates for each time-point. Error bars show standard deviation at each time-point. Control strains: Sb (SBERH6) (♦) Sc (S288c) (○) and SBERH6/S288c (□).
Figure 7B:
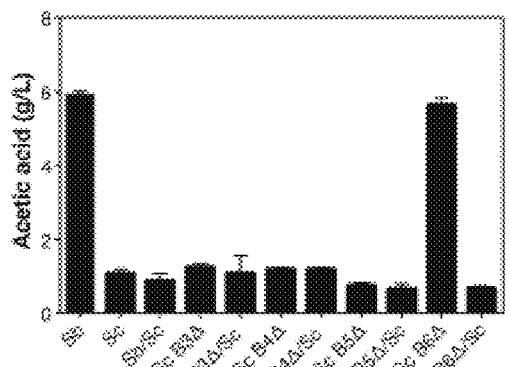
Figure 7D:
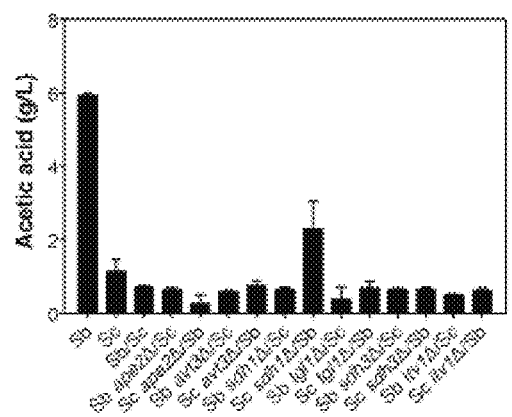
Figure 7C:
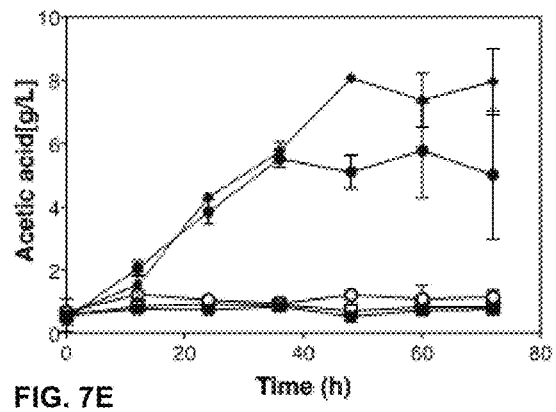

QTL1 had a length of 200,619 bp. We divided QTL1 into 8 blocks of genes (FIG. 7A) for bulk Reciprocal Hemizygosity Analysis (bRHA). For that purpose, each block was deleted in a reciprocal manner in chromosome XI of the SBERH6/S288c diploid strain. Allele-specific PCR was used to determine whether a block of genes deleted was from the superior or inferior parent. Strains were tested for acetic acid production in comparison with the strain with the reciprocal deletion of the same block. The results from this study revealed that block 6 was harbouring a causative genetic element responsible for the high acetic acid production phenotype. This block was 25,573 bp in size and flanked by the chromosomal positions NC_001143.9:g. 156173 and 181746. The RHA strain with a deletion of block 6 from the inferior parent chromosome (SBERH6/S288c block6Δ) exhibited a high acetic acid production phenotype, secreting 5.65±0.18 g/l. On the contrary, strains harbouring the reciprocal deletion of block 6 from the superior parent (SBERH6 block6Δ/S288c) failed to exhibit the phenotype, secreting 0.67±0.06 g/l. Similar reciprocal deletions for the three other blocks studied did not show any difference in the phenotype (FIG. 7B). To investigate whether block 6 fully accounted for the high acetic acid production phenotype, samples were taken at different time points during the course of acetic acid production by the two reciprocal RHA strains of the hybrid SBERH6/S288c with block 6 deleted. The results revealed that block 6 does not fully account for the phenotype. The SBERH6/S288c block6Δ strain showed a similar trend for acetic acid production as the superior parent up to 36 h of incubation. At that time point it had secreted 5.53±0.23 g/l compared to 5.75±0.30 g/l for the superior parent. After this time point, the accumulation of acetic acid by the SBERH6/S288c block6Δ strain deviated from that of the superior parent as it started to decline to a final value of 5.01±2.03 g/l after 72 h after incubation. On the other hand, the superior parent reached its maximum acetic acid production of 7.95±1.04 g/l at 72 h of incubation (FIG. 7C).

Figure 7E:
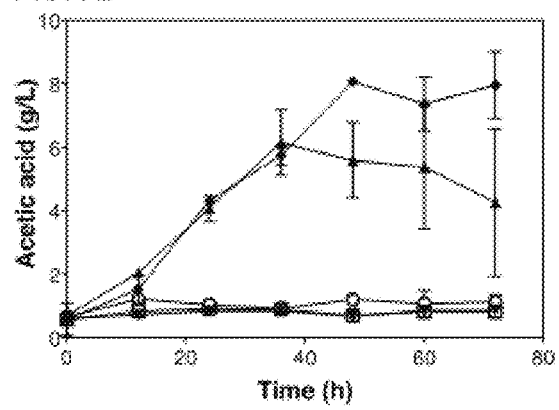

Example 8: Identification of the Causative Allele within QTL1 on Chromosome XI Sixteen open reading frames were present in block 6. Six of these genes, namely APE2, SDH1, AVT3, LTV1, SDH3 and TGL1, were prioritised for RHA in order to identify the causative gene(s) contributing to the high acetic acid phenotype. They were prioritised because APE2 contained a frameshift mutation while the other genes harboured at least one missense mutation (FIG. 7A). Deletion mutants of each gene constructed as hemizygote diploid strains were tested for acetic acid production. The results showed that the strain SBERH6/S288c sdh1Δ displayed higher acetic acid production (yielding 2.28±0.75 g/l) than SBERH6 sdh1Δ/S288c, which only produced 0.66±0.05 g/l. Furthermore, RHA with the hemizygous strains for the other five genes, containing either the allele from the superior or the inferior parent strain did not show any significant difference in acetic acid production levels (FIG. 7D). A time-course experiment for acetic acid production, performed with the SDH1 hemizygous strains confirmed that SBERH6/S288c sdh1Δ behaved similarly to SBERH6/S288c B6Δ. It reached a maximum acetic acid production level of 6.15±1.04 g/l after 36 h of incubation and displayed a similar acetic acid production level as the superior parent strain (SBERH6) at that time point. Also, the SBERH6 sdh1Δ/S288c strain only displayed the basal value of acetic acid production of 0.84±0.02 g/l (FIG. 7E), as was previously observed for the SBERH6 B6Δ/S288c strain.

Example 9: Sequence Analysis for Identification of the Causative Nucleotide Polymorphism Two point-mutations were found in the open-reading frame of the SDH1 gene from the SBERH6 haploid parent strain, derived from the S. boulardii Sb.P strain, being c. [604G>A]; [950A>T] and resulting in two non-synonymous mutations (p. [H202Y]; [F317Y]). Hence, we have named this allele sdh1$^{H202Y;F317Y}$. Next, we determined whether these non-synonymous mutations were also present in the other 11 S. boulardii strains employed in this study. The sequence of the SDH1 gene from all 12 S. boulardii strains was obtained by Sanger sequencing. Subsequent analysis of the SDH1 sequences obtained, revealed that both mutations observed in the SDH1 gene of SBERH6 and Sb.P were present in all the other 11 strains of S. boulardii analysed (FIG. 8A).

To investigate whether these mutations were unique to our collection of S. boulardii strains, or were also present in S. cerevisiae strains, we have made an alignment of the published SDH1 gene from 41 different S. cerevisiae strains, of which the genome has been completely sequenced (FIG. 8B shows the alignment for 18 of these S. cerevisiae strains). This analysis showed that the c.604G>A mutation, which resulted in the amino acid substitution of histidine202 to tyrosine, is common among S. cerevisiae strains. However, the c.950A>T mutation, which changed phenylalanine317 to tyrosine, was unique to our collection of S. boulardii strains and could not be detected in any one of the 41 completely sequenced S. cerevisiae strains (as shown for 18 strains in FIG. 8B).

Example 10: Identification of the Causative Allele within QTL2 on Chromosome XV To identify the second allele causative for high acetic acid accumulation, bRHA for QTL2 on chromosome XV was performed in the hybrid that was obtained by crossing SBERH6 with S288c sdh1$^{H202Y;F317Y}$, which will be referred to as hybrid 2. We opted for this approach since the superior sdh1$^{H202Y;F317Y}$ is recessive and required for acetic acid accumulation in the hybrid (SBERH6/S288c) background. Therefore, to find a second gene linked to high acetic acid accumulation, we needed to perform RHA in this new hybrid that is homozygous for this superior allele, sdh1$^{H202Y;F317Y}$.

Figure 9A:
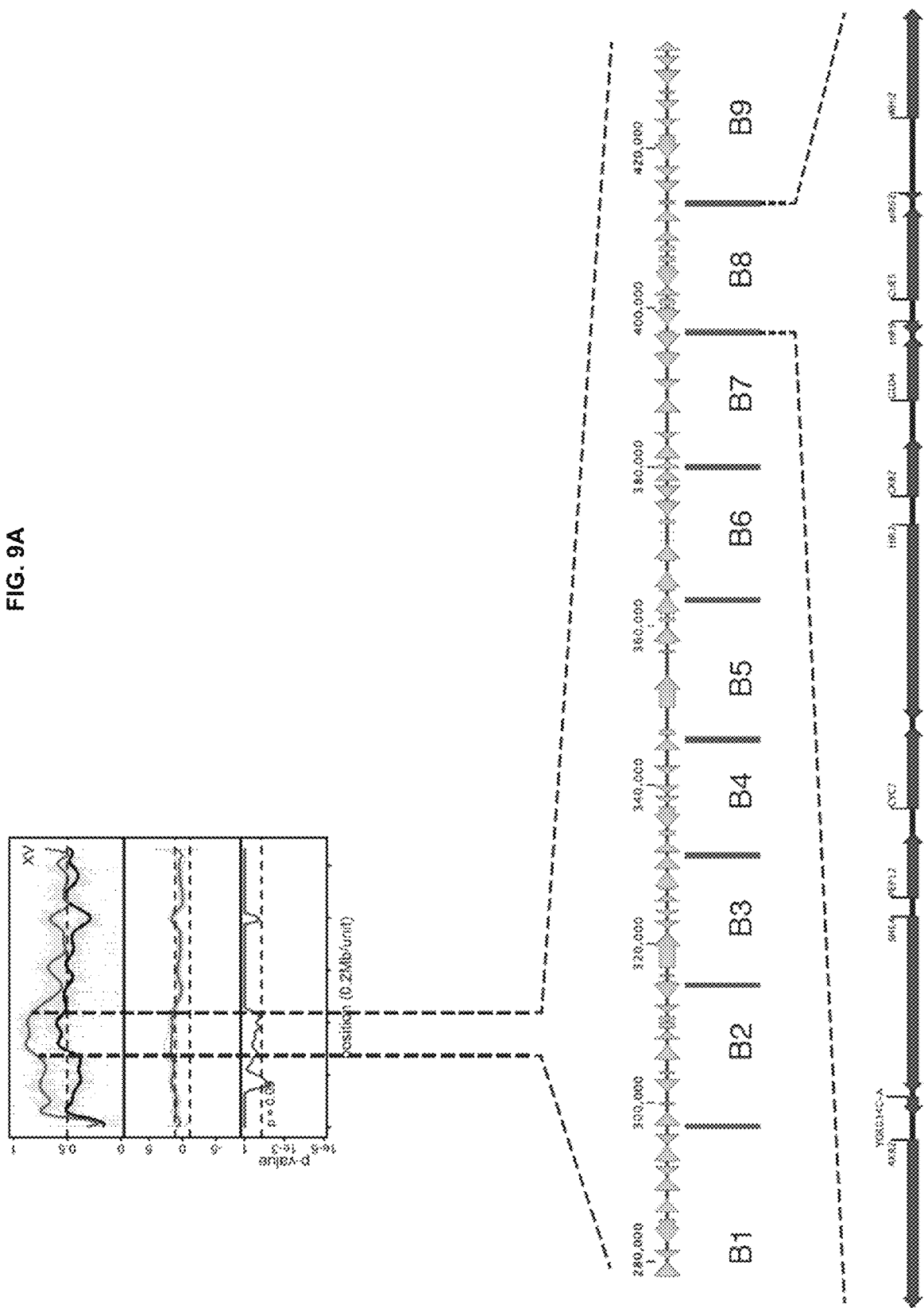
FIG. 9. Fine mapping of QTL2. A. Division of QTL2 in nine gene blocks for bRHA and genes present in block 8. B. Acetic acid production as a function of time by the RHA strains for block 8; SBERH6/S288c sdh1$^{H202Y;F317Y}$ B8Δ(•) and SBERH6 B8Δ/S288c sdh1$^{H202Y;F317Y}$ (○) compared to the control hybrid SBERH6/S288c sdh1$^{H202Y;F317Y}$ (■) C. Acetic acid production as a function of time by the RHA strains for WHI2; SBERH6/S288c sdh1$^{H202Y;F317Y}$ whi2Δ (•) and SBERH6 whi2Δ/S288c sdh1$^{H202Y;F317Y}$ (○), compared to the control hybrid SBERH6/S288c sdh1$^{H202Y;F317Y}$. Results are the mean of three biological replicates for each time-point. Error bars show standard deviation at each time-point.
Figure 9B:
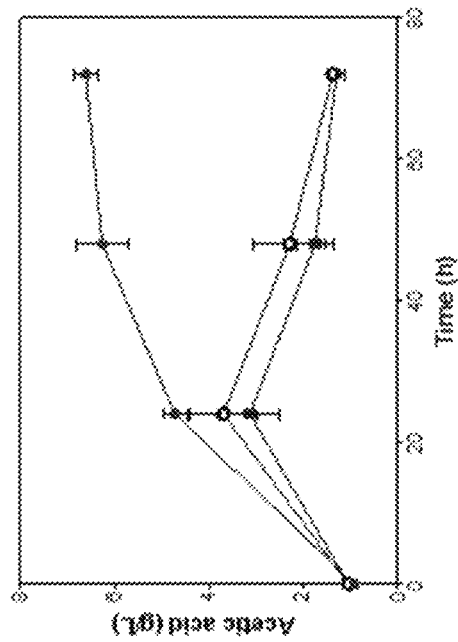

Similar to QTL1 on chromosome XI, QTL2 was investigated by bRHA. The region from chromosomal position NC_001147.9:g. 278057 to NC_001147.9:g. 433375 was divided into 9 blocks and each block was deleted in a reciprocal manner in chromosome XV of the SBERH6/S288c sdh1$^{H202Y;F317Y}$ diploid strain (FIG. 9A). Allele-specific PCR was used to determine whether the deleted block was from the superior or inferior parent. For each block, strains with the reciprocal deletion were compared in an acetic acid accumulation assay. For block 8, a clear difference was observed. Hybrid 2 with the deletion of block 8 from the superior parent chromosome (SBERH6 block6Δ/S288c sdh1$^{H202Y;F317Y}$) shows an acetic acid accumulation profile, comparable to this of hybrid 2. However, deletion of block 8 of the inferior parent results in high acetic acid accumulation (FIG. 9B). This block ranges from chromosomal position NC_001147.9:g. 394837 to NC_001147.9:g.

Figure 9C:
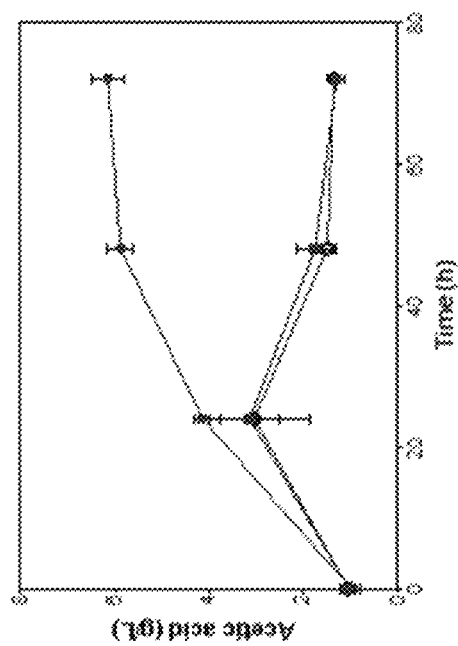

433375 and contains 10 genes: AKR2, YOR034C-A, SHE4, PEP12, CYC2, HIR2, CKB2, GLO4, CUE5 and WHI2. Since WHI2 contains several non-synonymous SNPs, regulates STRE-mediated gene expression and was previously identified as implicated in acetic acid tolerance, it was investigated individually by RHA, while the remaining genes were combined in one block, block 8.1[49,50]. An acetic acid accumulation assay with the RHA strains for WHI2 showed a clear difference, comparable to the difference that was seen for the RHA strains of block 8 (FIG. 9C). For the RHA strains of block 8.1, no difference in acetic acid accumulation profile was observed (data not shown). Sequence analysis of the open-reading frame of WHI2 from strain SBERH6 showed 12 SNPs, 6 synonymous and 6 non-synonymous (Table 2). An alignment of the published sequence of WHI2 of 41 different S. cerevisiae strains showed that 11 of these SNPs also occur in at least one of these 41 S. cerevisiae strains. However, the missense mutation c. 860G>C did not occur in any of these strains. To investigate whether this missense mutation occurs in the parental S. boulardii, Sb.P, from which SBERH6 was derived, or the other S. boulardii strains employed in this study, Sanger sequencing of WHI2 was performed. Sequence analysis showed that Sb.P and Sb.A were homozygous for this SNP, while 9 other S. boulardii strains were heterozygous and one strain, LSB, did not have this SNP (Table 2).

the c. 950A>T mutation which results in the change of phenylalanine317 to tyrosine, is the causative SNP within SDH1.

Figure 10A:
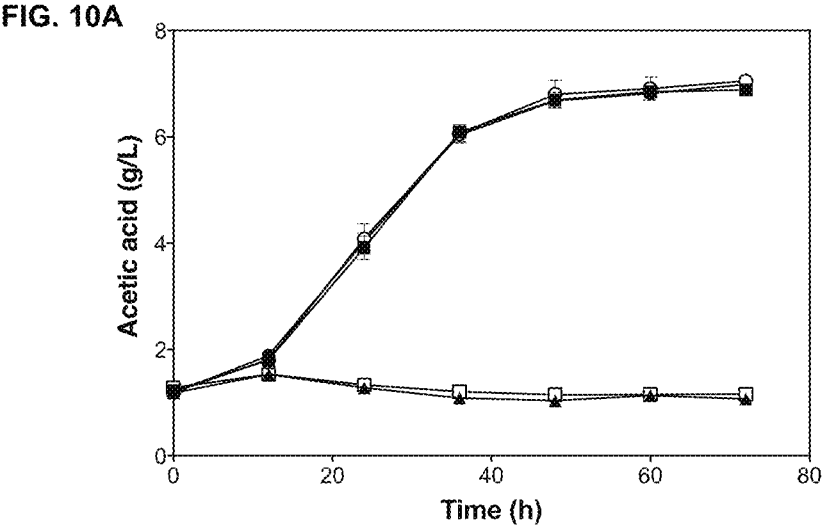
FIG. 10. Acetic acid production as a function of time for allele exchange of SDH1 and WHI2 in SBERH6. A. SDH1 allele exchanged in SBERH6; SBERH6 (•), SBERH6 reintegrant (○), SBERH6 sdh1$^{Y202H}$ (■) SBERH6 sdh1$^{Y317F}$ (□), SBERH6 sdh1$^{Y202H;Y317F}$ (▲). B. Allele exchange for WHI2 in SBERH6; SBERH6 (•), SBERH6 whi2::NatMX4 (○), SBERH6 reintegrant (■) SBERH6 WHI2$^{S288c}$(□), SBERH6 whi2$^{Ter2875}$ (▲). Results are the mean of three biological replicates for each time-point. Error bars show standard deviation at each time-point.
Figure 10B:
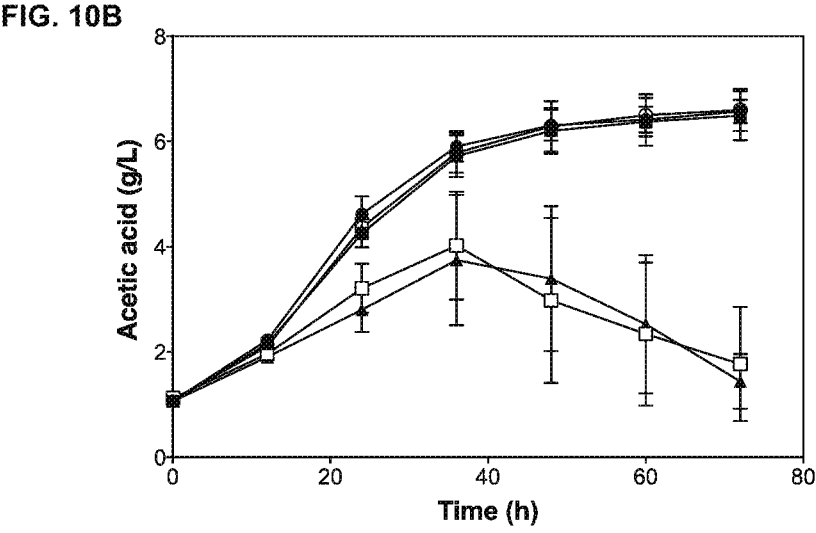

When WHI2 in SBERH6 was replaced by the wild type WHI2 allele from S288c, WHI2$^{S288c}$, instead of continuous accumulation of acetic acid, after 36 hours, a reduction in acetic acid levels was observed (FIG. 10B). Since the missense mutation c. 860G>C in SBERH6 results in a truncated protein, deletion of WHI2 in SBERH6 was also investigated. SBERH6 whi2::NatMX4 shows accumulation of acetic acid similar to SBERH6. To identify the causative SNP within WHI2, a hybrid allele, whi2$^{Ter2875}$, was introduced. This allele contains all SNPs present in SBERH6 in the open-reading frame of WHI2 and its promoter and terminator, except the missense mutation c. 860G>C. For SBERH6 whi2$^{Ter2875}$, an acetic acid accumulation profile comparable to the profile of SBERH6 WHI25288c was observed (FIG. 10B). This indicates that the c.860G>C mutation in SBERH6 is the causative SNP within WHI2.

Example 12: Allele Exchange of SDH1 and WHI2 in Sb.P

Since S. boulardii are unable to sporulate, a crossing strategy was applied to obtain SBERH6. Thus, SBERH6 has a mosaic DNA, containing regions from Sb.P and regions from Ethanol Red. To investigate the effect of SDH1 and

TABLE 2

Occurrence of SNPs in WHI2 for S288c, SBERH6 and 12 S. boulardii strains from our collection. Nucleic acid position is indicated relative to the start of the ORF. Positions of the non-synonymous SNPs are at Nucleic acid positions 4, 157, 250, 710, 860, and 1031, as well as all of column S288c and in row 860 at 7136, UL, 259, 7135, Sb.L, SAN, 7103, FLO, ENT, and LSB.

| Nucleic acid position | S288c | SBERH6 | Sb.P | Sb.A | 7136 | UL | 259 | 7135 | Sb.L | SAN | 7103 | FLO | ENT | LSB |
|---|---|---|---|---|---|---|---|---|---|---|---|---|---|---|
| 4 | G | A | A | A | A | A | A | A | A | A | A | A | A | A |
| 156 | C | T | T | T | T | T | T | T | T | T | T | T | T | T |
| 157 | A | G | G | G | G | G | G | G | G | G | G | G | G | G |
| 250 | A | G | G | G | G | G | G | G | G | G | G | G | G | G |
| 381 | A | G | G | G | G | G | G | G | G | G | G | G | G | G |
| 414 | A | G | G | G | G | G | G | G | G | G | G | G | G | G |
| 552 | C | T | T | T | T | T | T | T | T | T | T | T | T | T |
| 710 | C | A | A | A | A | A | A | A | A | A | A | A | A | A |
| 804 | C | T | T | T | T | T | T | T | T | T | T | T | T | T |
| 860 | C | G | G | G | C/G | C/G | C/G | C/G | C/G | C/G | C/G | C/G | C/G | C |
| 1031 | C | A | A | A | A | A | A | A | A | A | A | A | A | A |
| 1305 | C | T | T | T | T | T | T | T | T | T | T | T | T | T |

Figure 11A:
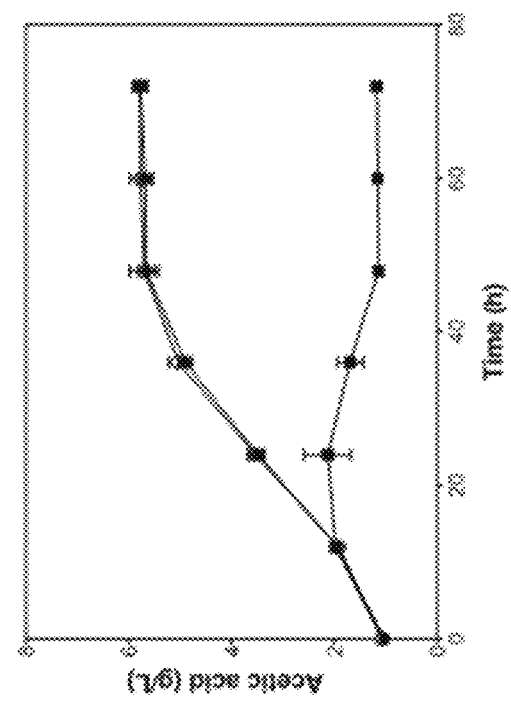
FIG. 11. Acetic acid production as a function of time. A. Allele exchange for SDH1 in Sb.P; Sb.P (•), Sb.P reintegrant (○), Sb.P sdh1$^{Y202H;Y317F}$/sdh1$^{Y202H;Y317F}$ (■) B. Allele exchange for WHI2 in Sb.P; Sb.P (•), Sb.P reintegrant (○), Sb.P WHI2$^{S288c}$/WHI2$^{S288c}$ (■) C. Reciprocal deletions of WHI2 in *S. boulardii* 259, 259 whi2/whi2$^{Ter2875}$::NatMX4 (•), 259 (○), 259 whi2::NatMX4/whi2$^{Ter2875}$ (■) D. Reciprocal deletions and allele exchange of WHI2 in *S. boulardii* 7103; 7103 (•),7103 whi2/whi2$^{Ter2875}$::NatMX4 (○), 7103 whi2::NatMX4/whi2$^{Ter2875}$ (■) 7103 whi2$^{Ter2875}$/whi2$^{Ter2875}$ (□), 7103 whi2/whi2 (▲), 7103 reintegrants (Δ), 7103 whi2::NatMX4/whi2$^{Ter3875}$::Ble$^R$ (♦) Results are the mean of three biological replicates for each time-point. Error bars show standard deviation at each time-point.
Figure 11B:
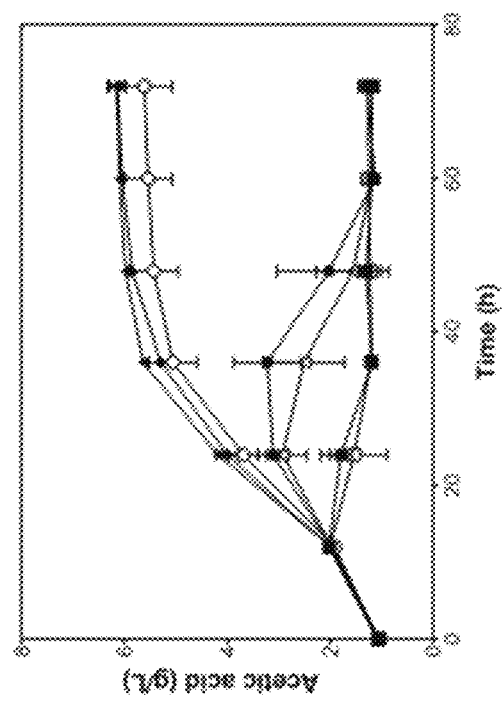

Example 11: Causative Nucleotide Confirmation Through Allele Exchange in SBERH6 and S288c In order to investigate SDH1 and WHI2 further as causative alleles for high acetic acid accumulation, allele exchange was performed in SBERH6 and S288c. When SDH1 in SBERH6 was replaced by the wild type SDH1 allele from S288c, resulting in strain SBERH6 sdh1$^{Y202H;Y317F}$, the high acetic acid phenotype was abolished (FIG. 10A). While reintroduction of the superior allele resulted in an acetic acid accumulation profile comparable to this of SBERH6. In order to identify the SNP within SDH1, causative for high acetic acid accumulation, hybrid alleles, sdh1$^{Y202H}$ and sdh1$^{Y317F}$, were introduced in SBERH6. For SBERH6 sdh1$^{Y317F}$, a total abolishment of acetic acid accumulation, as was seen for SBERH6 sdh1$^{Y202H;Y317F}$ was observed. While SBERH6 sdh1$^{Y202H}$ accumulated a similar amount of acetic acid as SBERH6. This clearly indicates that WHI2 on acetic acid accumulation of the wild type S. boulardii parent, Sb.P, we replaced the superior alleles by their inferior counterpart of S288c. Introduction of the inferior SDH1 in Sb.P results in an abolishment of acetic acid accumulation (FIG. 11A). This effect is comparable to the effect that was observed when the inferior allele was introduced in SBERH6. Introduction of the inferior WHI2 in Sb.P also results in an abolishment of acetic acid accumulation (FIG. 11B).

Example 13: Investigation of WHI2 in Other S. boulardii Strains

Sequencing data showed that two S. boulardii strains from our collection, Sb.P and Sb.A, are homozygous for the causative SNP, c.860G>C in WHI2 (Table 2). These two strains are also the only S. boulardii strains from our collection that are able to accumulate high levels of acetic acid. The other S. boulardii from our collection are also able to produce moderate levels of acetic acid, however, after 48 to 60 hour, the acetic acid concentration is reduced to a basal level, abolishing its accumulation.

Figure 11C:
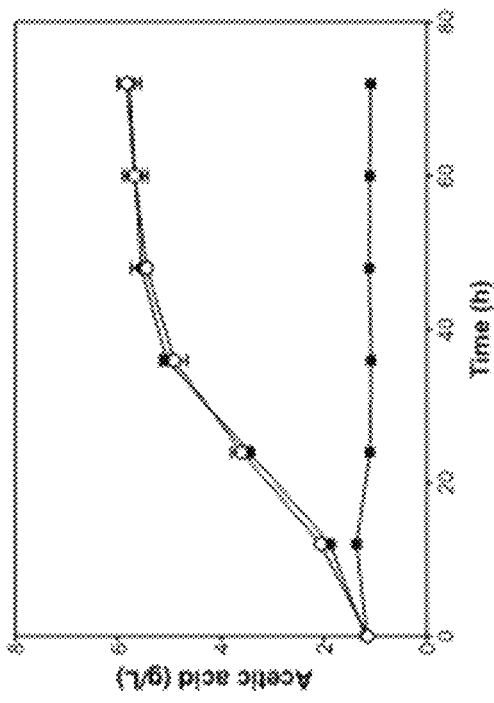
Figure 11D:
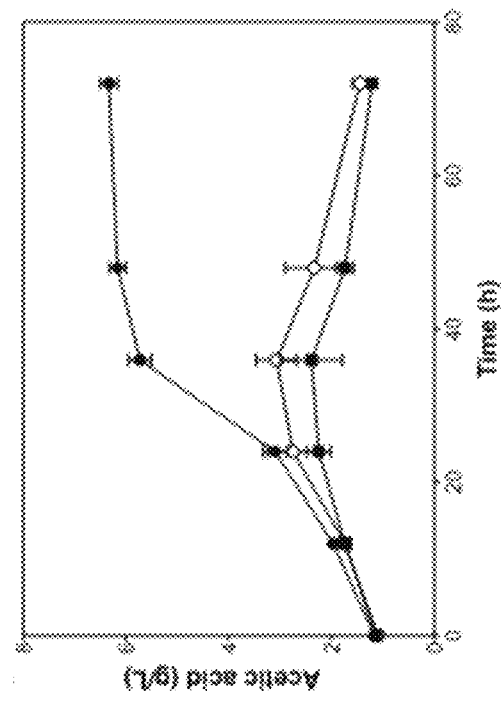

To investigate whether the high acetic acid accumulation phenotype could be transferred to other S. boulardii strains by modification of WHI2, the gene was deleted in a reciprocal manner in strain 259. The strain where only the superior truncated allele was deleted was compared in an acetic acid accumulation assay to the strain where the full-length WHI2 was deleted (FIG. 11C). Deletion of the superior allele, results in a small decrease in acetic acid accumulation, while deletion of the full-length variant, whi2$^{Ter2875}$ resulted in increased acetic acid accumulation, reaching an acetic acid production of 6.34±0.18 g/l at 72 h of incubation. A comparable result was obtained with another S. boulardii strain, 7103 (FIG. 11D). However, besides reciprocally deleting WHI2, we also constructed strains that were homozygous for the full-length allele, whi2$^{Ter2875}$, or the truncated superior allele, whi2. Strain 7103 whi2/whi2, homozygous for the superior allele of SBERH6, shows high levels of acetic acid accumulation. While the strains where the superior variant was deleted and the strain homozygous for the full-length allele, whi2$^{Ter2875}$, show acetic acid accumulation that is reduced when compared to the wild type 7103 or the reintegrants. These results show that modification of WHI2 or allele exchange of the causative mutation c.860G>C can be applied to establish the high acetic acid accumulation phenotype in S. boulardii, other than Sb.P or Sb.A.

Example 14: Validation of Probiotic Effect of Optimized S. boulardii Strains Multiple experimental set-ups are available in the prior art to assess the probiotic effect of S. boulardii strains or to compare two or more S. boulardii strains on their probiotic capacity. A plethora of in vivo experimental set-ups are available in the art and several models are described in the detailed description of current application.

In order to compare the optimized S. boulardii strains disclosed in current application with the currently available S. boulardii strains, we chose to use a S. typhimurium challenged mice experiment similar to Martins et al (2013, Microbes and Infection 15:270-279). Mice are treated with Salmonella typhimurium (intragastrically with 0.1 ml of a bacterial suspension containing 10$^5$ CFU/ml) with or without prior administration of S. boulardii. Two different S. boulardii strains are compared to each other: 1) S. boulardii strain 7103 heterozygous for the WHI2$^{C860G}$ mutation (see Table 2) and 2) the engineered S. boulardii strain 7103 homozygous for the WHI2$^{C860G}$ mutation (as described in Example 13). The S. boulardii treatments start 10 days before infection and continue throughout the experiment by a daily dose of 0.1 ml containing 10$^9$ CFU/ml administered through oral gavage. Survival rate, gut histology and translocation of bacteria after S. typhimurium challenge are investigated for the 2 different S. boulardii strains. Based on the convincing in vitro data Applicants expect to observe that the S. boulardii strain 7103 homozygous for the WHI2$^{C860G}$ mutation which produces more acetic acid compared to strain 7103 heterozygous for said mutation, would have a beneficial effect in controlling the intestinal S. typhimurium infection compared to strain 7103 heterozygous for the WHI2$^{C860G}$ mutation.

Materials and Methods

Strains, media and culture conditions: The strains used in this work are listed in Table 1. Yeast cells were propagated in YPD medium containing 10 g/L yeast extract, 20 g/L bacteriological peptone, and 20 g/L glucose at 30° C. or 35° C. To make solid nutrient plates the media were supplemented with 1.5 g/L bacto agar. Where appropriate, the medium was supplemented with antibiotics. For S. cerevisiae i.e. 200 mg/L geneticin, 300 mg/L hygromycin B or 100 mg/L nourseothricin. For S. boulardii i.e. 100 mg/L geneticin, 75 mg/L hygromycin B, 5 mg/L bleomycin, 10 mg/L nourseothricin. Mating, sporulation and spore isolation were carried out using standard protocols[86,87]. The bacterial indicator strain was pre-grown in Mueller Hinton broth (22 g/L).

General molecular biology methods: Yeast genomic DNA was extracted with Phenol/Chloroform/Isoamyl alcohol (25:24:1) and, where required, further purified by ethanol precipitation. PCR was performed according to manufacturer's specifications with Standard Taq DNA polymerase for diagnostic purposes or Q5 high-fidelity DNA polymerase for sequencing or amplification of donor DNA (New England Biolabs). Either the LiOAC/SS-DNA/PEG protocol or electroporation were used as transformation methods[88,89]. Sanger sequencing was performed by the Genetic Service Facility of the VIB. Tetrads were dissected by using the micromanipulator from Singer Instruments (Roadwater Watchet Somerset, UK).

Amplified Fragment Length Polymorphisms (AFLP): DNA was isolated using a standard protocol. Briefly, yeast cells harvested from a YPD plate with a sterile loop were homogenized with the aid of sterile sand, 750 µL lysis buffer (0.5% w/v Sarkosyl, 0.5% w/v SDS) and 750 µL PCI (25:24:1) in a 2 mL screw-cap tube. After centrifugation at maximum speed for 15 min, 600 µL of the extract was mixed with 80 µL, 3.0 M sodium acetic acid (pH 5) in a 1.5 mL Eppendorf tube followed by addition of 1500 µL 100% ethanol. Tubes were then inverted a few times and incubated at −20° C. for 60 min. Precipitated DNA was isolated by centrifugation for 10 minutes and washed with 200 µl ice-cold 70% ethanol. The DNA pellet was finally air-dried and resuspended in 100 µL TE buffer. The isolated DNA was used for AFLP determination according to the method of Borst et al[90].

Acetic acid accumulation assay: Overnight yeast precultures were adjusted to an OD$_{600}$ of 0.2 in 50 ml YPD in a 300 ml Erlenmeyer flask. Flasks were incubated by shaking at 200 rpm and 37° C. in a shaking incubator for 48 or 72 h. To obtain cell-free culture supernatants, aliquots of yeast cultures were withdrawn from the flasks and centrifuged at maximum speed (14,000 rpm) for 5 min. The supernatants were used for agar-well diffusion assays or subjected to High Performance Liquid Chromatography (HPLC) to determine the acetic acid concentration. For time-course measurements, samples were withdrawn from the cultures every 12 h for further analysis.

Agar-well diffusion assays: For the agar-well diffusion assays, 25 ml molten soft Mueller Hinton agar (7.5 g bacto agar/L Mueller Hinton broth) was inoculated with 5.10$^4$ cells/mL E. coli indicator strain. This was followed by addition of the bacterial growth indicator, iodonitrotetrazolium chloride (in 50% methanol), to a final concentration of 0.2 mg/ml and brief vortexing. A square petri dish containing 80 ml solidified Muller Hinton agar was then overlaid with the molten top agar. The top agar was allowed to solidify, after which 9 wells (in 3×3 format) were punched into both agar layers using a 12 mm sterile cork borer. The resulting agar discs were carefully removed from each well with a pair of sterile thongs and discarded. Each well was then filled with about 700 µl of yeast culture supernatant. All agar-well plates were incubated at 37° C. for 12-18 h.

HPLC: The acetic acid concentration in yeast cell-free culture supernatants was measured with HPLC (Waters® isocratic Breeze™ HPLC). The flow rate of eluent (5 mM $H_2SO_4$) was 1 ml/min while the column temperature was maintained at 75° C. Detection was by refractive index measurement (Waters, 2414 RI detector). Acetic acid was identified in samples based on retention time using an acetic acid standard whilst its concentration was determined based on peak area.

Yeast ploidy determination: Ploidy was determined according to Popolo et al[91]. Strains were grown in 3 mL YPD for 5-6 h (mid-log phase). A volume of culture corresponding to $2 \times 10^7$ cells, based on $OD_{600}$, was withdrawn, made up to a total volume of 1 mL with ice-cold milli-Q water and centrifuged (5 min, 5000 rpm). The resulting pellet was resuspended in 1 mL of ice-cold 70% ethanol and stored at 4° C. for a minimum of 1 day for cell fixation. Cells were then collected by centrifugation and the pellet treated with 100 µl, 1 mg/mL RNAse A, followed by 90 min incubation at 37° C. in a shaking water bath. After RNAse A treatment, cells were collected by centrifugation and the pellet stained with 100 µl 0.046 mM propidium iodide. This was followed by incubation at 4° C. for at least 2 days. Stained cells were diluted 100 fold in ice-cold milli-Q water for flow cytometry.

Yeast viability determination: Cell viability was assessed according to Boyd et al[92]. Cultures were adjusted to an $OD_{600}$ of 0.5 in 1 ml of sterile milli-Q water. 50 µl of each cell suspension in water was further diluted to 460 µl with sterile milli-Q water and stained with 40 µl 20 µg/ml oxonol ($DiBAC_4$) (Sigma-Aldrich). Stained cells were incubated at room temperature for 15 min before being subjected to flow cytometry.

Deletion of the HO endonuclease gene and mating type switch: The HO endonuclease gene was deleted according to Goldstein and McCusker[93]. Since the *S. boulardii* Sb.P strain is diploid, the two copies of HO were deleted sequentially. Deletion of the first copy was carried out by transformation with a cassette harbouring the hygromycin B resistance gene (HphMX4). Transformants were selected on YPD-hygromycin B plates and correct integration of the HphMX4 cassette was assessed by PCR. A successful hoΔ strain was then transformed with a cassette harbouring a geneticin resistance gene (KanMX4). Transformants were selected on a YPD-geneticin/hygromycin B plate and correct integration of the KNMX4 cassette was assessed by PCR. To obtain homozygous MAT loci in both Sb.P (MATa/a, hoΔ::hphMX$_4$/ho::KNMX$_4$) and ER (MATα/α; heterothallic), the two strains were transformed with plasmid pFL39_GAL_HO_NatMX4, harbouring the HO gene controlled by the galactose inducible promotor, pGAL1. Successful transformants were grown overnight in liquid YPD medium supplemented with nourseothricin. Cells from the preculture were harvested by centrifugation and were resuspended in 10 mL YP supplemented with nourseothricin and 2% galactose. Galactose induction of HO was discontinued by addition of 2% glucose and 1 mL aliquots of the culture were then withdrawn after two 2, 3, 4 and 5 hours of growth, combined, and plated out on YPD to obtain single colonies. The mating type of the colonies obtained was assessed by mating type PCR[94] and the appropriate a/a or α/α strains were selected.

DNA isolation for Illumina sequencing: High molecular weight DNA was isolated for each sample (superior parent strain and the two pools). For that purpose, each segregant of both pools (inferior and superior) was grown separately in 3 mL YPD for 2 days. The superior parent SBERH6 was grown for the same period in 25 ml YPD. Culture volumes equivalent to 1 mL with an $OD_{600}$ of 40 of each segregant in the superior and inferior pool, respectively, were combined. DNA isolation was carried out using the MasterPure™ Yeast DNA Purification Kit (Epicentre, Madison, WI, USA), according to the manufacturer's instructions. The isolated DNA was submitted to Illumina HiSeq2000 technology (BGI, Hong Kong, China) with libraries of 500 bp and paired-end reads of 101 bp. The short read sequences were mapped against the S288c reference sequence and all variants (SNPs and small indels) were identified and quality filtered using the NGSEP pipeline[48]. In parallel, CLC genomic workbench (CLC Bio-Qiagen, Aarhus, Denmark) was used to map the reads in order to allow easy comparison of read mappings to the annotated genome of S288c.

Reciprocal Hemizygosity Analysis (bRHA): QTL1 (NC_001143.9:g.31118 . . . 231737) was defined as the segment of DNA on chromosome XI where the difference between the average SNV of the superior pool and inferior pools assumed statistical significance (p-value≤0.05). QTL1 was split into 8 blocks of genes (approximately 25 kbp for each block). Blocks 3, 4, 5 and 6 were deleted separately in a reciprocal manner in the hybrid diploid (SBERH6/S288c). Each deletion was achieved using a split geneticin resistance marker (KanMX4) knock-out cassette. The cassette was constructed by adaptor-mediated fusion of PCR-amplified left and right flanking sequences (between 400-700 bp) for each block, with the left and right fragments of a KanMX4 marker, respectively. The hybrid diploid (SBERH6/S288c) was subsequently transformed with the two fragments of the KanMX4 marker specifically constructed for each block. For RHA of the individual genes in QTL1, the exact ORF of the left and right flanking sequences and the prioritised genes in QTL1 (APE2, SDH1, AVT3, LTV1, SDH3 and TGL1) were deleted with KanMX4. The methodology used for cassette construction and transformation of the strains is the same as described above for bRHA. The non-essential genes APE2, SDH1, AVT3, LTV1 and TGL1 were deleted in the haploid backgrounds of SBERH6 and S288c. Successful transformants were assessed for correct integration of the cassette at each locus by PCR. S288c transformants with the right integration at each locus were subsequently crossed with SBERH6 and vice versa to obtain reciprocal hemizygote strains for each gene. The only essential gene, SDH3, was deleted in the hybrid diploid (SBERH6/S288c) background. Successful transformants harbouring an SDH3 deletion in one parental chromosome were genotyped using SNP-PCR. For RHA of QTL2, the entire block (bRHA) or the exact ORF were deleted with NatMX4 in the diploid SBERH6/S288c sdh1$^{H202Y;F317Y}$ hybrid strains. The marker was amplified from plasmid pTOPO-G1-NatMX4-G1 with primers containing 50 bp tails, homologous to the regions flanking the targeted region, as described by Baudin et al.[95]. Correct integration of the marker was confirmed by PCR and the remaining, non-deleted allele, was identified by allele-specific PCR.

Genotyping by allele-specific PCR: Allele-specific PCR for each block of deleted genes or each individual gene in the RHA assay and allele replacement was performed by pairing a forward primer, containing either the SBERH6 or S288c nucleotide as the 3' terminal nucleotide, with a common reverse primer. To increase specificity, for some primers, an additional single nucleotide artificial mismatch was added within the three bases closest to the 3' end[96]. The annealing temperature for each set of primers was optimized by gradient PCR using genomic DNA of both parents, so as to allow only hybridization with primers containing the exact complement.

CRISPR/Cas9 mediated gene exchange: The gRNA plasmid and the Cas9 expression plasmids used in this study were based on the paper by DiCarlo et al.[97], and were recently described by Holt and coworkers[98]. Allele replacement of SDH1 and WHI2 was performed in a stepwise manner. First, a dominant selection marker (ble$^r$ or NatMX4), or both when a diploid strain was modified, flanked by gRNA recognition sites, G1, was used to delete the region of interest. The selection markers were amplified from plasmid pTOPO_G1-NatMX4-G1 or pTOPO-G1-Ble$^R$-G1, with primers containing tails, homologous to the regions flanking the targeted region. Correct integration of the cassettes was confirmed by PCR. For each replacement, to obtain independent replacement strains, three successful transformants were selected and all following steps were performed in parallel. Next, pTEF-Cas9-KanMX4, the plasmid harboring Cas9, was introduced. Finally, the plasmid expressing the gRNA, pgRNA-G1-HphMX, that specifically targets the G1 sequence (5'-GGCTGAT-TTTCGCAGTTCGGGGG-3') flanking the marker, was introduced together with donor DNA to repair the double stranded break by homology directed repair. The design of this gRNA was based on the finding of Farboud and Meyer that Cas9-mediated DNA cleavage was enhanced at this G1 site due to the presence of a GG dinucleotide at the 3' end of the protospacer[99]. This gRNA was checked for potential off targeting with BLAST. For SDH1, the region from 99 bp upstream of the first non-synonymous SNP (c.604G>A), to 91 bp downstream of the second non-synonymous mutation (c.950A>T), was replaced. While for WHI2, the entire region between the gene downstream and upstream of WHI2 was replaced. Repair templates were amplified from genomic DNA of SBERH6 or S288c and variant whi2$^{Stop2875}$ was amplified with genomic DNA of S. boulardii strain LSB as template. For SDH1, repair templates harboring just one of the two non-synonymous mutations were constructed. For this purpose the left and right part of the repair template for SDH1 were amplified separately with genomic DNA of SBERH6 or S288c as template. Next, these fragments were joined into a single repair template by fusion PCR using an overlapping sequence between the two fragment, yielding two repair templates for SDH1 that each contained one of the two non-synonymous SNPs. Also, for each strain that was modified, re-integrants, where the native DNA was used as a repair template, were constructed. Replacement of the NatMX4 or ble$^R$ marker resulted in sensitivity to nourseothricin or phleomycin respectively and was assessed by spot assay. The presence of the introduced variant was verified by PCR and next, by sub-culturing three times in YPD, the plasmids were lost. Plasmid loss was verified by spot assay on YPD supplemented with hygromycin B or geneticin. Finally, the sequences of the replaced region and its surroundings were confirmed by Sanger sequencing.

Growth assays by spot dilution series for assessment of acetic acid utilization capacity: The strains were propagated in 3 mL YPD broth at 30° C. for one day. A dilution of each culture was prepared in sterile milli-Q water to an $OD_{600}$ of 0.5. A 5 µL droplet of a ten-fold dilution series (10° to 10-5) of each strain was spotted on YPD as well as on YP+1% KAcetate (YPAc) (pH 5). Both YPD and YPAc plates were incubated at 30° C. and 37° C.

SEQUENCES

SEQ ID No. 1
  DNA sequence WHI2 (C860G mutation) from *Saccharomyces boulardii*
SEQ ID No. 2
  DNA sequence SDH1 (C604T, T950A mutation) from *Saccharomyces boulardii*
SEQ ID No. 3
  DNA sequence WHI2 (wild-type) from *Saccharomyces boulardii*
SEQ ID No. 4
  Protein sequence Whi2 (wild-type) from *Saccharomyces boulardii*
SEQ ID No. 5
  Protein sequence Whi2 (S270* mutation) from *Saccharomyces boulardii*
SEQ ID No. 6
  DNA sequence SDH1 (wild-type) from *Saccharomyces cerevisiae*
SEQ ID No. 7
  Protein sequence Sdh1 (wild-type) from *Saccharomyces cerevisiae*
SEQ ID No. 8
  Protein sequence Sdh1 (H202Y, F317Y mutation) from *Saccharomyces boulardii*

REFERENCES

1. Szajewska, H. What are the indications for using probiotics in children? *Arch Dis Child* (2015).
2. Senok, A. C., Verstraelen, H., Temmerman, M. & Botta, G. A. Probiotics for the treatment of bacterial vaginosis. *Cochrane Database Syst Rev*, CD006289 (2009).
3. Butel, M. J. Probiotics, gut microbiota and health. *Med Mal Infect* 44, 1-8 (2014).
4. Macfarlane, G. T. & Cummings, J. H. Probiotics, infection and immunity. *Curr Opin Infect Dis* 15, 501-506 (2002).
5. Hou, C., Zeng, X., Yang, F., Liu, H. & Qiao, S. Study and use of the probiotic *Lactobacillus reuteri* in pigs: a review. *J Anim Sci Biotechnol* 6, 14 (2015).
6. Chaucheyras-Durand, F. & Durand, H. Probiotics in animal nutrition and health. *Benef Microbes* 1, 3-9 (2010).
7. Verschuere, L., Rombaut, G., Sorgeloos, P. & Verstraete, W. Probiotic bacteria as biological control agents in aquaculture. *Microbiol Mol Biol Rev* 64, 655-671 (2000).
8. Balcazar, J. L., et al. The role of probiotics in aquaculture. *Vet Microbiol* 114, 173-186 (2006).
9. Guandalini, S. Probiotics for prevention and treatment of diarrhea. *J Clin Gastroenterol* 45 Suppl, S149-153 (2011).
12. Bermudez-Brito, M., Plaza-Diaz, J., Munoz-Quezada, S., Gomez-Llorente, C. & Gil, A. Probiotic mechanisms of action. *Ann Nutr Metab* 61, 160-174 (2012).
13. Vanderpool, C., Yan, F. & Polk, D. B. Mechanisms of probiotic action: Implications for therapeutic applications in inflammatory bowel diseases. *Inflamm Bowel Dis* 14, 1585-1596 (2008).
14. Elmer, G. W., Surawicz, C. M. & McFarland, L. V. Biotherapeutic agents. A neglected modality for the treatment and prevention of selected intestinal and vaginal infections. *JAMA* 275, 870-876 (1996).
15. McFarland, L. V. Systematic review and meta-analysis of *Saccharomyces boulardii* in adult patients. *World J Gastroenterol* 16, 2202-2222 (2010).
16. Mitterdorfer, G., Mayer, H. K., Kneifel, W. & Viernstein, H. Clustering of *Saccharomyces boulardii* strains within the species *S. cerevisiae* using molecular typing techniques. *J Appl Microbiol* 93, 521-530 (2002).

17. Mackenzie, D. A., et al. Relatedness of medically important strains of *Saccharomyces cerevisiae* as revealed by phylogenetics and metabolomics. *Yeast* 25, 501-512 (2008).
18. van der Aa Kuhle, A. & Jespersen, L. The taxonomic position of *Saccharomyces boulardii* as evaluated by sequence analysis of the D1/D2 domain of 26S rDNA, the ITS1-5.8S rDNA-ITS2 region and the mitochondrial cytochrome-c oxidase Il gene. *Syst Appl Microbiol* 26, 564-571 (2003).
19. Edwards-Ingram, L. C., et al. Comparative genomic hybridization provides new insights into the molecular taxonomy of the *Saccharomyces* sensu stricto complex. *Genome Res* 14, 1043-1051 (2004).
20. Khatri, I., et al. Gleaning evolutionary insights from the genome sequence of a probiotic yeast *Saccharomyces boulardii*. *Gut Pathog* 5, 30 (2013).
21. Cascio, V., et al. S-Adenosyl-L-methionine protects the probiotic yeast, *Saccharomyces boulardii*, from acid-induced cell death. *BMC Microbiol* 13, 35 (2013).
22. Edwards-Ingram, L., et al. Genotypic and physiological characterization of *Saccharomyces boulardii*, the probiotic strain of *Saccharomyces cerevisiae*. *Appl Environ Microbiol* 73, 2458-2467 (2007).
23. Fietto, J. L., et al. Molecular and physiological comparisons between *Saccharomyces cerevisiae* and *Saccharomyces boulardii*. *Can J Microbiol* 50, 615-621 (2004).
24. Tomar, P., et al. Sporulation genes associated with sporulation efficiency in natural isolates of yeast. *PLoS One* 8, e69765 (2013).
25. Kotowska, M., Albrecht, P. & Szajewska, H. *Saccharomyces boulardii* in the prevention of antibiotic-associated diarrhoea in children: a randomized double-blind placebo-controlled trial. *Aliment Pharmacol Ther* 21, 583-590 (2005).
26. Duman, D. G., et al. Efficacy and safety of *Saccharomyces boulardii* in prevention of antibiotic-associated diarrhoea due to Helicobacterpylori eradication. *Eur J Gastroenterol Hepatol* 17, 1357-1361 (2005).
27. Villar-Garcia, J., et al. Effect of probiotics (*Saccharomyces boulardii*) on microbial translocation and inflammation in HIV-treated patients: a double-blind, randomized, placebo-controlled trial. *J Acquir Immune Defic Syndr* 68, 256-263 (2015).
28. McFarland, L. V., et al. A randomized placebo-controlled trial of *Saccharomyces boulardii* in combination with standard antibiotics for *Clostridium difficile* disease. *JAMA* 271, 1913-1918 (1994).
29. Czerucka, D., Piche, T. & Rampal, P. Review article: yeast as probiotics—*Saccharomyces boulardii*. *Aliment Pharmacol Ther* 26, 767-778 (2007).
30. Dalmasso, G., et al. *Saccharomyces boulardii* inhibits inflammatory bowel disease by trapping T cells in mesenteric lymph nodes. *Gastroenterology* 131, 1812-1825 (2006).
31. Qamar, A., et al. *Saccharomyces boulardii* stimulates intestinal immunoglobulin A immune response to *Clostridium difficile* toxin A in mice. *Infect Immun* 69, 2762-2765 (2001).
32. Pothoulakis, C., et al. *Saccharomyces boulardii* inhibits *Clostridium difficile* toxin A binding and enterotoxicity in rat ileum. *Gastroenterology* 104, 1108-1115 (1993).
33. Castagliuolo, I., LaMont, J.T., Nikulasson, S.T. & Pothoulakis, C. *Saccharomyces boulardii* protease inhibits *Clostridium difficile* toxin A effects in the rat ileum. *Infect Immun* 64, 5225-5232 (1996).
34. Mumy, K. L., Chen, X., Kelly, C. P. & McCormick, B. A. *Saccharomyces boulardii* interferes with *Shigella* pathogenesis by postinvasion signaling events. *Am J Physiol Gastrointest Liver Physiol* 294, G599-609 (2008).
35. Gedek, B. R. Adherence of *Escherichia coli* serogroup O 157 and the *Salmonella typhimurium* mutant DT 104 to the surface of *Saccharomyces boulardii*. *Mycoses* 42, 261-264 (1999).
39. Dobson, A., Cotter, P.D., Ross, R.P. & Hill, C. Bacteriocin production: a probiotic trait? *Appl Environ Microbiol* 78, 1-6 (2012).
40. O'Shea, E. F., Cotter, P. D., Stanton, C., Ross, R. P. & Hill, C. Production of bioactive substances by intestinal bacteria as a basis for explaining probiotic mechanisms: bacteriocins and conjugated linoleic acid. *Int J Food Microbiol* 152, 189-205 (2012).
41. Cursino, L., et al. Exoproducts of the *Escherichia coli* strain H22 inhibiting some enteric pathogens both in vitro and in vivo. *J Appl Microbiol* 100, 821-829 (2006).
42. Tejero-Sarinena, S., Barlow, J., Costabile, A., Gibson, G. R. & Rowland, I. In vitro evaluation of the antimicrobial activity of a range of probiotics against pathogens: evidence for the effects of organic acids. *Anaerobe* 18, 530-538 (2012).
43. Hutt, P., Shchepetova, J., Loivukene, K., Kullisaar, T. & Mikelsaar, M. Antagonistic activity of probiotic lactobacilli and bifidobacteria against entero- and uropathogens. *J Appl Microbiol* 100, 1324-1332 (2006).
44. Meijnen, J. P., et al. Polygenic analysis and targeted improvement of the complex trait of high acetic acid tolerance in the yeast *Saccharomyces cerevisiae*. *Biotechnol Biofuels* 9, 5 (2016).
45. Yang, Y., et al. QTL analysis of high thermotolerance with superior and downgraded parental yeast strains reveals new minor QTLs and converges on novel causative alleles involved in RNA processing. *PLoS Genet* 9, e1003693 (2013).
46. Hubmann, G., et al. Identification of multiple interacting alleles conferring low glycerol and high ethanol yield in *Saccharomyces cerevisiae* ethanolic fermentation. *Biotechnol Biofuels* 6, 87 (2013).
47. Pais, T. M., et al. Comparative polygenic analysis of maximal ethanol accumulation capacity and tolerance to high ethanol levels of cell proliferation in yeast. *PLoS Genet* 9, e1003548 (2013).
48. Duitama, J., et al. An integrated framework for discovery and genotyping of genomic variants from high-throughput sequencing experiments. *Nucleic Acids Res* 42, e44 (2014).
49. Kaida, D., Yashiroda, H., Toh-e, A. & Kikuchi, Y. Yeast Whi2 and Psr1-phosphatase form a complex and regulate STRE-mediated gene expression. *Genes Cells* 7, 543-552 (2002).
50. Chen, Y., Stabryla, L. & Wei, N. Improved Acetic Acid Resistance in *Saccharomyces cerevisiae* by Overexpression of the WHI2 Gene Identified through Inverse Metabolic Engineering. *Appl Environ Microbiol* 82, 2156-2166 (2016).
59. van der Aa Kuhle, A., Skovgaard, K. & Jespersen, L. In vitro screening of probiotic properties of *Saccharomyces cerevisiae* var. *boulardii* and food-borne *Saccharomyces cerevisiae* strains. *Int J Food Microbiol* 101, 29-39 (2005).
83. Comyn, S. A., Flibotte, S. & Mayor, T. Recurrent background mutations in WHI2 impair proteostasis and degradation of misfolded cytosolic proteins in *Saccharomyces cerevisiae*. *Sci Rep* 7, 4183 (2017).

86. Morin, A., Moores, A. W. & Sacher, M. Dissection of *Saccharomyces cerevisiae* asci. *J Vis Exp* (2009).
87. Saunders-Singer, C. Ascus dissection. *Methods Mol Biol* 53, 59-67 (1996).
88. Gietz, R. D. Yeast transformation by the LiAc/S S carrier DNA/PEG method. *Methods Mol Biol* 1205, 1-12 (2014).
89. Benatuil, L., Perez, J. M., Belk, J. & Hsieh, C. M. An improved yeast transformation method for the generation of very large human antibody libraries. *Protein Eng Des Sel* 23, 155-159 (2010).
90. Borst, A., et al. Use of amplified fragment length polymorphism analysis to identify medically important *Candida* spp., including *C. dubliniensis*. *J Clin Microbiol* 41, 1357-1362 (2003).
91. Popolo, L., Vanoni, M. & Alberghina, L. Control of the yeast cell cycle by protein synthesis. *Exp Cell Res* 142, 69-78 (1982).
92. Boyd, A. R., et al. A flow-cytometric method for determination of yeast viability and cell number in a brewery. *FEMS Yeast Res* 3, 11-16 (2003).
93. Goldstein, A. L. & McCusker, J. H. Three new dominant drug resistance cassettes for gene disruption in *Saccharomyces cerevisiae*. *Yeast* 15, 1541-1553 (1999).
95. Baudin, A., Ozier-Kalogeropoulos, O., Denouel, A., Lacroute, F. & Cullin, C. A simple and efficient method for direct gene deletion in *Saccharomyces cerevisiae*. *Nucleic Acids Res* 21, 3329-3330 (1993).
96. Liu, J., et al. An improved allele-specific PCR primer design method for SNP marker analysis and its application. *Plant Methods* 8, 34 (2012).
97. DiCarlo, J. E., et al. Genome engineering in *Saccharomyces cerevisiae* using CRISPR-Cas systems. *Nucleic Acids Res* 41, 4336-4343 (2013).
98. Holt, S., et al. Major sulfonate transporter Soa1 in *Saccharomyces cerevisiae* and considerable substrate diversity in its fungal family. *Nat Commun* 8, 14247 (2017).
99. Farboud, B. & Meyer, B. J. Dramatic enhancement of genome editing by CRISPR/Cas9 through improved guide RNA design. *Genetics* 199, 959-971 (2015).
100. Demeke, M. M., et al. Combining inhibitor tolerance and D-xylose fermentation in industrial *Saccharomyces cerevisiae* for efficient lignocellulose-based bioethanol production. *Biotechnol Biofuels* 6, 120 (2013).
101. Swinnen, S., et al. Identification of novel causative genes determining the complex trait of high ethanol tolerance in yeast using pooled-segregant whole-genome sequence analysis. *Genome Res* 22, 975-984 (2012).
102. Teunissen, A., et al. Isolation and characterization of a freeze-tolerant diploid derivative of an industrial baker's yeast strain and its use in frozen doughs. *Appl Environ Microbiol* 68, 4780-4787 (2002).
103. Haitani, Y., et al. Identification of an acetate-tolerant strain of *Saccharomyces cerevisiae* and characterization by gene expression analysis. *J Biosci Bioeng* 114, 648-651 (2012).
105. Moons, P., Van Houdt, R., Vivijs, B., Michiels, C. W. & Aertsen, A. Integrated regulation of acetoin fermentation by quorum sensing and pH in *Serratia plymuthica* RVH1. *Appl Environ Microbiol* 77, 3422-3427 (2011).
106. Vivijs, B., Moons, P., Aertsen, A. & Michiels, C. W. Acetoin synthesis acquisition favors *Escherichia coli* growth at low pH. *Appl Environ Microbiol* 80, 6054-6061 (2014).

The invention claimed is:

1. A *Saccharomyces boulardii* strain comprising a homozygous or hemizygous mutant WHI2 allele,
   wherein the mutant allele completely abolishes Whi2 function,
   wherein the wild type allele of Whi2 is SEQ ID NO: 3,
   wherein the mutant allele
      has been disrupted or deleted by homologous recombination or disrupted with a nuclease, and
   wherein the strain produces, at 37° C., a cell-free supernatant with a pH lower than 5.

2. The *Saccharomyces boulardii* strain of claim 1, wherein the acidification of the supernatant results from the production of acetic acid by the *Saccharomyces boulardii* strain.

3. The *Saccharomyces boulardii* strain of claim 1, wherein the strain is growth deficient on acetic acid.

4. A dietary supplement or pharmaceutical composition comprising the *Saccharomyces boulardii* strain of claim 1.

5. A method of treating of gastrointestinal disorders in a mammal, the method comprising administering to the mammal a dietary supplement or pharmaceutical composition comprising a therapeutically effective amount of the *Saccharomyces boulardii* strain of claim 1.

6. The *Saccharomyces boulardii* strain of claim 1, wherein the WHI2 allele comprises SEQ ID NO:1.

7. A *Saccharomyces boulardii* strain comprising a heterologous WHI2 allele, wherein the allele completely abolishes Whi2 function.

* * * * *

SEQUENCE LISTING

```
<160> NUMBER OF SEQ ID NOS: 12

<210> SEQ ID NO 1
<211> LENGTH: 1461
<212> TYPE: DNA
<213> ORGANISM: Saccharomyces boulardii

<400> SEQUENCE: 1
atgaacgata taatcacgca agtttctcca gataatgcag agtccgctcc gattctacaa      60
gaacagcaac agcaacagaa ctcacagtac gaaggtaacg aggaggatta tggtgattca     120
ttgattcatt tgaatattca agaaaaccat tattttgtta cgagggacca gttgatgtct     180
ctacctgaat ccctattact gtgtttattt ccctcaggtg ttttttttgga ccgttgtggt     240 caggtcattg ctaatttgac cagagacgat gaggtctaca ttgttaattt ccctcctgat     300
tgttttgagt acatcatgga gatatataca aaagcgcatg atgatttgta taatcatcct     360
gtggagaaat tttttgacag gccatcaagt agctttgttt cgaatgcaaa gggggtttttt     420 ggactgagta gcaataattc aatttcgagc aacaatgagc aggatatttt acatcaaaag     480
cccgctatta ttgttttgag agaagacttg gattattatt gtgtacctca ggaggaattt     540
cagtttgatt ctactaatga agaaaataat gaggatttat tgcgacattt tatggctcaa     600
gtgaaaatgg ctgctggcag ttatttaact tcaaaaacat cgattttcca aggtttgtat     660
tcttcgaata gactaaagca acaacagcaa caacagaaaa ttgaaaagga gtccaattct     720
tcttcaaata ctaaatctac ttcgaaaaaa ttgggacctg ctgaacaaca tttaatggat     780
atgttgtgct cctccggatt cactaaggaa acttgttggg gtaacagaac tcaagaaact     840
```

```
ggcaaaacgg ttataagttg actgtctctt tgccgattgg ctaacgagac aactgaagga      900
tttaggcaaa aatttaacga ggctaaggct aagtgggagg cagagcacaa accttctcaa      960
gacaacttca tcaccccaat gcaatctaac atatcgatta actctttatc tgcaagtaaa     1020
tctaacagta acatttctac agcaaggaat ttaacaagcg gaagtacagc acctgctaca     1080
gcacgtgata agagaaaatc aaggctgtcg aaactagcag ataacgttcg ttcgcactct     1140
tcctcgagac atagttcgca gaccagaagt aaacctccgg agttgcccaa attgtatgat     1200
ctagtgccaa aacctaatat caacgctaag ctactattat tttggagaaa acctgctcgt     1260
aaatgttggt ggggtgaaga agacatagag ctagaagtgg aagttttcgg ctcttggaaa     1320
gatgaatcaa agaaaatcat tgaattgatc ttgccaacaa acgttgatcc tgaagcagaa     1380
ctacataaaa tcattgtacc cgtccgatta catattcgta gagtttggac tttagagttg     1440
agcgttattg gggtgcagtg a                                                1461

<210> SEQ ID NO 2
<211> LENGTH: 1923
<212> TYPE: DNA
<213> ORGANISM: Saccharomyces boulardii

<400> SEQUENCE: 2
atgctatcgc taaaaaaatc agcgctctcc aagttgactt tgctcagaaa cacaagaaca       60
tttacatcgt cagctttggt gcgccaaacg cagggtctg taaacggttc cgcgtccaga      120
tctgcagacg ggaagtacca cataatagat cacgagtatg actgtgtggt aatcggtgcc      180
ggtggtgccg gccttagagc ggcctttggt cttgccgagg cgggctacaa gactgcttgt     240
atatccaagc ttttccccac cagatcccac actgttgctg ctcagggtgg tatcaatgcc      300
gctctgggaa atatgcacaa ggataactgg aaatggcata tgtacgatac tgtgaaagga      360
tctgattggc taggtgacca ggactccatc cattacatga ccagggaagc gcccaaatcg      420
atcattgaac tggaacacta tggtgttcct ttttcaagaa ctgaaaacgg taagatctac      480
caaagagcct tggtggtcga gaccaaggag tacggtaagg gtgctcaggc ctatagaaca      540
tgcgctgtcg cagacaggac aggacatgct cttttacaca cgctttatgg ccaagcttta      600
agatatgaca cacatttctt tattgagtac tttgccctcg atctgttgac ccataatggc      660
gaggtcgttg gtgtcatcgc ttataatcag gaagacggta ccatccacag attcagagca      720
cacaagacca ttattgccac tggtggctat ggtagagcat acttctcttg tacctctgct      780
cacacatgta cgggtgacgg taatgccatg gtttcgcgtg ctggtttccc cttgcaagat     840
ttagagtttg ttcaattcca tccttcaggt atatatgggt ctggttgctt aatcactgaa     900
ggtgctcgtg gtgaaggtgg tttttttggtt aattctgaag gtgaaagata catgaacgt      960 tacgctccta cggccaagga tctagcttgt agagatgtcg tttccagagc aatcaccatg     1020
gagatcagag aaggcagagg tgttggtaag aaaaaggacc acatgtactt acaattgagc     1080
catctaccct cggaagttct aaaggaaaga ttgccaggta tctctgaaac agcagccatt     1140
tttgctggtg tagacgtcac caaggaacct attcccatta ttcctaccgt ccactataac     1200
atgggtggta ttcccacgaa gtggaatggt gaggcattaa ccattgatga agaaactggc     1260
gaagacaagg ttattcccgg tttaatggct tgtggtgaag ccgcttgtgt ttctgtccat     1320
ggtgccaata gattaggtgc caattccttg ttggatcttg ttgtctttgg tcgtgctgtt     1380
gcccatacgg ttgctgacac tttacagcct gggttgccac acaaaccact accttctgat     1440
ttgggtaaag aatccatcgc aaacttggat aaactaagaa atgctaatgg ttcaagatct     1500
```

```
acggcagaaa ttagaatgaa tatgaaacaa actatgcaaa aggatgtttc cgtctttaga    1560
acacaatcat ctttagatga aggtgttcgg aacattactg cagtagagaa gacctttgat    1620
gatgtgaaga cgaccgatag atcaatgatc tggaattctg acttggttga aactctggag    1680
ctacagaact tattaacctg tgcctcccaa acagctgttt ccgctgctaa tagaaaggaa    1740
tcccgtggtg ctcatgcaag agaggattat ccaaatagag atgacgaaca ttggatgaag    1800
catacattat cctggcaaaa ggacgtcgct gccccagtga ctttgaaata cagaagggtt    1860
atcgatcaca ctttggacga aaaggaatgt ccttccgtac ctccaactgt aagagcctac    1920
taa                                                                  1923

<210> SEQ ID NO 3
<211> LENGTH: 1461
<212> TYPE: DNA
<213> ORGANISM: Saccharomyces boulardii

<400> SEQUENCE: 3
atggacgata taatcacgca gtttctccca gataatgcag agtccgctcc gattctacaa      60
gaacagcaac agcaacagaa ctcacagtac gaaggtaacg aggaggatta tggtgattca     120
ttgattcatt tgaatattca agaaaaccat tatttcatta cgagggacca gttgatgtct     180
ctacctgaat ccctattact gtgtttattt ccctcaggtg ttttttttgga ccgttgtggt     240 caggtcatta ctaatttgac cagagacgat gaggtctaca ttgttaattt ccctcctgat     300
tgttttgagt acatcatgga gatatataca aaagcgcatg atgatttgta taatcatcct     360
gtggagaaat ttttgacag accatcaagt agctttgttt cgaatgcaaa gggatttttt     420
ggactgagta gcaataattc aatttcgagc aacaatgagc aggatatttt acatcaaaag     480
cccgctatta ttgttttgag agaagacttg gattattatt gtgtacctca ggaggaattt     540
cagtttgatt ccactaatga agaaaataat gaggatttat gcgacatttt tatggctcaa     600
gtgaaaatgg ctgctggcag ttatttaact tcaaaaacat cgattttcca aggtttgtat     660
tcttcgaata gactaaagca acaacagcaa caacagaaaa ttgaaaaggg gtccaattct     720
tcttcaaata ctaaatctac ttcgaaaaaa ttgggacctg ctgaacaaca tttaatggat     780
atgttgtgct cctccggatt caccaaggaa acttgttggg gtaacagaac tcaagaaact     840
ggcaaaacgg ttataagttc actgtctctt tgccgattgg ctaacgagac aactgaagga     900
tttaggcaaa aatttaacga ggctaaggct aagtgggagg cagagcacaa accttctcaa     960
gacaacttca tcaccccaat gcaatctaac atatcgatta ctctctttatc tgcaagtaaa    1020 tctaacagta ccatttctac agcaaggaat ttaacaagcg gaagtacagc acctgctaca    1080
gcacgtgata agagaaaatc aaggctgtcg aaactagcag ataacgttcg ttcgcactct    1140
tcctcgagac atagttcgca gaccagaagt aaacctccgg agttgcccaa attgtatgat    1200
ctagtgccaa aacctaatat caacgctaag ctactattat tttggagaaa acctgctcgt    1260
aaatgttggt ggggtgaaga agacatagag ctagaagtgg aagtcttcgg ctcttggaaa    1320
gatgaatcaa agaaaatcat tgaattgatc ttgccaacaa cgttgatccc tgaagcagaa    1380
ctacataaaa tcattgtacc cgtccgatta catattcgta gagtttggac tttagagttg    1440
agcgttattg gggtgcagtg a                                              1461

<210> SEQ ID NO 4
<211> LENGTH: 486
<212> TYPE: PRT
```

-continued

<213> ORGANISM: Saccharomyces boulardii

<400> SEQUENCE: 4

```
Met Asp Asp Ile Ile Thr Gln Val Ser Pro Asp Asn Ala Glu Ser Ala
1               5                   10                  15

Pro Ile Leu Gln Glu Gln Gln Gln Gln Asn Ser Gln Tyr Glu Gly
            20                  25                  30

Asn Glu Glu Asp Tyr Gly Asp Ser Leu Ile His Leu Asn Ile Gln Glu
            35                  40                  45

Asn His Tyr Phe Ile Thr Arg Asp Gln Leu Met Ser Leu Pro Glu Ser
        50                  55                  60

Leu Leu Leu Cys Leu Phe Pro Ser Gly Val Phe Leu Asp Arg Cys Gly
65                  70                  75                  80

Gln Val Ile Thr Asn Leu Thr Arg Asp Asp Glu Val Tyr Ile Val Asn
                    85                  90                  95

Phe Pro Pro Asp Cys Phe Glu Tyr Ile Met Glu Ile Tyr Thr Lys Ala
                100                 105                 110

His Asp Asp Leu Tyr Asn His Pro Val Glu Lys Phe Phe Asp Arg Pro
            115                 120                 125

Ser Ser Ser Phe Val Ser Asn Ala Lys Gly Phe Gly Leu Ser Ser
        130                 135                 140

Asn Asn Ser Ile Ser Ser Asn Asn Glu Gln Asp Ile Leu His Gln Lys
145                 150                 155                 160

Pro Ala Ile Ile Val Leu Arg Glu Asp Leu Asp Tyr Tyr Cys Val Pro
                165                 170                 175

Gln Glu Glu Phe Gln Phe Asp Ser Thr Asn Glu Glu Asn Asn Glu Asp
            180                 185                 190

Leu Leu Arg His Phe Met Ala Gln Val Lys Met Ala Ala Gly Ser Tyr
        195                 200                 205

Leu Thr Ser Lys Thr Ser Ile Phe Gln Gly Leu Tyr Ser Ser Asn Arg
210                 215                 220

Leu Lys Gln Gln Gln Gln Gln Lys Ile Glu Lys Gly Ser Asn Ser
225                 230                 235                 240

Ser Ser Asn Thr Lys Ser Thr Ser Lys Lys Leu Gly Pro Ala Glu Gln
                245                 250                 255

His Leu Met Asp Met Leu Cys Ser Ser Gly Phe Thr Lys Glu Thr Cys
            260                 265                 270

Trp Gly Asn Arg Thr Gln Glu Thr Gly Lys Thr Val Ile Ser Ser Leu
        275                 280                 285

Ser Leu Cys Arg Leu Ala Asn Glu Thr Thr Glu Gly Phe Arg Gln Lys
    290                 295                 300

Phe Asn Glu Ala Lys Ala Lys Trp Glu Ala Glu His Lys Pro Ser Gln
305                 310                 315                 320

Asp Asn Phe Ile Thr Pro Met Gln Ser Asn Ile Ser Ile Asn Ser Leu
                325                 330                 335

Ser Ala Ser Lys Ser Asn Ser Thr Ile Ser Thr Ala Arg Asn Leu Thr
            340                 345                 350

Ser Gly Ser Thr Ala Pro Ala Thr Ala Arg Asp Lys Arg Lys Ser Arg
        355                 360                 365

Leu Ser Lys Leu Ala Asp Asn Val Arg Ser His Ser Ser Arg His
    370                 375                 380

Ser Ser Gln Thr Arg Ser Lys Pro Pro Glu Leu Pro Lys Leu Tyr Asp
385                 390                 395                 400
```

Leu Val Pro Lys Pro Asn Ile Asn Ala Lys Leu Leu Leu Phe Trp Arg
            405                 410                 415

Lys Pro Ala Arg Lys Cys Trp Trp Gly Glu Glu Asp Ile Glu Leu Glu
        420                 425                 430

Val Glu Val Phe Gly Ser Trp Lys Asp Glu Ser Lys Lys Ile Ile Glu
        435                 440                 445

Leu Ile Leu Pro Thr Asn Val Asp Pro Glu Ala Glu Leu His Lys Ile
    450                 455                 460

Ile Val Pro Val Arg Leu His Ile Arg Arg Val Trp Thr Leu Glu Leu
465                 470                 475                 480

Ser Val Ile Gly Val Gln
                485

<210> SEQ ID NO 5
<211> LENGTH: 286
<212> TYPE: PRT
<213> ORGANISM: Saccharomyces boulardii

<400> SEQUENCE: 5

Met Asn Asp Ile Ile Thr Gln Val Ser Pro Asn Ala Glu Ser Ala
1               5                   10                  15

Pro Ile Leu Gln Glu Gln Gln Gln Gln Asn Ser Gln Tyr Glu Gly
            20                  25                  30

Asn Glu Glu Asp Tyr Gly Asp Ser Leu Ile His Leu Asn Ile Gln Glu
        35                  40                  45

Asn His Tyr Phe Val Thr Arg Asp Gln Leu Met Ser Leu Pro Glu Ser
    50                  55                  60

Leu Leu Leu Cys Leu Phe Pro Ser Gly Val Phe Leu Asp Arg Cys Gly
65                  70                  75                  80

Gln Val Ile Ala Asn Leu Thr Arg Asp Asp Glu Val Tyr Ile Val Asn
                85                  90                  95

Phe Pro Pro Asp Cys Phe Glu Tyr Ile Met Glu Ile Tyr Thr Lys Ala
            100                 105                 110

His Asp Asp Leu Tyr Asn His Pro Val Glu Lys Phe Phe Asp Arg Pro
        115                 120                 125

Ser Ser Ser Phe Val Ser Asn Ala Lys Gly Phe Phe Gly Leu Ser Ser
    130                 135                 140

Asn Asn Ser Ile Ser Ser Asn Glu Gln Asp Ile Leu His Gln Lys
145                 150                 155                 160

Pro Ala Ile Ile Val Leu Arg Glu Asp Leu Asp Tyr Tyr Cys Val Pro
                165                 170                 175

Gln Glu Glu Phe Gln Phe Asp Ser Thr Asn Glu Glu Asn Asn Glu Asp
            180                 185                 190

Leu Leu Arg His Phe Met Ala Gln Val Lys Met Ala Ala Gly Ser Tyr
        195                 200                 205

Leu Thr Ser Lys Thr Ser Ile Phe Gln Gly Leu Tyr Ser Ser Asn Arg
    210                 215                 220

Leu Lys Gln Gln Gln Gln Gln Lys Ile Glu Lys Glu Ser Asn Ser
225                 230                 235                 240

Ser Ser Asn Thr Lys Ser Thr Ser Lys Lys Leu Gly Pro Ala Glu Gln
                245                 250                 255

His Leu Met Asp Met Leu Cys Ser Ser Gly Phe Thr Lys Glu Thr Cys
            260                 265                 270

Trp Gly Asn Arg Thr Gln Glu Thr Gly Lys Thr Val Ile Ser
        275                 280                 285

<210> SEQ ID NO 6
<211> LENGTH: 1923
<212> TYPE: DNA
<213> ORGANISM: Saccharomyces cerevisiae

<400> SEQUENCE: 6

| | | | | | |
|---|---|---|---|---|---|
| atgctatcgc | taaaaaaatc | agcgctctcc | aagttgactt | tgctcagaaa | cacaagaaca | 60 |
| tttacatcgt | cagctttggt | gcgccaaacg | cagggctctg | taaacggttc | cgcgtccaga | 120 |
| tctgcagacg | ggaagtacca | cataatagat | cacgagtatg | actgtgtggt | aatcggtgcc | 180 |
| ggtggtgccg | gccttagagc | ggcctttggt | cttgccgagg | cgggctacaa | gactgcttgt | 240 |
| atatccaagc | ttttccccac | cagatcccac | actgttgctg | ctcagggtgg | tatcaatgcc | 300 |
| gctctgggaa | atatgcacaa | ggataactgg | aaatggcata | tgtacgatac | tgtgaaagga | 360 |
| tctgattggc | taggtgacca | ggactccatc | cattacatga | ccagggaagc | gcccaaatcg | 420 |
| atcattgaac | tggaacacta | tggtgttcct | ttttcaagaa | ctgaaaacgg | taagatctac | 480 |
| caaagagcct | tggtggtca | gaccaaggag | tacggtaagg | gtgctcaggc | ctatagaaca | 540 |
| tgcgctgtcg | cagacaggac | aggacatgct | ctttacaca | cgctttatgg | ccaagcttta | 600 |
| agacatgaca | cacatttctt | tattgagtac | tttgccctcg | atctgttgac | ccataatggc | 660 |
| gaggtcgttg | gtgtcatcgc | ttataatcag | gaagacggta | ccatccacag | attcagagca | 720 |
| cacaagacca | ttattgccac | tggtggctat | ggtagagcat | acttctcttg | tacctctgct | 780 |
| cacacatgta | cgggtgacgg | taatgccatg | gtttcgcgtg | ctggtttccc | cttgcaagat | 840 |
| ttagagtttg | ttcaattcca | tccttcaggt | atatatgggt | ctggttgctt | aatcactgaa | 900 |
| ggtgctcgtg | gtgaaggtgg | ttttttggtt | aattctgaag | gtgaaagatt | catgaacgt | 960 |
| tacgctccta | cggccaagga | tctagcttgt | agagatgtcg | tttccagagc | aatcaccatg | 1020 |
| gagatcagag | aaggcagagg | tgttggtaag | aaaaaggacc | acatgtactt | acaattgagc | 1080 |
| catctacctc | cggaagttct | aaaggaaaga | ttgccaggta | tctctgaaac | agcagccatt | 1140 |
| tttgctggtg | tagacgtcac | caaggaacct | attcccatta | ttcctaccgt | ccactataac | 1200 |
| atgggtggta | ttcccacgaa | gtggaatggt | gaggcattaa | ccattgatga | agaaactggc | 1260 |
| gaagacaagg | ttattcccgg | tttaatggct | tgtggtgaag | ccgcttgtgt | ttctgtccat | 1320 |
| ggtgccaata | gattaggtgc | caattccttg | ttggatcttg | ttgtctttgg | tcgtgctgtt | 1380 |
| gcccatacgg | ttgctgacac | tttacagcct | gggttgccac | acaaaccact | accttctgat | 1440 |
| ttgggtaaag | aatccatcgc | aaacttggat | aaactaagaa | atgctaatgg | ttcaagatct | 1500 |
| acggcagaaa | ttagaatgaa | tatgaaacaa | actatgcaaa | aggatgtttc | cgtctttaga | 1560 |
| acacaatcat | ctttagatga | aggtgttcgg | aacattactg | cagtagagaa | gacctttgat | 1620 |
| gatgtgaaga | cgaccgatag | atcaatgatc | tggaattctg | acttggttga | aactctggag | 1680 |
| ctacagaact | tattaacctg | tgcctcccaa | acagctgttt | ccgctgctaa | tagaaaggaa | 1740 |
| tcccgtggtg | ctcatgcaag | agaggattat | ccaaatagag | atgacgaaca | ttggatgaag | 1800 |
| catacattat | cctggcaaaa | ggacgtcgct | gccccagtga | ctttgaaata | cagaagggtt | 1860 |
| atcgatcaca | ctttggacga | aaaggaatgt | ccttccgtac | tccaactgt | aagagcctac | 1920 |
| taa | | | | | | 1923 |

<210> SEQ ID NO 7
<211> LENGTH: 640
<212> TYPE: PRT

<213> ORGANISM: Saccharomyces cerevisiae

<400> SEQUENCE: 7

```
Met Leu Ser Leu Lys Ser Ala Leu Ser Lys Leu Thr Leu Leu Arg
1               5                   10                  15

Asn Thr Arg Thr Phe Thr Ser Ser Ala Leu Val Arg Gln Thr Gln Gly
            20                  25                  30

Ser Val Asn Gly Ser Ala Ser Arg Ser Ala Asp Gly Lys Tyr His Ile
            35                  40                  45

Ile Asp His Glu Tyr Asp Cys Val Val Ile Gly Ala Gly Gly Ala Gly
    50                  55                  60

Leu Arg Ala Ala Phe Gly Leu Ala Glu Ala Gly Tyr Lys Thr Ala Cys
65                  70                  75                  80

Ile Ser Lys Leu Phe Pro Thr Arg Ser His Thr Val Ala Ala Gln Gly
                85                  90                  95

Gly Ile Asn Ala Ala Leu Gly Asn Met His Lys Asp Asn Trp Lys Trp
            100                 105                 110

His Met Tyr Asp Thr Val Lys Gly Ser Asp Trp Leu Gly Asp Gln Asp
            115                 120                 125

Ser Ile His Tyr Met Thr Arg Glu Ala Pro Lys Ser Ile Ile Glu Leu
        130                 135                 140

Glu His Tyr Gly Val Pro Phe Ser Arg Thr Glu Asn Gly Lys Ile Tyr
145                 150                 155                 160

Gln Arg Ala Phe Gly Gly Gln Thr Lys Glu Tyr Gly Lys Gly Ala Gln
                165                 170                 175

Ala Tyr Arg Thr Cys Ala Val Ala Asp Arg Thr Gly His Ala Leu Leu
            180                 185                 190

His Thr Leu Tyr Gly Gln Ala Leu Arg His Asp Thr His Phe Phe Ile
        195                 200                 205

Glu Tyr Phe Ala Leu Asp Leu Leu Thr His Asn Gly Glu Val Val Gly
    210                 215                 220

Val Ile Ala Tyr Asn Gln Glu Asp Gly Thr Ile His Arg Phe Arg Ala
225                 230                 235                 240

His Lys Thr Ile Ile Ala Thr Gly Gly Tyr Gly Arg Ala Tyr Phe Ser
                245                 250                 255

Cys Thr Ser Ala His Thr Cys Thr Gly Asp Gly Asn Ala Met Val Ser
            260                 265                 270

Arg Ala Gly Phe Pro Leu Gln Asp Leu Glu Phe Val Gln Phe His Pro
        275                 280                 285

Ser Gly Ile Tyr Gly Ser Gly Cys Leu Ile Thr Glu Gly Ala Arg Gly
    290                 295                 300

Glu Gly Gly Phe Leu Val Asn Ser Glu Gly Glu Arg Phe Met Glu Arg
305                 310                 315                 320

Tyr Ala Pro Thr Ala Lys Asp Leu Ala Cys Arg Asp Val Val Ser Arg
                325                 330                 335

Ala Ile Thr Met Glu Ile Arg Glu Gly Arg Gly Val Gly Lys Lys Lys
            340                 345                 350

Asp His Met Tyr Leu Gln Leu Ser His Leu Pro Pro Glu Val Leu Lys
        355                 360                 365

Glu Arg Leu Pro Gly Ile Ser Glu Thr Ala Ala Ile Phe Ala Gly Val
    370                 375                 380

Asp Val Thr Lys Glu Pro Ile Pro Ile Ile Pro Thr Val His Tyr Asn
385                 390                 395                 400
```

```
Met Gly Gly Ile Pro Thr Lys Trp Asn Gly Glu Ala Leu Thr Ile Asp
                405                 410                 415

Glu Glu Thr Gly Glu Asp Lys Val Ile Pro Gly Leu Met Ala Cys Gly
            420                 425                 430

Glu Ala Ala Cys Val Ser Val His Gly Ala Asn Arg Leu Gly Ala Asn
        435                 440                 445

Ser Leu Leu Asp Leu Val Val Phe Gly Arg Ala Val Ala His Thr Val
    450                 455                 460

Ala Asp Thr Leu Gln Pro Gly Leu Pro His Lys Pro Leu Pro Ser Asp
465                 470                 475                 480

Leu Gly Lys Glu Ser Ile Ala Asn Leu Asp Lys Leu Arg Asn Ala Asn
                485                 490                 495

Gly Ser Arg Ser Thr Ala Glu Ile Arg Met Asn Met Lys Gln Thr Met
            500                 505                 510

Gln Lys Asp Val Ser Val Phe Arg Thr Gln Ser Ser Leu Asp Glu Gly
        515                 520                 525

Val Arg Asn Ile Thr Ala Val Glu Lys Thr Phe Asp Asp Val Lys Thr
    530                 535                 540

Thr Asp Arg Ser Met Ile Trp Asn Ser Asp Leu Val Glu Thr Leu Glu
545                 550                 555                 560

Leu Gln Asn Leu Leu Thr Cys Ala Ser Gln Thr Ala Val Ser Ala Ala
                565                 570                 575

Asn Arg Lys Glu Ser Arg Gly Ala His Ala Arg Glu Asp Tyr Pro Asn
            580                 585                 590

Arg Asp Asp Glu His Trp Met Lys His Thr Leu Ser Trp Gln Lys Asp
        595                 600                 605

Val Ala Ala Pro Val Thr Leu Lys Tyr Arg Arg Val Ile Asp His Thr
    610                 615                 620

Leu Asp Glu Lys Glu Cys Pro Ser Val Pro Pro Thr Val Arg Ala Tyr
625                 630                 635                 640

<210> SEQ ID NO 8
<211> LENGTH: 640
<212> TYPE: PRT
<213> ORGANISM: Saccharomyces boulardii

<400> SEQUENCE: 8

Met Leu Ser Leu Lys Lys Ser Ala Leu Ser Lys Leu Thr Leu Leu Arg
1               5                   10                  15

Asn Thr Arg Thr Phe Thr Ser Ser Ala Leu Val Arg Gln Thr Gln Gly
            20                  25                  30

Ser Val Asn Gly Ser Ala Ser Arg Ser Ala Asp Gly Lys Tyr His Ile
        35                  40                  45

Ile Asp His Glu Tyr Asp Cys Val Val Ile Gly Ala Gly Gly Ala Gly
    50                  55                  60

Leu Arg Ala Ala Phe Gly Leu Ala Glu Ala Gly Tyr Lys Thr Ala Cys
65                  70                  75                  80

Ile Ser Lys Leu Phe Pro Thr Arg Ser His Thr Val Ala Ala Gln Gly
                85                  90                  95

Gly Ile Asn Ala Ala Leu Gly Asn Met His Lys Asp Asn Trp Lys Trp
            100                 105                 110

His Met Tyr Asp Thr Val Lys Gly Ser Asp Trp Leu Gly Asp Gln Asp
        115                 120                 125

Ser Ile His Tyr Met Thr Arg Glu Ala Pro Lys Ser Ile Ile Glu Leu
    130                 135                 140
```

-continued

```
Glu His Tyr Gly Val Pro Phe Ser Arg Thr Glu Asn Gly Lys Ile Tyr
145                 150                 155                 160

Gln Arg Ala Phe Gly Gln Thr Lys Glu Tyr Gly Lys Gly Ala Gln
            165                 170                 175

Ala Tyr Arg Thr Cys Ala Val Ala Asp Arg Thr Gly His Ala Leu Leu
            180                 185                 190

His Thr Leu Tyr Gly Gln Ala Leu Arg Tyr Asp Thr His Phe Phe Ile
            195                 200                 205

Glu Tyr Phe Ala Leu Asp Leu Leu Thr His Asn Gly Glu Val Val Gly
            210                 215                 220

Val Ile Ala Tyr Asn Gln Glu Asp Gly Thr Ile His Arg Phe Arg Ala
225                 230                 235                 240

His Lys Thr Ile Ile Ala Thr Gly Gly Tyr Gly Arg Ala Tyr Phe Ser
            245                 250                 255

Cys Thr Ser Ala His Thr Cys Thr Gly Asp Gly Asn Ala Met Val Ser
            260                 265                 270

Arg Ala Gly Phe Pro Leu Gln Asp Leu Glu Phe Val Gln Phe His Pro
            275                 280                 285

Ser Gly Ile Tyr Gly Ser Gly Cys Leu Ile Thr Glu Gly Ala Arg Gly
            290                 295                 300

Glu Gly Gly Phe Leu Val Asn Ser Glu Gly Glu Arg Tyr Met Glu Arg
305                 310                 315                 320

Tyr Ala Pro Thr Ala Lys Asp Leu Ala Cys Arg Asp Val Val Ser Arg
            325                 330                 335

Ala Ile Thr Met Glu Ile Arg Glu Gly Arg Gly Val Gly Lys Lys Lys
            340                 345                 350

Asp His Met Tyr Leu Gln Leu Ser His Leu Pro Pro Glu Val Leu Lys
            355                 360                 365

Glu Arg Leu Pro Gly Ile Ser Glu Thr Ala Ala Ile Phe Ala Gly Val
            370                 375                 380

Asp Val Thr Lys Glu Pro Ile Pro Ile Ile Pro Thr Val His Tyr Asn
385                 390                 395                 400

Met Gly Gly Ile Pro Thr Lys Trp Asn Gly Glu Ala Leu Thr Ile Asp
            405                 410                 415

Glu Glu Thr Gly Glu Asp Lys Val Ile Pro Gly Leu Met Ala Cys Gly
            420                 425                 430

Glu Ala Ala Cys Val Ser Val His Gly Ala Asn Arg Leu Gly Ala Asn
            435                 440                 445

Ser Leu Leu Asp Leu Val Val Phe Gly Arg Ala Val Ala His Thr Val
            450                 455                 460

Ala Asp Thr Leu Gln Pro Gly Leu Pro His Lys Pro Leu Pro Ser Asp
465                 470                 475                 480

Leu Gly Lys Glu Ser Ile Ala Asn Leu Asp Lys Leu Arg Asn Ala Asn
            485                 490                 495

Gly Ser Arg Ser Thr Ala Glu Ile Arg Met Asn Met Lys Gln Thr Met
            500                 505                 510

Gln Lys Asp Val Ser Val Phe Arg Thr Gln Ser Ser Leu Asp Glu Gly
            515                 520                 525

Val Arg Asn Ile Thr Ala Val Glu Lys Thr Phe Asp Val Lys Thr
            530                 535                 540

Thr Asp Arg Ser Met Ile Trp Asn Ser Asp Leu Val Glu Thr Leu Glu
545                 550                 555                 560
```

```
Leu Gln Asn Leu Leu Thr Cys Ala Ser Gln Thr Ala Val Ser Ala Ala
                565                 570                 575

Asn Arg Lys Glu Ser Arg Gly Ala His Ala Arg Glu Asp Tyr Pro Asn
            580                 585                 590

Arg Asp Asp Glu His Trp Met Lys His Thr Leu Ser Trp Gln Lys Asp
        595                 600                 605

Val Ala Ala Pro Val Thr Leu Lys Tyr Arg Arg Val Ile Asp His Thr
    610                 615                 620

Leu Asp Glu Lys Glu Cys Pro Ser Val Pro Pro Thr Val Arg Ala Tyr
625                 630                 635                 640

<210> SEQ ID NO 9
<211> LENGTH: 23
<212> TYPE: DNA
<213> ORGANISM: Artificial Sequence
<220> FEATURE:
<223> OTHER INFORMATION: gRNA recognition sites

<400> SEQUENCE: 9
ggctgatttt cgcagttcgg ggg                                            23

<210> SEQ ID NO 10
<211> LENGTH: 35
<212> TYPE: PRT
<213> ORGANISM: Saccharomyces cerevisiae

<400> SEQUENCE: 10

Cys Ala Val Ala Asp Arg Thr Gly His Ala Leu Leu His Thr Leu Tyr
1               5                   10                  15

Gly Gln Ala Leu Arg His Asp Thr His Phe Glu Gly Glu Arg Phe Met
            20                  25                  30

Glu Arg Tyr
        35

<210> SEQ ID NO 11
<211> LENGTH: 35
<212> TYPE: PRT
<213> ORGANISM: Saccharomyces boulardii

<400> SEQUENCE: 11

Cys Ala Val Ala Asp Arg Thr Gly His Ala Leu Leu His Thr Leu Tyr
1               5                   10                  15

Gly Gln Ala Leu Arg Tyr Asp Thr His Phe Glu Gly Glu Arg Tyr Met
            20                  25                  30

Glu Arg Tyr
        35

<210> SEQ ID NO 12
<211> LENGTH: 35
<212> TYPE: PRT
<213> ORGANISM: Saccharomyces cerevisiae

<400> SEQUENCE: 12

Cys Ala Val Ala Asp Arg Thr Gly His Ala Leu Leu His Thr Leu Tyr
1               5                   10                  15

Gly Gln Ala Leu Arg Tyr Asp Thr His Phe Glu Gly Glu Arg Phe Met
            20                  25                  30

Glu Arg Tyr
        35
```